United States Patent
Edinger et al.

(10) Patent No.: US 10,494,607 B2
(45) Date of Patent: Dec. 3, 2019

(54) CD34+,CD45− PLACENTAL STEM CELL-ENRICHED CELL POPULATIONS

(75) Inventors: James W. Edinger, Belford, NJ (US); Robert J. Hariri, Florham Park, NJ (US); Jia-Lun Wang, Cherry Hill, NJ (US); Qian Ye, Livingston, NJ (US); Marian Pereira, Cranford, NJ (US); Sascha Dawn Abramson, Hillsborough, NJ (US); Kristen S. Labazzo, Springfield, NJ (US)

(73) Assignee: CELULARITY, INC., Warren, NJ (US)

( * ) Notice: Subject to any disclaimer, the term of this patent is extended or adjusted under 35 U.S.C. 154(b) by 0 days.

(21) Appl. No.: 12/030,170

(22) Filed: Feb. 12, 2008

(65) Prior Publication Data
US 2008/0206343 A1 Aug. 28, 2008

Related U.S. Application Data

(60) Provisional application No. 60/966,577, filed on Aug. 28, 2007, provisional application No. 60/906,064, filed on Mar. 8, 2007, provisional application No. 60/905,664, filed on Mar. 7, 2007, provisional application No. 60/901,076, filed on Feb. 12, 2007, provisional application No. 60/901,066, filed on Feb. 12, 2007.

(51) Int. Cl.
*C12N 5/073* (2010.01)
*C12N 5/071* (2010.01)
*A01K 67/027* (2006.01)
*C12N 5/074* (2010.01)
*C12N 5/077* (2010.01)
*A61K 35/12* (2015.01)

(52) U.S. Cl.
CPC .......... *C12N 5/067* (2013.01); *A01K 67/0271* (2013.01); *C12N 5/0605* (2013.01); *C12N 5/0607* (2013.01); *C12N 5/0655* (2013.01); *A01K 2267/0337* (2013.01); *A61K 2035/128* (2013.01); *C12N 2500/30* (2013.01); *C12N 2500/36* (2013.01); *C12N 2500/62* (2013.01); *C12N 2501/15* (2013.01); *C12N 2501/999* (2013.01); *C12N 2506/02* (2013.01); *C12N 2506/03* (2013.01); *C12N 2533/32* (2013.01); *C12N 2533/40* (2013.01); *C12N 2533/74* (2013.01)

(58) Field of Classification Search
CPC .................................................. C12N 5/0605
See application file for complete search history.

(56) References Cited

U.S. PATENT DOCUMENTS

| | | |
|---|---|---|
| 3,862,002 A | 1/1975 | Sanders |
| 4,798,824 A | 1/1989 | Belzer et al. |
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,372,581 A | 12/1994 | Anderson |
| 5,415,665 A | 5/1995 | Hessel et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,552,267 A | 9/1996 | Stern et al. |
| 5,591,625 A | 1/1997 | Gerson et al. |
| 5,605,822 A | 2/1997 | Emerson et al. |
| 5,613,982 A | 3/1997 | Goldstein |
| 5,627,059 A | 5/1997 | Capecchi et al. |
| 5,635,386 A | 6/1997 | Palsson et al. |
| 5,635,387 A | 6/1997 | Fei et al. |
| 5,635,517 A | 6/1997 | Muller et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,698,579 A | 12/1997 | Muller |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |

(Continued)

FOREIGN PATENT DOCUMENTS

| | | |
|---|---|---|
| CN | 1407088 | 4/2003 |
| CN | 1548529 | 5/2003 |

(Continued)

OTHER PUBLICATIONS

In 't Anker et al. Isolation of Mesenchymal Stem Cells of Fetal or Maternal Origin from Human Placenta. Stem Cells, 2004, vol. 22, pp. 1388-1345.*

(Continued)

*Primary Examiner* — Thaian N Ton
*Assistant Examiner* — David A. Montanari
(74) *Attorney, Agent, or Firm* — Geoffry T. Knudsen

(57) ABSTRACT

Provided herein are methods and compositions for the production of hepatocytes from placenta stem cells. Further provided herein is the use of such hepatocytes in the treatment of, and intervention in, for example, trauma, inflammation, and degenerative disorders of the liver. Also provided herein are compositions and methods relating to combinations of nanofibrous scaffolds and adherent placental stem cells and methods of using the same in cartilage repair. Finally, provided herein are compositions and methods relating to nonadherent, CD34+CD45− stem cells from placenta.

5 Claims, 10 Drawing Sheets

(56) References Cited

U.S. PATENT DOCUMENTS

Figure 1:
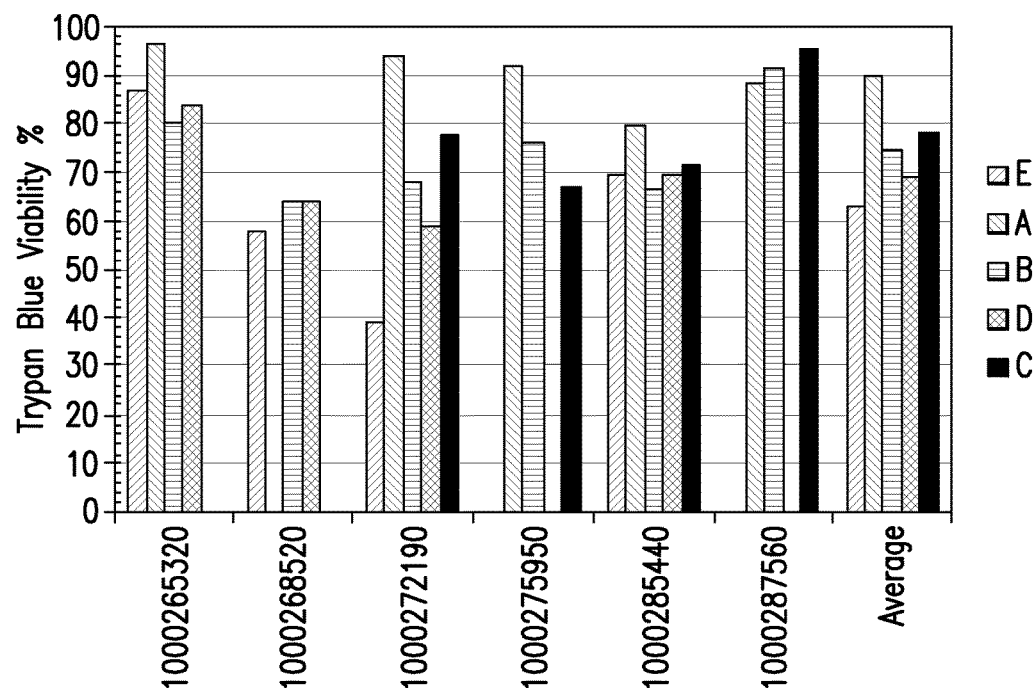

| | | |
|---|---|---|
| 5,733,542 A | 3/1998 | Haynesworth et al. |
| 5,744,361 A | 4/1998 | Hoffman et al. |
| 5,750,376 A | 5/1998 | Weiss et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,798,368 A | 8/1998 | Muller et al. |
| 5,806,529 A | 9/1998 | Reisner et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,849,553 A | 12/1998 | Anderson et al. |
| 5,851,984 A | 12/1998 | Matthews et al. |
| 5,858,782 A | 1/1999 | Long et al. |
| 5,861,315 A | 1/1999 | Nakahata et al. |
| 5,866,414 A | 2/1999 | Badylak et al. |
| 5,874,301 A | 2/1999 | Keller et al. |
| 5,874,448 A | 2/1999 | Muller et al. |
| 5,877,200 A | 3/1999 | Muller |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,905,041 A | 5/1999 | Beug et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,928,214 A | 7/1999 | Rubinstein et al. |
| 5,929,117 A | 7/1999 | Muller et al. |
| 5,955,476 A | 9/1999 | Muller et al. |
| 5,993,429 A | 11/1999 | Kuypers et al. |
| 6,030,836 A | 2/2000 | Thiede |
| 6,059,968 A | 5/2000 | Wolf, Jr. |
| 6,110,739 A | 8/2000 | Keller et al. |
| 6,179,819 B1 | 1/2001 | Haswel |
| 6,190,368 B1 | 2/2001 | Kuypers et al. |
| 6,255,112 B1 | 7/2001 | Thiede et al. |
| 6,281,230 B1 | 8/2001 | Muller et al. |
| 6,288,089 B1 | 9/2001 | Zawada et al. |
| 6,307,056 B1 | 10/2001 | Corbett et al. |
| 6,316,471 B1 | 11/2001 | Muller et al. |
| 6,326,019 B1 | 12/2001 | Tseng |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,458,810 B1 | 10/2002 | Muller et al. |
| 6,461,615 B1 | 10/2002 | Boyse et al. |
| 6,461,645 B1 | 10/2002 | Boyse et al. |
| 6,476,052 B1 | 11/2002 | Muller et al. |
| 6,555,554 B2 | 4/2003 | Muller et al. |
| 7,045,148 B2 | 5/2006 | Hariri |
| 7,147,626 B2 | 12/2006 | Goodman et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 * | 12/2007 | Hariri .......................... 424/93.1 |
| 7,468,276 B2 | 12/2008 | Hariri |
| 7,498,171 B2 | 3/2009 | Hariri et al. |
| 7,638,141 B2 | 12/2009 | Hariri |
| 7,682,803 B2 | 3/2010 | Paludan et al. |
| 7,700,090 B2 | 4/2010 | Heidaran et al. |
| 7,909,806 B2 | 3/2011 | Goodman |
| 7,914,779 B2 | 3/2011 | Hariri |
| 7,928,280 B2 | 4/2011 | Hariri et al. |
| 7,976,836 B2 | 7/2011 | Hariri |
| 7,993,918 B2 | 8/2011 | Paludan et al. |
| 8,017,393 B2 | 9/2011 | Lanza et al. |
| 8,057,788 B2 | 11/2011 | Hariri |
| 8,057,789 B2 | 11/2011 | Hariri |
| 8,071,135 B2 | 12/2011 | Liu et al. |
| 8,071,376 B2 | 12/2011 | Heidaran |
| 8,105,634 B2 | 1/2012 | Liu et al. |
| 2001/0038836 A1 | 11/2001 | During et al. |
| 2001/0044124 A1 | 11/2001 | Bacus |
| 2002/0028510 A1 | 3/2002 | Sanberg et al. |
| 2002/0045643 A1 | 4/2002 | Muller et al. |
| 2002/0086005 A1 | 7/2002 | Chiu et al. |
| 2002/0123141 A1 | 9/2002 | Hariri |
| 2002/0132343 A1 | 9/2002 | Lum |
| 2002/0160510 A1 | 10/2002 | Hariri |
| 2003/0003573 A1 | 1/2003 | Rambhatle et al. |
| 2003/0032179 A1 | 2/2003 | Hariri |
| 2003/0044976 A1 | 3/2003 | Dominko et al. |
| 2003/0045552 A1 | 3/2003 | Robarge et al. |
| 2003/0096841 A1 | 5/2003 | Robarge et al. |
| 2003/0180269 A1 | 9/2003 | Hariri |
| 2003/0187515 A1 | 10/2003 | Hariri |
| 2003/0235909 A1 | 12/2003 | Hariri |
| 2004/0028660 A1 | 2/2004 | Hariri et al. |
| 2004/0048372 A1 | 3/2004 | Hariri |
| 2004/0048796 A1 | 3/2004 | Hariri et al. |
| 2004/0171147 A1 | 9/2004 | Hariri |
| 2004/0219136 A1 | 11/2004 | Hariri |
| 2004/0241144 A1 | 12/2004 | Kaps et al. |
| 2005/0019908 A1 | 1/2005 | Hariri |
| 2005/0118715 A1 | 6/2005 | Hariri et al. |
| 2005/0143420 A1 | 6/2005 | Moutouh-de Parseval et al. |
| 2005/0148034 A1 | 6/2005 | Hariri et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2006/0060494 A1 | 3/2006 | Goodman et al. |
| 2006/0128012 A1 | 6/2006 | Arinzeh et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0038298 A1 | 2/2007 | Sulner et al. |
| 2007/0043328 A1 | 2/2007 | Goodman et al. |
| 2007/0053888 A1 | 3/2007 | Hariri |
| 2007/0092497 A1 | 4/2007 | Hariri |
| 2007/0134210 A1 | 6/2007 | Heidaran |
| 2007/0190034 A1 | 8/2007 | Paludan et al. |
| 2007/0190042 A1 | 8/2007 | Edinger et al. |
| 2007/0275362 A1 | 11/2007 | Edinger et al. |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0152624 A1 | 6/2008 | Paludan et al. |
| 2008/0152629 A1 | 6/2008 | Edinger et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213227 A1 | 9/2008 | Aggarwal et al. |
| 2008/0213228 A1 | 9/2008 | Edinger et al. |
| 2008/0226595 A1 | 9/2008 | Edinger et al. |
| 2009/0053805 A1 | 2/2009 | Hariri |
| 2009/0104164 A1 | 4/2009 | Zhang et al. |
| 2009/0126482 A1 | 5/2009 | Heidaran et al. |
| 2009/0136471 A1 | 5/2009 | Heidaran et al. |
| 2009/0142831 A1 | 6/2009 | Hariri |
| 2009/0226406 A1 | 9/2009 | Hariri |
| 2009/0252710 A1 | 10/2009 | Zhang et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0124569 A1 | 5/2010 | Abbot |
| 2010/0143312 A1 | 6/2010 | Hariri |
| 2010/0172830 A1 | 7/2010 | Heidaran |
| 2010/0183571 A1 | 7/2010 | Paludan et al. |
| 2010/0260847 A1 | 10/2010 | Hariri |
| 2010/0291679 A1 | 11/2010 | Edinger et al. |

(56) References Cited

U.S. PATENT DOCUMENTS

| | | |
|---|---|---|
| 2010/0297689 A1 | 11/2010 | Edinger et al. |
| 2010/0323446 A1 | 12/2010 | Barnett |
| 2011/0003387 A1 | 1/2011 | Abbot et al. |
| 2011/0206645 A1 | 8/2011 | Zhang et al. |
| 2011/0217271 A1 | 9/2011 | Hariri |
| 2011/0217272 A1 | 9/2011 | Hariri |
| 2011/0223141 A1 | 9/2011 | Hariri |
| 2011/0250182 A1 | 10/2011 | Abbot |
| 2011/0250185 A1 | 10/2011 | Paludan et al. |
| 2011/0280843 A1 | 11/2011 | Edinger et al. |
| 2011/0280845 A1 | 11/2011 | Edinger et al. |
| 2011/0280849 A1 | 11/2011 | Zhang et al. |
| 2011/0311491 A1 | 12/2011 | Edinger et al. |
| 2011/0318401 A1 | 12/2011 | Hariri et al. |
| 2012/0020936 A1 | 1/2012 | Hariri |
| 2012/0034195 A1 | 2/2012 | Hariri |
| 2012/0058089 A1 | 3/2012 | Hariri |
| 2012/0121550 A1 | 5/2012 | Heidaran |
| 2012/0148553 A1 | 6/2012 | Hariri et al. |

FOREIGN PATENT DOCUMENTS

| | | |
|---|---|---|
| CN | 1786154 | 6/2006 |
| EP | 0333328 | 9/1989 |
| EP | 0529751 | 3/1993 |
| EP | 0552380 | 7/1993 |
| EP | 1110957 | 6/2001 |
| EP | 1288293 A1 | 3/2003 |
| EP | 1384775 A1 | 1/2004 |
| WO | WO 1996/039101 | 12/1996 |
| WO | WO 1998/037903 | 9/1998 |
| WO | WO 1999/064566 | 12/1999 |
| WO | WO 1999/67360 | 12/1999 |
| WO | WO 2000/017325 | 3/2000 |
| WO | WO 00/69335 | 11/2000 |
| WO | WO 2000/073421 | 12/2000 |
| WO | WO 2001/021767 | 3/2001 |
| WO | WO 2002/046373 | 6/2002 |
| WO | WO 2002/063962 | 8/2002 |
| WO | WO 2002/064755 | 8/2002 |
| WO | WO 2003/042405 | 5/2003 |
| WO | WO 2003/068937 | 8/2003 |
| WO | WO 03/080833 | 10/2003 |
| WO | WO 2003/086373 | 10/2003 |
| WO | WO 2003/087333 | 10/2003 |
| WO | WO 2003/087392 | 10/2003 |
| WO | WO 2003/0102151 | 12/2003 |
| WO | WO 2004/047770 | 6/2004 |
| WO | WO 2004/071283 | 8/2004 |
| WO | WO 05/003334 | 1/2005 |
| WO | WO 2005/042703 | 5/2005 |
| WO | WO 2005/0097190 | 10/2005 |
| WO | WO 2005/055929 | 1/2006 |
| WO | WO 2006/071773 | 7/2006 |
| WO | WO 2006/122147 | 11/2006 |
| WO | WO 2007/0047465 | 4/2007 |
| WO | WO 2007/0047468 | 4/2007 |
| WO | WO 2007/079183 | 7/2007 |
| WO | WO 2008/003042 | 1/2008 |
| WO | WO 2008/0019148 | 2/2008 |
| WO | WO 2008/036374 | 3/2008 |
| WO | WO 2008/051568 | 5/2008 |
| WO | WO 2008/0100497 | 8/2008 |
| WO | WO 2012/0009422 | 1/2012 |

OTHER PUBLICATIONS

CD200, http://en.wikipedia.org/wiki/CD200 , 2007.*
Venditti et al. Enumeration of CD34+ Hematopoietic Progenitor Cells for Clinical Transplantation: Comparison of Three Different Models. Bone Marrow Transplantation, 1999, vol. 24, pp. 1019-1027.*
Musina et al. Comparison of Mesenchymal Stem Cells Obtained from Different Human Tissues. Cell Technologies in Biology and Medicine, 2005, vol. 1, No. 2, pp. 89-94.*
Kucia et al. Bone marrow as a home of heterogenous populations of nonhematopoietic stem cells. Leukemia, 2005, vol. 19, pp. 1118-1127.*
Wulf et al. Mesengenic Progenitor Cells Derived from Human Placenta. Tissue Engineering, 2004, vol. 10, pp. 1136-1147.*
Gekas et al. The placenta is a niche for hematopoietic stem cells. Developmental Cell, 2005, vol. 8, pp. 365-375.*
Pang et al. Human bone marrow hematopoietic stem cells are increased in frequency and myeloid-biased with age. PNAS, 2011, vol. 108, pp. 20012-20017.*
U.S. Appl. No. 09/659,904, filed Sep. 12, 2000, Hariri.
U.S. Appl. No. 12/187,337, filed Aug. 6, 2008, Heidaran et al.
U.S. Appl. No. 12/240,956, filed Sep. 29, 2008, Zhang et al.
U.S. Appl. No. 12/267,499, filed Nov. 7, 2008, Heidaran et al.
U.S. Appl. No. 12/544,949, filed Aug. 20, 2009, Zeitlin, et al.
U.S. Appl. No. 12/545,029, filed Aug. 20, 2009, Zeitlin, et al.
U.S. Appl. No. 12/546,556, filed Aug. 24, 2009, Abramson et al.
Abkowitz, "Can Human Hematopoietic Stem Cells Become Skin, Gut, or Liver Cells?" N. Engl. J. Med. 346(10):770-2 (2002).
Addison et al., "Metabolism of Prednisolone by the Isolated Perfused Human Placental Lobule," J. Ster. Biochem. Mol. Biol., 39(1):83-90 (1991).
Asiiiiiara et al., "Successful Peripheral Blood Stem Cell Transplantation for Myelodysplastic Syndrome," Bone Marrow Transplantation 24(12): 1343-1345 (1999).
Barry, "Where do all the placentas go?" Canadian Journal of Infection Control 9(1):8-10 (1994).
Belvedere et al., "Increased Blood Volume and CD34(+)CD38(−) Progenitor Cell Recovery Using a Novel Umbilical Cord Blood Collection System," Stem Cells 18(4):245-251 (2000).
Bersinger et al., "Effect of Late Pregnancy Serum on the Synthesis and Release of Pregnancy Proteins by the Perfused Human Term Placenta," Reprod. Fertil. Dev. 4:585-588 (1992).
Caplan, "The Mesengenic Process," Clin. Plast. Surg. 21(3):429-435 (1994).
Cardoso et al., "Release from Quiescence of CD34+ CD38− Human Umbilical Cord Blood Cells Reveals Their Potentiality to Engraft Adults," Proc. Natl. Acad. Sci. USA 90(18):8707-8711 (1993).
Chen et al., "The Potential for the Use of Mononuclear Cells from Human Umbilical Cord Blood in the Treatment of Amyotrophic Lateral Sclerosis is SOD1 Mice," J. Med. 31(1-2):21-30 (2000).
Contractor et al., "A comparison of the effects of different perfusion regimens on the structure of the isolated human placental lobule," Cell Tissue Res. 237:609-617 (1984).
Cord Blood Stem Cell, Mesh Term Database 2003.
Czarneski et al., "Effects of Cord Blood Transfer on the Hematopoietic Recovery Following Sublethal Irradiation in MRL 1pr/1pr Mice," Proc. Soc. Exp. Biol. Med. 220(2):79-87 (1999).
Dorrel "Expansion of Human Cord Blood CD34+CD38− Cells in ex vivo Culture during Retroviral Transduction without a Corresponding Increase in SCID Repopulation cell (SRC) Frequency: Dissociation of SRC Phenotype and Function," Blood 95(1):102-110 (2000).
Dushnik-Levinson et al. "Embryogenesis in vitro: study of differentiation of embryonic stem cells." Biol Neonate. 67(2):77-83 (1995).
Elchalal et al., "Postpartum Umbilical Cord Blood Collection for Transplantation: a Comparison of Three Methods," Am. J. of Obstetrics & Gyn. 182(1 Pt 1):227-232 (2000).
Emerson et al., "Ex vivo Expansion of Hematopoietic Precursors, Progenitors and Stem Cells: the Next Generation of Cellular Therapeutics," Blood 87(8):3072-3088 (1996).
Ende et al., "Human Umbilical Cord Blood Cells Amerliorate Alzheimer's Disease in Transgenic Mice, " J. Med. 32(3-4):241-7 (2001).
Ende et al., "Hemapoetic Transplantation by Means of Fetal (Cord) Blood: A New Method," Va. Med. Mon. 99:276-280 (1972).
Ende et al., "Human Umbilical Cord Blood Cells Ameliorate Huntington's Disease in Transgenic Mice," J. Med. 32(3-4):231-240 (2001).

(56) References Cited

OTHER PUBLICATIONS

Ende et al., "Human Umbilical Cord Blood Effect on SOD Mice (Amyotrophic Lateral Sclerosis)," Life Sci. 67(1):53-59 (2001).
Ende et al., "Parkinson's Disease Mice and Human Umbilical Cord Blood," Journal of Medicine 33(1-4):173-180 (2002).
Ende et al., "Pooled Umbilical Cord Blood as a Possible Universal Donor for Marrow Reconstitution and Use in Nuclear Accidents," Life Sci. 69:1531-1539 (2001).
Ende et al., "The Effect of Human Cord Blood on SJL/J Mice After Chemoablation and Irradiation and Its Possible Clinical Significance," Immunol. Invest. 24(6):999-1012 (1995).
Ende, "Berashis Cells in Human Umbilical Cord Blood Vs. Embryonic Stem Cells," J. Med. 33(1-4):167-171 (2002).
Ende, "Collection of Umbilical Cord Blood for Transplantation," Blood 80(6):1623-1624 (1992).
Ende, "The Feasibility of Using Blood Bank Stored (4° C.) Cord Blood, Unmatched for HLA for Marrow Transplantation," Am. J. Clin. Pathol. 111:773-781 (1999).
Gluckman et al., "Cord Blood Heamatopoietic Stem Cells: Biology and Transplantation," In: Hematology, American Society of Hematology Education Program Book p. 1-14. (1998).
Gluckman et al., "Results of Unrelated Umbilical Cord Blood Hematipoeietic Stem Cell Transplant," Transfusion Cinique et Biologique 8(3):146-154 (2001).
Hatzopoulos et al. "isolation and characterization of endothelial progenitor cells from mouse embryos," Development. 125(8):1457-68 (1998).
Iiimori, et al, Chemotherapeutic susceptibility of human bone marrow progenitor cells and human myelogenous leukemia cells (HL-60) in co-culture: preliminary report. Int J Cell Cloning. 2(4):254-62 (1984).
Hirashima et al. "Maturation of embryonic stem cells into endothelial cells in an in vitro model of vasculogenesis," Blood. 93(4):1253-63 (1999).
Hows, "Status of Umbilical Cord Blood Transplantation in the Year 2001," J Clin Pathol 54(6):428-434(2001).
Ilan et al., Hepatology29(2):553-562 (1999).
Ilan et al., Journal of Infectious Diseases185(2):153-161 (2002).
Kondo et al., "Reduced Interferon Gamma Production by Antigen-Stimulated Cord Blood Mononuclear Cells is a Risk Factor of Allergic Disorders—6-Year Follow-up Study," Clin. Exp. Allergy 28(11):1340-1344 (1998).
Korbling et al., "Hepatocytes and Epithelial Cells of Donor Origin in Recipients of Peripheral-Blood Stem Cells," N. Engl. J. Med. 346(10):738-746 (2002).
Kurtzberg, "Placental Bood as a Surce of Hmatopoietic Sem Cells for Transplantation into Unrelated Recipients," N. Engl. J. Med. 335:157-166 (1996).
Larsson et al., "Serum and Plasma Levels of FGF-2 and VEGF in Healthy Blood Donors," Angiogenesis 5:107-110 (2002).
Li Chang Dong et al., "Mesenchymal Stem Cells Derived from Human Placenta Suppress Allogenic Umbilical Cord Blood Lymphocyte Proliferation." Cell Res. 15: 539-547 (2005).
Lowy et al., "Isolation of transforming DNA: cloning the hamster aprt gene," Cell. 22(3):817-23 (1980).
Ma et al., "Development of an in vitro human Placenta Model by the Cultivation of Human Trophoblasts in a Fiber-Based Bioreactor System," Tissue Engineering 5:91-102 (1995).
Melchner et al., "Human Placental Conditioned Medium Reverses Apparent Commitment to Differentiation of Human Promyelocytic Leukemia Cells (HL60)," Blood 66(6):1469-1472 (1985).
Minguell et al., "Mesenchymal Stem Cells," Exp. Biol. Med. 226:507-520 (2001).
Moore et al., "A Simple Perfusion Technique for Isolation of Maternal Intervillous Blood Mononuclear Cells from Human Placentae," J. Immunol. Methods 209(1):93-104 (1997).
Muhlemann et al., "Cytomegalovirus in the Perfused Human Term Placenta in vitro," Placenta 16:367-373 (1995).
Myllynen "In Search of Models for Hepatic and Placental Pharmacokinetics," [Dissertation] University of Oulu (2003).
Nadkarni et al., "Effect of Retinoic Acid on Bone-Marrow Committed Stem Cells (CFU-c) from Chronic myeloid Leukemia Patients," Tumori. 70(6):503-505 (1984).
Nishishita, et al., "A Potential Pro-Angiogenic Cell Therapy with Human Placenta-Derived Mesenchymal Cells," Biochem. Biophys. Res. Commun. 325(1):24-31 (2004).
Ordi et al., "Massive Chronic Intervilllositis of the Placenta Associated with Malaria Infection," Am. J. Surg. Pathol. 8:1006-1011 (1998).
Papaioannou et al., "Stem Cells from Early Mammalian Embryos" Stem Cells Handbook:19-31 (2004).
Rameshwar, et al., "Endogenous Hematopoietic Reconstitution Induced by Human Umbilical Cord Blood Cells in Immunocompromised Mice: Implications for Adoptive Therapy," Experimental Hematology 27:176-185 (1999).
Reyes et al., Origin of endothelial progenitors in human postnatal bone marrow.J Clin Invest. 109(3):337-46 (2002).
Sakabe et al., "Functional Differences Between Subpopulations of Mobilized Peripheral Blood-Derived CD34+ Cells Expressing Different Levels of HLA-DR, CD33, CD38 and c-kit Antigens," Stem Cells 15(11):73-81 (1997).
Shamblott et al., "Derivation of Pluripotent Stem Cells from Cultured human Primordial Germ Cells," Proc. Natl. Acad. Sci. USA 95(23):13726-13731 (1998).
Slager, Transforming growth factor-beta in the early mouse embryo: implications for the regulation of muscle formation and implantation. Dev Genet. 14(3):212-24 (1993).
Srour, "Ex vivo Expansion of Hematopoietic Stem and Progenitor Cells. Are We There Yet?" J. Hematother. 8:93-102 (1999).
Thomson et al., Embryonic stem cell lines derived from human blastocysts. Science. 282 (5391): 1145-7 (1998).
Webster, Tissue Culture: Merriam-Webster's Online Dictionary 2004.
Turner et al., "A modified Harvest Technique for Cord Blood Hematopoietic Stem Cells," Bone Marrow Transplantation 10:89-91 (1992).
Van Bekkum, "The Pluripotent Hemopoietic Stem Cell: It's Identification and Applications," Verh. Dtsch. Ges. Patol. 74:19-24 (1990).
Viacord, Umblicical cord blood can save lives (Informational brochure), Boston: ViaCell CENTR-BRO R1 Oct. 1, 2001.
Vilmer et al., "HLA-Mismatched Cord Blood Transplantation: Immunological Studies," Blood Cells 20(2-3):235-241 (1994).
Wang et al., "Enhanced Recovery of Hematopoietic Progenitor and Stem Cells from Cultivated, Postpartum Human Placenta," Blood 98(11/1):183a Abstract No. 769 (2001).
Watanabe, et al, "Multilineage Potential of Human Placenta-Derived Mesenchymal Cells," Blood 100(11):517a, Abstract 2022 (2002).
Yan et al., Retinoic acid promotes differentiation of trophoblast stem cells to a giant cell fate.Dev Biol. 235(2):422-32 (2001).
Ye et al., "Recovery of Placental-Derived Adherent Cells with Mesenchymal Stem Cell Characteristics," Blood 98(11/1):147b Abstract No. 4260 (2001).
Notice of Allowance dated Sep. 15, 2005 in U.S. Appl. No. 10/004,942, now U.S. Pat. No. 7,045,148.
Office Action dated Dec. 16, 2004 in U.S. Appl. No. 10/004,942, now U.S. Pat. No. 7,045,148.
Office Action dated Dec. 5, 2003 in U.S. Appl. No. 10/004,942, now U.S. Pat. No. 7,045,148.
Office Action dated Jun. 15, 2004 in U.S. Appl. No. 10/004,942, now U.S. Pat. No. 7,045,148.
Office Action dated Jun. 20, 2005 in U.S. Appl. No. 10/004,942, now U.S. Pat. No. 7,045,148.
Office Action dated May 7, 2003 in U.S. Appl. No. 10/004,942, now U.S. Pat. No. 7,045,148.
Advisory Action dated Jun. 6, 2006 in U.S. Appl. No. 10/779,369.
Final Office Action dated Nov. 7, 2005 in U.S. Appl. No. 10/779,369.
Office Action dated Mar. 29, 2005 in U.S. Appl. No. 10/779,369.
Advisory Action dated Sep. 8, 2008 in U.S. Appl. No. 11/187,400.
Office Action dated Apr. 20, 2007 in U.S. Appl. No. 11/187,400.
Office Action dated Feb. 20, 2009 in U.S. Appl. No. 11/187,400.
Office Action dated Jan. 4, 2008 in U.S. Appl. No. 11/187,400.

(56) References Cited

OTHER PUBLICATIONS

Office Action dated May 22, 2008 in U.S. Appl. No. 11/187,400.
Office Action dated May 15, 2009 in U.S. Appl. No. 11/593,348.
U.S. Appl. No. 12/823,063, filed Jun. 24, 2010, Hariri.
U.S. Appl. No. 12/829,326, filed Jul. 1, 2010, Abbot.
U.S. Appl. No. 12/846,765, filed Jul. 29, 2010, Edinger et al.
U.S. Appl. No. 12/848,007, filed Jul. 30, 2010, Edinger et al.
Xu, et al., "High Sensitivity of Megakaryocytic Progenitor Cells Contained in Placental/Umbilical Cord Blood to the Stresses During Cryopreservation," Bone Marrow Transplantation 34: 537-543 (2004).
Notice of Allowance dated Jan. 10, 2011 in U.S. Appl. No. 11/648,813.
Notice of Allowance dated Feb. 18, 2011 in U.S. Appl. No. 12/341,961.
U.S. Appl. No. 13/071,437, filed Mar. 24, 2011, Zhang et al.
U.S. Appl. No. 13/089,029, filed Apr. 18, 2011, Hariri.
U.S. Appl. No. 13/081,415, filed Apr. 6, 2011, Abbot.
U.S. Appl. No. 13/081,422, filed Apr. 6, 2011, Edinger.
U.S. Appl. No. 13/107,727, filed May 13, 2011, Edinger et al.
U.S. Appl. No. 13/107,778, filed May 13, 2011, Edinger et al.
U.S. Appl. No. 13/108,871, filed May 16, 2011, Hariri.
U.S. Appl. No. 13/108,891, filed May 16, 2011, Hariri.
U.S. Appl. No. 13/108,901, filed May 16, 2011, Hariri.
U.S. Appl. No. 13/182,250, filed Jul. 13, 2011, Hariri et al.
Abe, "Therapeutic Potential of Neurotrophic Factors and Neural Stem Cells Against Ischemic Brain Injury," Journal of Cerebral Blood Flow and Metabolism, Raven Press, Ltd., New York, 20(10): 1393-1408 (2000).
BD Biosciences Human CD Marker Chart—reviewed by HLDA, published by Becton, Dickinson and Compnay (2010).
Chen, et al. "Intravaneous Administration of Human Umbilical Cord Reduces Behavioral Deficits after Stroke in Rats," Stroke 32(11): 2682-2688 (2001).
Claessens et al., "In vitro proliferation and differentiation of erythroid progenitors from patients with myelodysplastic syndromes: evidence for Fas-dependent apoptosis," Blood, 1(5):1594-1601 (2002).
Conget et al. "Phenotypical and functional properties of human bone marrow mesenchymal progenitor cells" Journal of Cellular Physiology 181:67-73 (1999).
Cosma, et al., "Use and Application of Stem Cells in Toxicology," SOT 2003 Annual Meeting, p. 4, Abstract 19.
Davila, et al., "Use and Application of Stem Cells in Toxicology," Toxicological Sciences 79:214-223 (2004).
De Coppi, , et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21, Abstract 81.
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.
De Coppi, et al., "Human fetal stem cell isolation from amniotic fluid for tissue reconstruction," J. Urology 167(4 Supp.) 85 (Abstract 338) (2002).
De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7.
Denison et al. "Cytokine secretion by human fetal membranes, decidua and placenta at term" Human Reproduction 13(12):3560-3565 (1998).
Fassas, et al., "Autologous Stem Cell Transplantation in Progressive Multiple Sclerosis—An Interim Analysis of Efficacy," J. Clin. Immunol., 20(1):24-30 (2000).
Heidaran, Disclosure Document No. 457045 for "A Method or Process for the Treatment of Degenerative Conditions or Cancer Employing Custom Fabricated Organ Tissue Grafts Using Cells Isolated, Expanded, and Stored at Birth", 15 pages, stamped by OIPE on May 28, 1999, paper dated May 13, 1999.
Hsieh et al. "Effects of glucose on placental hormones in the human term placenta in vitro" J. Formos. Med. Assoc. 96:309-313 (1997).
Jaroscak et al. "Preliminary characterization of the surface staining of placental derived adherent cells: a potential new source of stroma for umbilical cord blood (UCB) expansion," Blood 96(11, Pt 2) (2000).
Kolbus et al., "Cooperative signaling between cytokine receptors and the glucocorticoid receptor in the expansion of erythroid progenitors: molecular analysis by expression profiling," Blood, vol. 102(9):3136-46 (2003).
Lazarus, et al., "Cotransplantation of HLA-Identical Sibling Culture-Expanded Mesenchymal Stem Cells and Hematopoietic Stem Cells in Hematologic Malignancy Patients, Biol Blood Marrow Transplant," 11(5):389-398 (2005).
Malek et al. "Lack of transport of erythropoietin across the human placenta as studied by an in vitro perfusion system," European Journal of Physiology 427:157-161 (1994).
Marmont, "New Horizons in the Treatment of Autoimmune Diseases: Immunoablation and Stem Cell Transplantation," Ann. Rev. Medicine 51:115-134 (2000).
Mayani et al., "Differential effects of the hematopoietic inhibitors MIP-1 alpha, TGF-beta, and TNF-alpha on cytokine-induced proliferation of subpopulations of CD34+ cells purified from cord blood and fetal liver," Exp Hematol. 23(5):422-7 (1995).
Migliaccio et al., "In Vitro Mass Production of Human Erythroid Cells from the Blood of Normal Donors and of Thalassemic Patients," Blood Cells, Molecules, and Diseases 28(2):169-1 80 (2002).
Nagayama et al., "Immunological reconstitution after cord blood transplantation for an adult patient", Bone Marrow Transplantation 24: 211-13 (1999).
Ponticiello et al. "Gelatin-based resorbable sponge as a carrier matrix for human mesenchymal stem cells in cartilage regeneration therapy" Journal of Biomedical Materials Research 52:246-255 (2000).
Ramirez P et al., "Therapy options in imatinib failures," Oncologist 13: 424-434(2008).
Reubinoff, "Neural Progenitors from Human Embryonic Stem Cells," Nature Biotech. 19(12):1134-1140 (2001).
Ronzoni et al., "Erythroid differentiation and maturation from peripheral CD34+ cells in liquid culture: Cellular and molecular characterization," Blood Cells, Molecules, and Diseases 40 148-155 (2008).
Semenov et al. "Multipotent mesenchymal stem cells from human placenta: critical parameters for isolation and maintenance of stemness after isolation" American Journal of Obstetrics & Gynecolocy 202:193.e1-13 (2010).
Von Lindern et al., "The Glucocorticoid Receptor Cooperates With the Erythropoietin Receptorand c-Kit to Enhance and Sustain Proliferation of Erythroid Progenitors In Vitro," Blood, 94(2): 550-559 (1999).
Wiesmann, et al., "Effects of Caspase Inhibitors on Hematopoietic Engraftment After Short-Term Culture," Cell. Transplant. 11(4):351-358 (2002).
Xu et al. "Feeder-free growth of undifferentiated human embryonic stem cells" Nature Biotechnology 19:971-974 (2001).
Yen et al. "Isolation of multipotent cells from human term placenta" Stem Cells 23:3-9 (2005).
Yin et al "AC133, a novel marker for human hematopoietic stem and progenitor cells" Blood 90(12):5002-5012 (1997).
Zhao, et al., "Transplanted Human Bone Marrow-Derived Adult Stem Cells Survive and Improve Functional Outcome in a Rat Model of Cortical Ischemic Brain Injury," Experimental Neurology, Academic Press, New York, 164(2):465-466, XP001159669 (2000).
Zhao, et al., "Human Bone Marrow Stem Cells Exhibit Neural Phenotypes After Transplantation and Ameliorate Neurological Deficits with Ischemic Brain Injury in Rats," Abstract of the Annual Meeting of the Society for Neuroscience, Society of Neuroscience, Washington, DC, 26(1/02): 860.01, XP001159670 (2000).
Notice of Allowance dated Aug. 12, 2009 in U.S. Appl. No. 11/187,400.
Non-Final Office Action dated Oct. 21, 2009 in U.S. Appl. No. 11/648,804.
Final Office Action dated May 20, 2010 in U.S. Appl. No. 11/648,804.

(56) References Cited

OTHER PUBLICATIONS

Non-Final Office Action dated Apr. 21, 2011 in U.S. Appl. No. 11/648,804.
Non-Final Office Action dated Feb. 18, 2011 in U.S. Appl. No. 12/187,337.
Final Office Action dated Sep. 16, 2011 in U.S. Appl. No. 12/187,337.
Non-Final Office Action dated Jul. 1, 2011 in U.S. Appl. No. 12/829,326.
U.S. Appl. No. 13/340,528, filed Dec. 29, 2011, Abramson.
U.S. Appl. No. 13/340,550, filed Dec. 29, 2011, Abramson et al.
U.S. Appl. No. 13/340,557, filed Dec. 29, 2011, Abramson et al.
U.S. Appl. No. 13/340,589, filed Dec. 29, 2011, Abbot et al.
U.S. Appl. No. 13/473,509, filed May 16, 2012, Edinger et al.
U.S. Appl. No. 13/480,370, filed May 24, 2012, Edinger et al.
Galvin et al., "Adult Human Neural Stem Cells for Cell-Replacement Therapies in the Central Nervous System," MJA 177:316-318 (2002).
Parolini, et al., "Concise Review: Isolation and Characterization of Cells from Human Term Placenta: Outcome of the First International Workshop on Placenta Derived Stem Cells," Stem Cells 26:300-311 (2008).
Sugaya et al., "Review; Neuroreplacement Therapy and Stem Cell Biology under Disease Conditions," CMLS 60:1891-1902 (2003).
Final Office Action dated Dec. 9, 2009 in U.S. Appl. No. 11/593,348.
Office Action dated May 9, 2012 in U.S. Appl. No. 11/648,804.
Final Office Action dated Oct. 31, 2011 in U.S. Appl. No. 11/648,804.
Notice of Allowance dated Sep. 29, 2011 in U.S. Appl. No. 11/648,813.
Final Office Action dated Oct. 27, 2009 in U.S. Appl. No. 11/648,813.
Non Final Office Action dated Jun. 7, 2010 in U.S. Appl. No. 11/648,813.
Notice of Allowance dated Apr. 21, 2011 in U.S. Appl. No. 12/341,961.
Non Final Office Action dated Sep. 1, 2010 in U.S. Appl. No. 12/341,961.
Response to Office Action dated Dec. 1, 2010 in U.S. Appl. No. 12/341,961.
Final Office Action dated Jan. 3, 2012 in U.S. Appl. No. 12/829,326.
Edinger et al., "Characterization of Placenta Derived Adherent Cells (PDAC): A Novel Type of Stem Cells Isolated from Human Placenta," Blood 108(11):Abstract 1685 p. 813-I (2006).
Behring et al., "Novel Markers for the Isolation of Primary Bone Marrow Derived MSC with Multi-Lineage Differentiation Capacity," Blood 108(11):Abstract 2573 p. 751-II (2006).
Barbacheus et al., "Placenta Derived Adherent Cells (PDACs) Suppress Tumor Cells of Diverse Origin," Blood 108(11):Abstract 4813 (2006).

\* cited by examiner

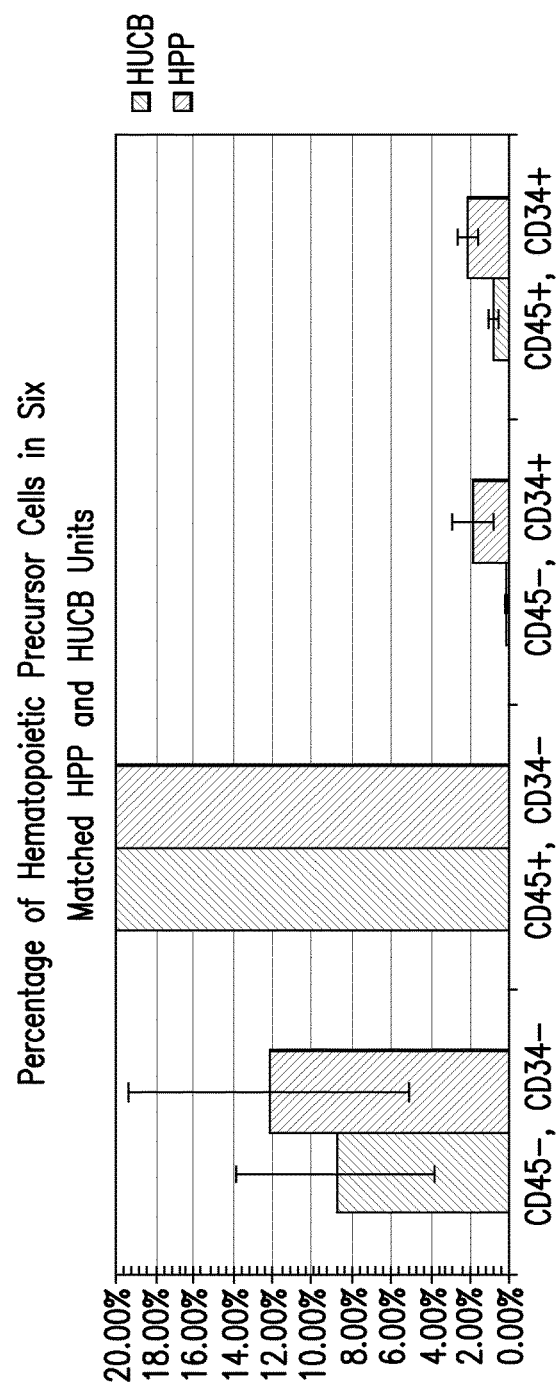

CD34$^+$,CD45$^-$ PLACENTAL STEM CELL-ENRICHED CELL POPULATIONS

This application claims benefit of U.S. Provisional Application No. 60/901,066, filed Feb. 12, 2007; U.S. Provisional Application No. 60/901,076, filed Feb. 12, 2007; U.S. Provisional Application No. 60/905,664, filed Mar. 7, 2007; U.S. Provisional Application No. 60/906,064, filed Mar. 8, 2007; and U.S. Provisional Application No. 60/966,577, filed Aug. 28, 2007, the disclosures of each of which are incorporated herein in its entirety.

1. FIELD

Provided herein are methods and compositions relating to stem cells from placenta. Provided herein are methods for the production of hepatocytes from human adherent placental stem cells, and the use of such hepatocytes in the treatment of, and intervention in, for example, trauma, inflammatory and degenerative disorders of the liver. Also provided herein are compositions and methods relating to combinations of nanofibrous scaffolds and adherent placental stem cells and methods of using the same in cartilage repair. Finally, provided herein are compositions and methods relating to nonadherent, CD34$^+$CD45$^-$ stem cells from placenta.

2. BACKGROUND

Somatic stem cells have been proposed for various therapeutic applications, including, for example, in animal models of cell replenishment therapy. The therapeutic potential of grafted stem cells can only be translated to clinical use if an ethically acceptable source of autologous stem cells is available, and if control of self renewal and fate decisions that program stem cell maturation into specific cell types is achieved.

A number of studies have described differentiation of embryonic stem cells down the hepatocyte lineage (see, e.g., Sharma, N. S. et al., *Biotechnology & Bioengineering*, 94 (6): 1053-93 (2006); Maguire, T., et al., *Biotechnology & Bioengineering*, 93(3):581-591 (2006) and Chen Y, et al., *Cell Transplant*. 2006; 15(10):865-71). In addition, human bone marrow derived mesenchymal cells were examined for the capacity to differentiate into functioning hepatocytes with some success (Ong S Y, Dai H, Leong K W, *Tissue Eng*. 2006 Oct. 1; Ong S Y, Dai H, Leong K W *Biomaterials* (22):4087-97 (2006) (epub Apr. 17, 2006); Sato Y, Araki H, Kato J, Nakamura K, *Blood*. 106(2):756-63 (2005) (epub Apr. 7, 2005).

Hepatic disorders increasingly account for significant morbidity and mortality. Destruction of liver function by environmental and pathogenic causes presents significant public health risks to otherwise healthy individuals. Replacement of damaged or killed hepatocytes in such damaged organs is therefore a significant clinical goal. However, an ethically acceptable source for stem cells that can differentiate into hepatocytes remains unavailable. These and other unmet needs are provided herein.

3. SUMMARY

In one aspect, provided herein are methods and compositions for the production of hepatocytes from adherent placental stem cells, and methods of using such hepatocytes to treat diseases, disorders or conditions, such as those involving trauma, inflammation, or systemic disorders of the liver, e.g., diseases, disorders or conditions associated with hepatic inflammation. In one embodiment, provided herein is a method of producing a hepatocyte, comprising culturing a placental stem cell under conditions and for a time sufficient for said stem cell to exhibit a characteristic of a hepatocyte. In a specific embodiment, said characteristic is the production of albumin or expression of a gene encoding albumin. In another specific embodiment, said characteristic is the production of urea. In another specific embodiment, said culturing comprises contacting said stem cell with sodium butyrate. In another specific embodiment, said culturing comprises encapsulating said stem cell in alginate-poly-L-lysine. In another embodiment, provided herein is a hepatocyte produced by differentiation of a placenta-derived stem cell. Also provided herein is a method of treating a subject having a disease, disorder or condition associated with abnormal liver function, comprising introducing such a hepatocyte into said subject. In a more specific embodiment, the disease, disorder or condition is cirrhosis of the liver. In certain embodiments, the disease or conditions results from liver toxicity caused by, e.g., alcohol or ingestion of toxins such as, e.g., mushroom toxins. In certain embodiments, the disease or condition is a viral infection, e.g., a hepatitis A, B, C, D, or E infection. In certain embodiments, the disease or condition is fulminant or subfulminant hepatitis. In another aspect, provided herein is a method for determining whether a compound has liver toxicity activity, comprising contacting a hepatocyte produced by differentiation of a placenta-derived stem cell with the compound, and determining whether the compound is toxic to the hepatocytes.

In another embodiment, the placental stem cell is positive for cytokeratin 18. In another embodiment, provided herein is a population of placental stem cells, or cells differentiated therefrom, at least 50%, 70%, 80%, 90%, 95% or 99% of which are positive for cytokeratin 18. In another embodiment, provided herein is a population of cells comprising placental stem cells, or cells differentiated therefrom, wherein at least 50%, 70%, 80%, 90%, 95% or 99% of the placental stem cells or cells differentiated therefrom are positive for cytokeratin 18. In another embodiment, the invention provides a method of isolating a placental stem cell, or population of placental stem cells, or cells differentiated therefrom, comprising selecting a cytokeratin 18$^+$ placental stem cell, or cytokeratin 18$^+$ placental stem cells, and isolating said stem cell or stem cells from other placental cells.

In another aspect, provided herein is a composition comprising a plurality of cells encapsulated in alginate, wherein said cells are differentiated from placental stem cells. In one embodiment, said cells express at least one marker of a hepatocyte not expressed by, or expressed to a detectably different degree than, a placental stem cell. In another embodiment, said alginate is in the form of beads. In a specific embodiment, said beads are from about 200 µm to about 800 µm in size. In another specific embodiment, said beads average about 500 µm in size.

In another aspect, provided herein is a mouse comprising human placental stem cell-derived hepatocytes or hepatogenic cells, wherein said mouse is produced by a method comprising the steps of: (a) irradiating said mouse with gamma radiation sufficient to kill substantially all of the endogenous bone marrow cells; (b) administering to said mouse sufficient bone marrow or bone marrow-derived cells from a NOD/SCID mouse to reconstitute the hematopoietic system of the mouse; and (c) transplanting to said mouse a plurality of hepatocytes or hepatogenic cells, wherein said hepatocytes or hepatogenic cells are differentiated from a plurality of CD10+, CD34−, CD105+, CD117−, CD200+ placental stem cells. In one embodiment, said placental stem cell is additionally cytokeratin 18+ and negative for at least one other cytokeratin expressed by differentiated hepatocytes. In another embodiment, said hepatocytes or hepatogenic cells are administered into an ear pinna of the mouse. In another embodiment, said hepatocytes or hepatogenic cells are infected with a virus. In a specific embodiment, said virus is hepatitis A virus, hepatitis B virus, hepatitis C virus, hepatitis D virus, or hepatitis E virus. In a more specific embodiment, the virus is hepatitis B virus.

In another aspect, provided herein is a method of identifying an antiviral agent, comprising contacting a mouse with a compound of interest, wherein serum from said mouse has detectable levels of virus, and wherein said compound is an antiviral agent if said contacting results in a detectable reduction in the amount of said virus in serum from said mouse, compared to serum from said mouse not contacted with the compound of interest, and wherein the mouse is produced by a method comprising the steps of: a. irradiating said mouse with gamma radiation sufficient to kill substantially all of the endogenous bone marrow cells; b. administering to said mouse sufficient bone marrow or bone marrow-derived cells from a NOD/SCID mouse to reconstitute the hematopoietic system of the mouse; and c. transplanting to said mouse a plurality of hepatocytes or hepatogenic cells, wherein said hepatocytes or hepatogenic cells are differentiated from a plurality of CD10+, CD34−, CD105+, CD117−, CD200+ placental stem cells. In one embodiment of the method, said virus is hepatitis A virus, hepatitis B virus, hepatitis C virus, hepatitis D virus, or hepatitis E virus. In specific embodiments of the method, an antigen or a nucleic acid of said virus is detected. In a more specific embodiment, said virus is hepatitis B virus. In a specific embodiment of the method, wherein a viral antigen is detected, said antigen is HBeAg or HBsAg. In another specific embodiment, wherein a viral nucleic acid is detected, said nucleic acid is the covalently closed circular form of hepatitis B virus. In a more specific embodiment, said nucleic acid is detected by PCR using primers specific for the covalently closed circular form of hepatitis B virus.

In another aspect, provided herein is a matrix, and compositions comprising such a matrix, wherein the matrix comprises placental stem cells that have differentiated in a hepatogenic or chondrogenic lineage, or to hepatocytes or chondrocytes. In a more specific embodiment, said matrix is a three-dimensional scaffold. In another more specific embodiment, said matrix comprises collagen, gelatin, laminin, fibronectin, pectin, ornithine, or vitronectin. In another more specific embodiment, said matrix is, or comprises, a nanofibrous scaffold, e.g., an electrospun nanofibrous scaffold. In a more specific embodiment, said nanofibrous scaffold comprises poly(L-lactic acid) (PLLA), type I collagen, a copolymer of vinylidene fluoride and trifluoroethylene (PVDF-TrFE), poly(-caprolactone), poly(L-lactide-co-ε-caprolactone) [P(LLA-CL)] (e.g., 75:25), and/or a copolymer of poly(3-hydroxybutyrate-co-3-hydroxyvalerate) (PHBV) and type I collagen. In another more specific embodiment, said electrospun nanofibrous scaffold promotes the differentiation of placental stem cells into chondrocytes or hepatocytes. In another specific embodiment, the electrospun nanofibrous matrix or scaffold comprises placental stem cells that have differentiated into chondrocytic cells and/or chondrocytes, or into hepatocytic cells and/or hepatocytes. In another more specific embodiment, the matrix is an amniotic membrane or an amniotic membrane-derived biomaterial. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, cytokine, antibody, or organic molecule of less than 5,000 daltons.

In another embodiment, provided herein is a composition comprising isolated adherent CD10+, CD34−, CD105+, CD200+ placental stem cells and an electrospun nanofibrous scaffold. In a specific embodiment, said nanofibrous scaffold comprises fibers of poly(L-lactic acid) (PLLA), poly lactic glycolic acid (PLGA), type I collagen, a copolymer of vinylidene fluoride and trifluoroethylene (PVDF-TrFE), poly(-caprolactone), poly(L-lactide-co-ε-caprolactone) [P(LLA-CL)] (e.g., 75:25), and/or a copolymer of poly(3-hydroxybutyrate-co-3-hydroxyvalerate) (PHBV) and type I collagen. In another specific embodiment, said nanofibrous scaffold comprises fibers that average between about 250 nanometers and about 10 μm in thickness. In another specific embodiment, said composition is contacted with conditions in which the placental stem cells differentiate into chondrogenic cells or chondrocytes. In another embodiment, provided herein is a method of making a composition comprising contacting adherent CD10+, CD34−, CD105+, CD200+ placental stem cells with an electrospun nanofibrous scaffold, wherein said nanofibrous scaffold is made by electrospinning PLLA or PLGA at about 20 kV at about 30 cm needle to collector distance and about 0.05 mL/min. to about 0.1 mL/min flow rate, wherein said PLLA or PLGA are in solution at about 10% w/w to about 20% w/w.

In another aspect, provided herein is an isolated placental stem cell that is CD34+ and CD45−. In a specific embodiment, said CD34+, CD45− stem cell is hematopoietic. In another specific embodiment, said CD34+, CD45− stem cell is non-adherent when cultured on a tissue culture surface, e.g., plastic. In a specific embodiment, provided herein is an isolated cell population enriched in placental stem cells that are CD34+ and CD45−. In specific embodiments, at least 50%, 70%, 90% or 95% of cells in said population are CD34+CD45− placental stem cells. In another specific embodiment, the isolated cell population comprises proportionately more CD34+ and CD45− placental stem cells than placental perfusate (e.g., perfusate from perfusion of a placenta with 750 mL 0.9% saline solution). In another specific embodiment, the isolated cell population comprises a stem cell that is not CD34+ and CD45−. In a more specific embodiment, said stem cell that is not CD34+ and CD45− is a CD34− adherent placental stem cell. In a more specific embodiment, said adherent placental stem cell is CD200+, CD105+, CD90+, CD10+, CD34− and/or CD45−. In another specific embodiment, said stem cell that is not CD34+ and CD45− is a bone marrow-derived mesenchymal stem cell. In another specific embodiment, said stem cell that is not CD34+ and CD45− is a CD34+, CD45+ hematopoietic stem cell. In another specific embodiment, said stem cell that is not CD34+ and CD45 is contained within cord blood or placental blood.

In another specific embodiment, the isolated cell population is a plurality of total nucleated cells (TNC) from placental perfusate. In a specific embodiment, the TNC from placental perfusate comprises placental cells from at least, or at most, 50, 100, 150, 200, 250, 300, 350, 400, 450 or 500 mL placental perfusate. In another specific embodiment, the TNC from placental perfusate have been treated to remove at least one type of non-red blood cell.

In another embodiment, the $CD34^+$, $CD45^-$ hematopoietic placental stem cells are fetal (non-maternal). In another embodiment, the $CD34^+$, $CD45^-$ hematopoietic placental stem cells are maternal. In another embodiment, an isolated population of hematopoietic placental stem cells comprises $CD34^+$, $CD45^-$ hematopoietic placental stem cells that are fetal (non-maternal). In another embodiment, an isolated population of hematopoietic placental stem cells comprises $CD34^+$, $CD45^-$ hematopoietic placental stem cells that are maternal.

In another aspect, provided herein are methods of isolating $CD34^+$, $CD45^-$ hematopoietic placental stem cells. In one embodiment, the invention provides a method of isolating a $CD34^+$, $CD45^-$ placental stem cell population, comprising selecting $CD34^+$ cells from a population of placental cells to form an isolated population of $CD34^+$ placental cells, and removing from said population of $CD34^+$ placental cells $CD45^+$ cells, wherein a $CD34^+$, $CD45^-$ placental stem cell population is produced. In a specific embodiment, said selecting $CD34^+$ cells is done by immunoseparation. In another specific embodiment, said removing $CD45^+$ cells is done by immunoseparation. In another specific embodiment, said selecting or said removing is done by flow cytometry.

In another aspect, provided herein is a method of supplementing a cell population comprising adding a plurality of $CD34^+$, $CD45^-$ hematopoietic placental stem cells to create a supplemented cell population, such that the supplemented cell population comprises substantially more $CD34^+$, $CD45^-$ cells than before said supplementing. In various specific embodiments in this context, "substantially more" means at least 1, 2, 3, 4, 5, 6, 7, 8, 9 or at least 10% more. In other specific embodiments, the cell population to be supplemented comprises cord blood, placental blood, peripheral blood, or a combination thereof. In more specific embodiments, the cell population to be supplemented is cord blood, placental blood, peripheral blood, or a combination thereof. In another more specific embodiment, the cell population to be supplemented comprises nucleated cells isolated from cord blood, placental blood, peripheral blood, or a combination thereof. In other specific embodiments, the stem cell population to be supplemented comprises a population of hematopoietic stem cells, a population of adult stem cells, or a population of embryonic stem cells.

As used herein, the term "SH2" refers to an antibody that binds an epitope on the marker CD105. Thus, cells that are referred to as $SH2^+$ are $CD105^+$.

As used herein, the terms "SH3" and "SH4" refer to antibodies that bind epitopes present on the marker CD73. Thus, cells that are referred to as $SH3^+$ and/or $SH4^+$ are $CD73^+$.

As used herein, the term "isolated stem cell" means a stem cell that is substantially separated from other, non-stem cells of the tissue, e.g., placenta, from which the stem cell is derived. A stem cell is "isolated" if at least 50%, 60%, 70%, 80%, 90%, 95%, or at least 99% of the non-stem cells with which the stem cell is naturally associated, or stem cells displaying a different marker profile, are removed from the stem cell, e.g., during collection and/or culture of the stem cell.

As used herein, the term "population of isolated cells" means a population of cells that is substantially separated from other cells of the tissue, e.g., placenta, from which the population of cells is derived. A stem cell is "isolated" if at least 50%, 60%, 70%, 80%, 90%, 95%, or at least 99% of the cells with which the population of cells, or cells from which the population of cells is derived, is naturally associated, i.e., stem cells displaying a different marker profile, are removed from the stem cell, e.g., during collection and/or culture of the stem cell.

As used herein, the term "placental stem cell" refers to a stem cell or progenitor cell, e.g., a multipotent cell, that is derived from a mammalian placenta, regardless of morphology, cell surface markers, or the number of passages after a primary culture. The term "placental stem cell" as used herein does not, however, refer to a trophoblast, cytotrophoblast, embryonic germ cell or embryonic stem cell. A cell is considered a "stem cell" if the cell retains at least one attribute of a stem cell, e.g., a marker or gene expression profile associated with one or more types of stem cells; the ability to replicate at least 10-40 times in culture; multipotency, e.g., the ability to differentiate, either in vitro, in vivo or both, into cells of one or more of the three germ layers; the lack of adult (i.e., differentiated) cell characteristics, or the like. The terms "placental stem cell" and "placenta-derived stem cell" may be used interchangeably. Unless otherwise noted herein, the term "placental" includes the umbilical cord. The adherent placental stem cells disclosed herein are, in certain embodiments, multipotent in vitro (that is, the cells differentiate in vitro under differentiating conditions), multipotent in vivo (that is, the cells differentiate in vivo), or both.

As used herein, a stem cell is "positive" for a particular marker when that marker is detectable above background. For example, a placental stem cell is positive for, e.g., CD73 because CD73 is detectable on placental stem cells, e.g., by flow cytometry, in an amount detectably greater than background (in comparison to, e.g., an isotype control). A cell is also positive for a marker when that marker can be used to distinguish the cell from at least one other cell type, or can be used to select or isolate the cell when present or expressed by the cell. In the context of, e.g., antibody-mediated detection, "positive," as an indication a particular cell surface marker is present, means that the marker is detectable using an antibody, e.g., a fluorescently-labeled antibody, specific for that marker; "positive" also means that a cell bears that marker in a amount that produces a signal, e.g., in a cytometer, that is detectably above background. For example, a cell is "$CD200^+$" where the cell is detectably labeled with an antibody specific to CD200, and the signal from the antibody is detectably higher than a control (e.g., background). Conversely, "negative" in the same context means that the cell surface marker is not detectable using an antibody specific for that marker compared to background. For example, a cell is "$CD34^-$" where the cell is not detectably labeled with an antibody specific to CD34. Unless otherwise noted herein, cluster of differentiation ("CD") markers are detected using antibodies. OCT-4 is determined to be present, and a cell is "OCT-4+" if OCT-4 is detectable using RT-PCR.

As used herein, "isolating" placental stem cells, e.g., adherent placental stem cells or $CD34^+$, $CD45^-$ stem cells, means to remove at least 20%, 30%, 40%, 50%, 60%, 70%, 80%, 90%, 95% or 99% of the cells with which the stem cells are normally associated in the intact mammalian placenta. A stem cell from an organ is "isolated" when it is present in a population of cells that comprises fewer than 50% of the cells with which the stem cell is normally associated in the intact organ. "Dim", when associated with a cell marker, indicates that the marker is present detectably above background, but within about 5% to about 10% above background.

As used herein, "hepatocyte" means a cell that appears visually, biochemically and/or by gene expression pattern to be a hepatocyte as that term is normally understood. As used herein, "hepatogenic cell," referring to a cell differentiated from a placental stem cell or umbilical cord stem cells, is a cell that displays one or more characteristics of a terminally-differentiated hepatocyte, which characteristics are not found in a placental stem cell or umbilical cord stem cells, or are not found at the same level in a placental stem cell or umbilical cord stem cell (e.g., are detectably higher or lower in a hepatogenic cell when compared to a placental stem cell or umbilical stem cell assayed for the characteristic under equivalent conditions), prior to differentiation into a hepatocyte or hepatogenic cell (e.g., a placental stem cell or umbilical cord stem cell in an expansion culture). Thus, the various compositions, methods, and other embodiments of the present application also encompass cells derived from placental stem cells that have fully or partially differentiated into hepatocytes.

4. BRIEF DESCRIPTION OF THE DRAWINGS

FIG. 1: Viability of placental stem cells from perfusion (A), amnion (B), chorion (C), or amnion-chorion plate (D), or umbilical cord stem cells (E). Numbers on X-axis designate placenta from which stem cells were obtained.

Figure 2:
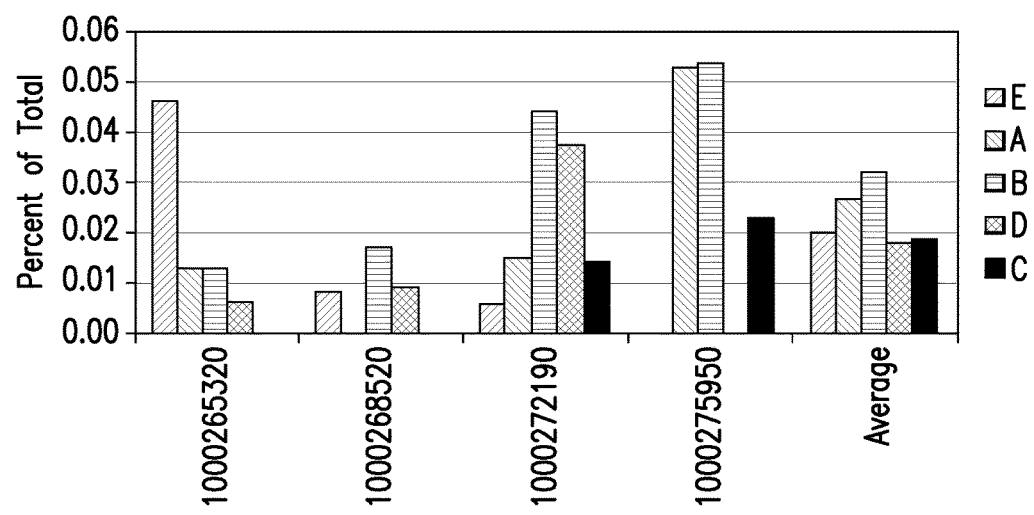

FIG. 2: Percent HLA ABC$^-$/CD45$^-$/CD34$^-$/CD133$^+$ cells from perfusion (A), amnion (B), chorion (C), or amnion-chorion plate (D), or umbilical cord stem cells (E) as determined by FACSCalibur. Numbers on X-axis designate placenta from which stem cells were obtained.

Figure 3:
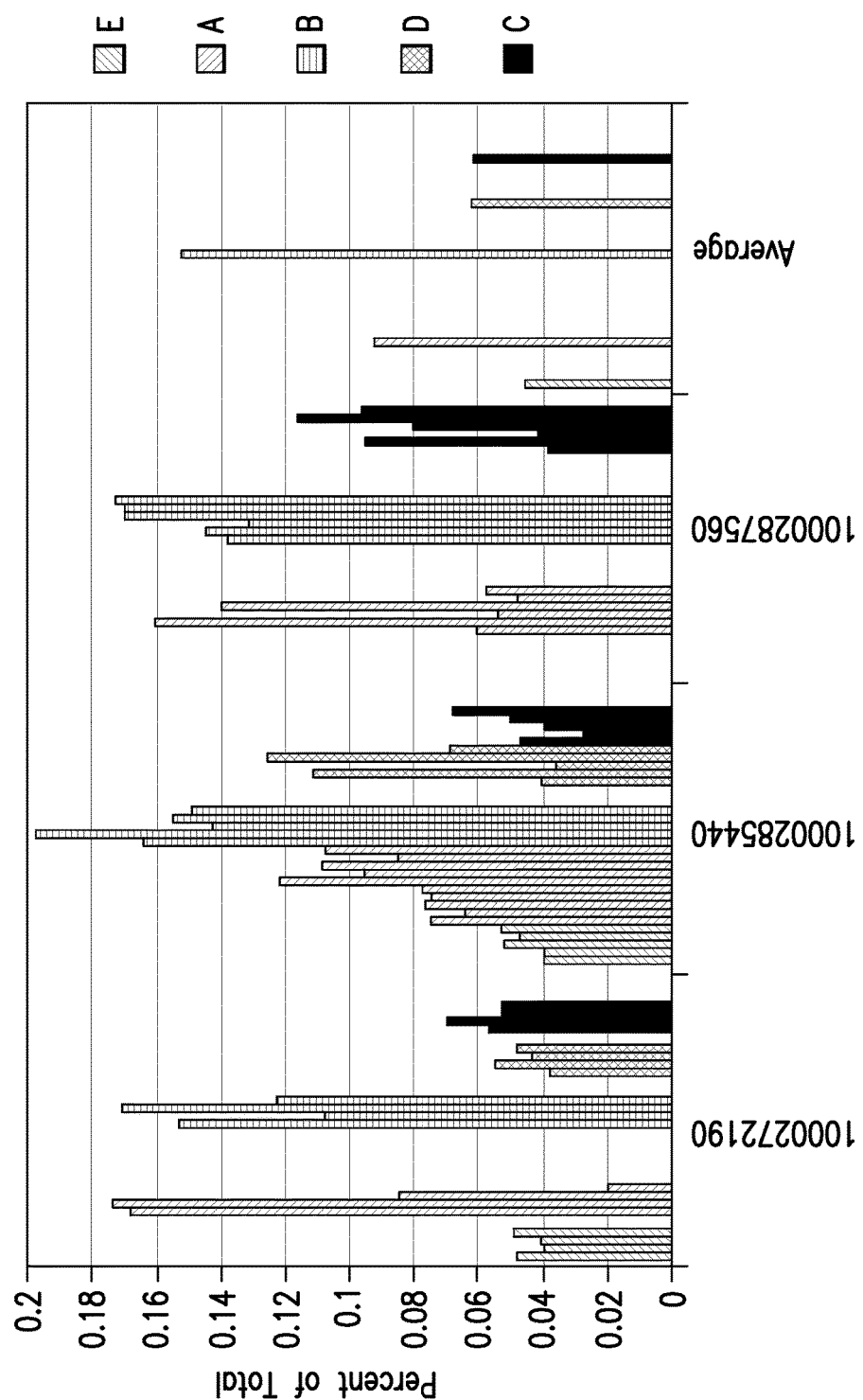

FIG. 3: Percent HLA ABC$^-$/CD45$^-$/CD34$^-$/CD133$^+$ cells from perfusion (A), amnion (B), chorion (C), or amnion-chorion plate (D), or umbilical cord stem cells (E), as determined by FACS Aria. Numbers on X-axis designate placenta from which stem cells were obtained.

Figure 4:
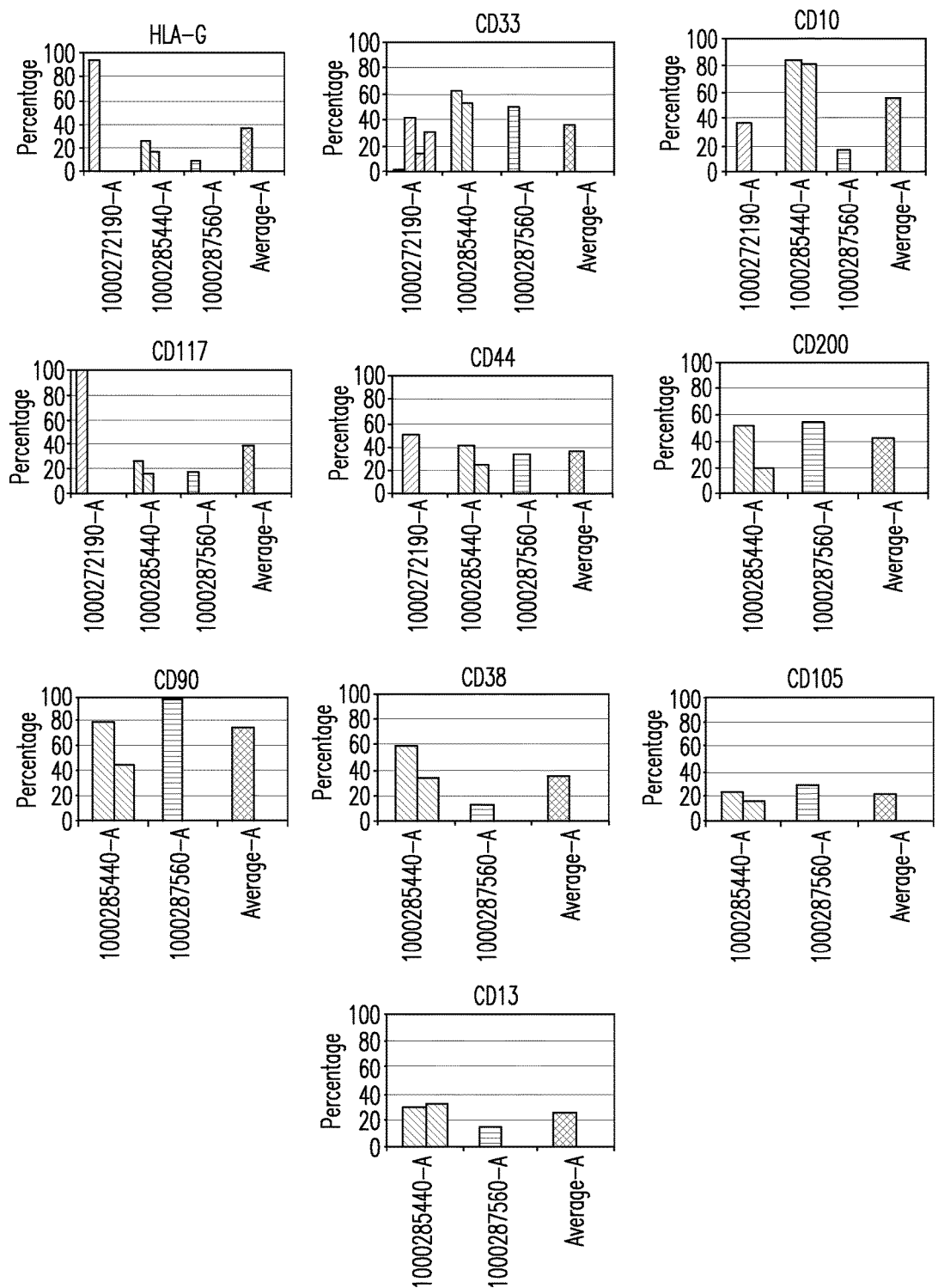

FIG. 4: HLA-G, CD10, CD13, CD33, CD38, CD44, CD90, CD105, CD117, CD200 expression in stem cells derived from placental perfusate.

Figure 5:
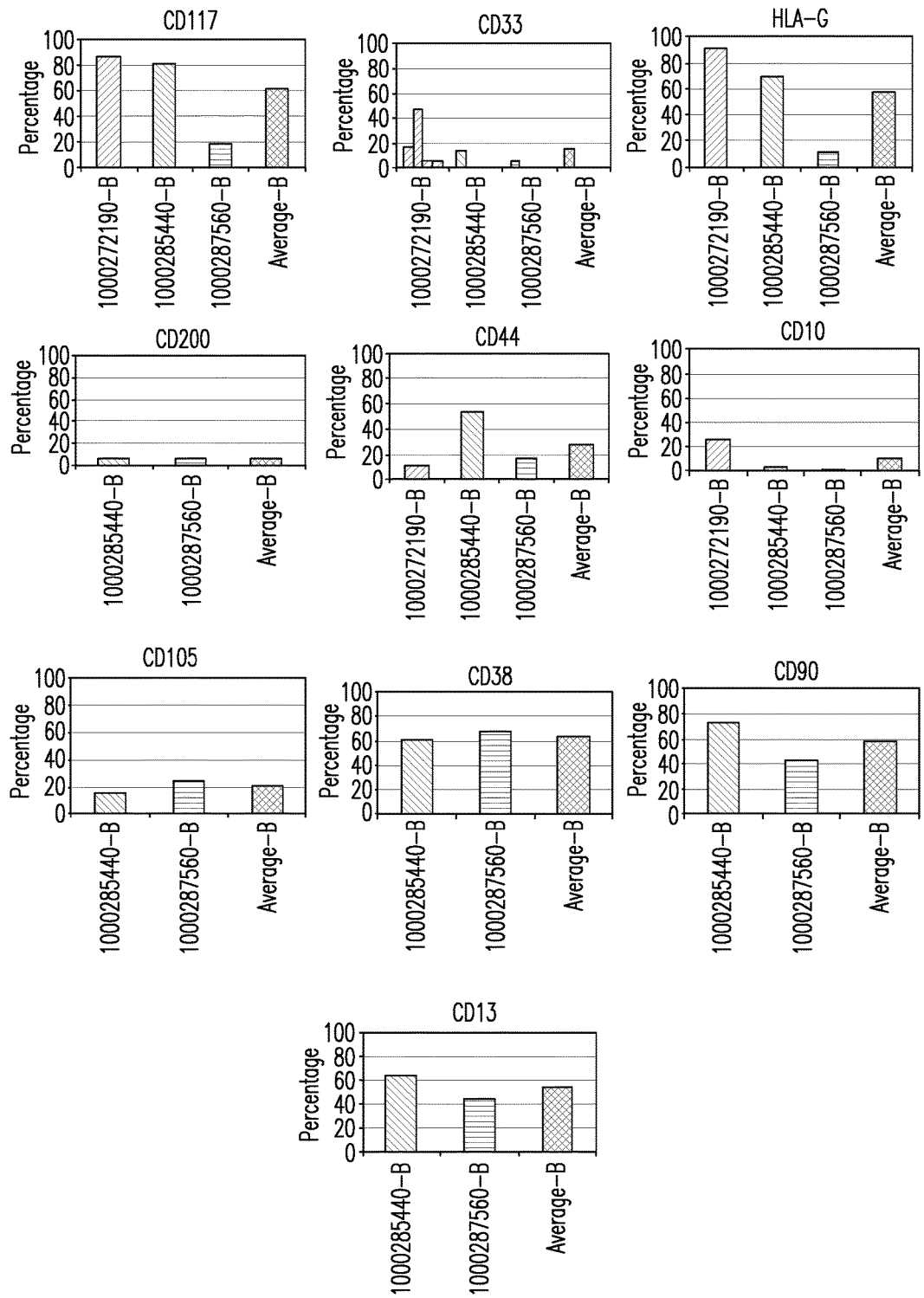

FIG. 5: HLA-G, CD10, CD13, CD33, CD38, CD44, CD90, CD105, CD117, CD200 expression in stem cells derived from amnion.

Figure 6:
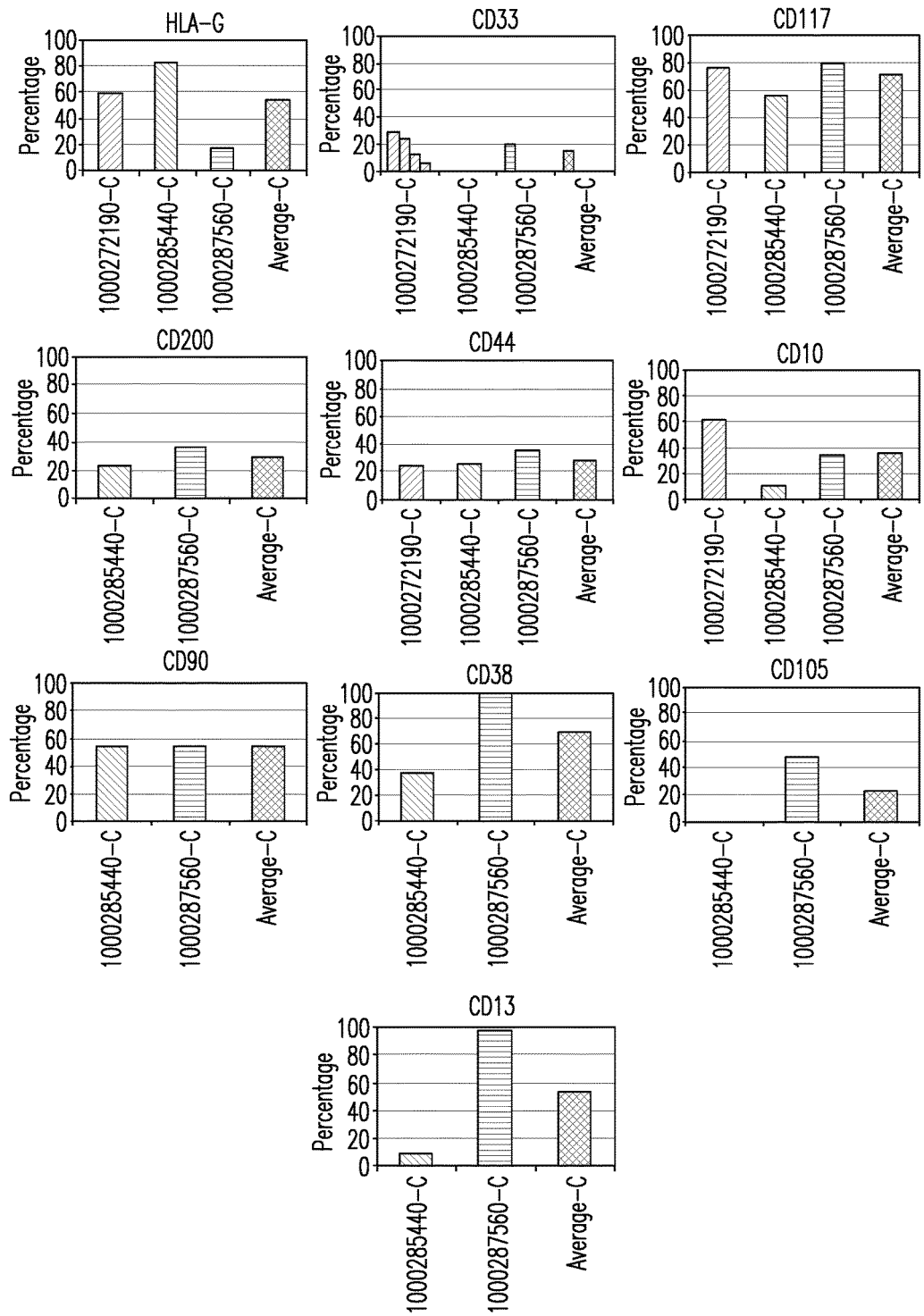

FIG. 6: HLA-G, CD10, CD13, CD33, CD38, CD44, CD90, CD105, CD117, CD200 expression in stem cells derived from chorion.

Figure 7:
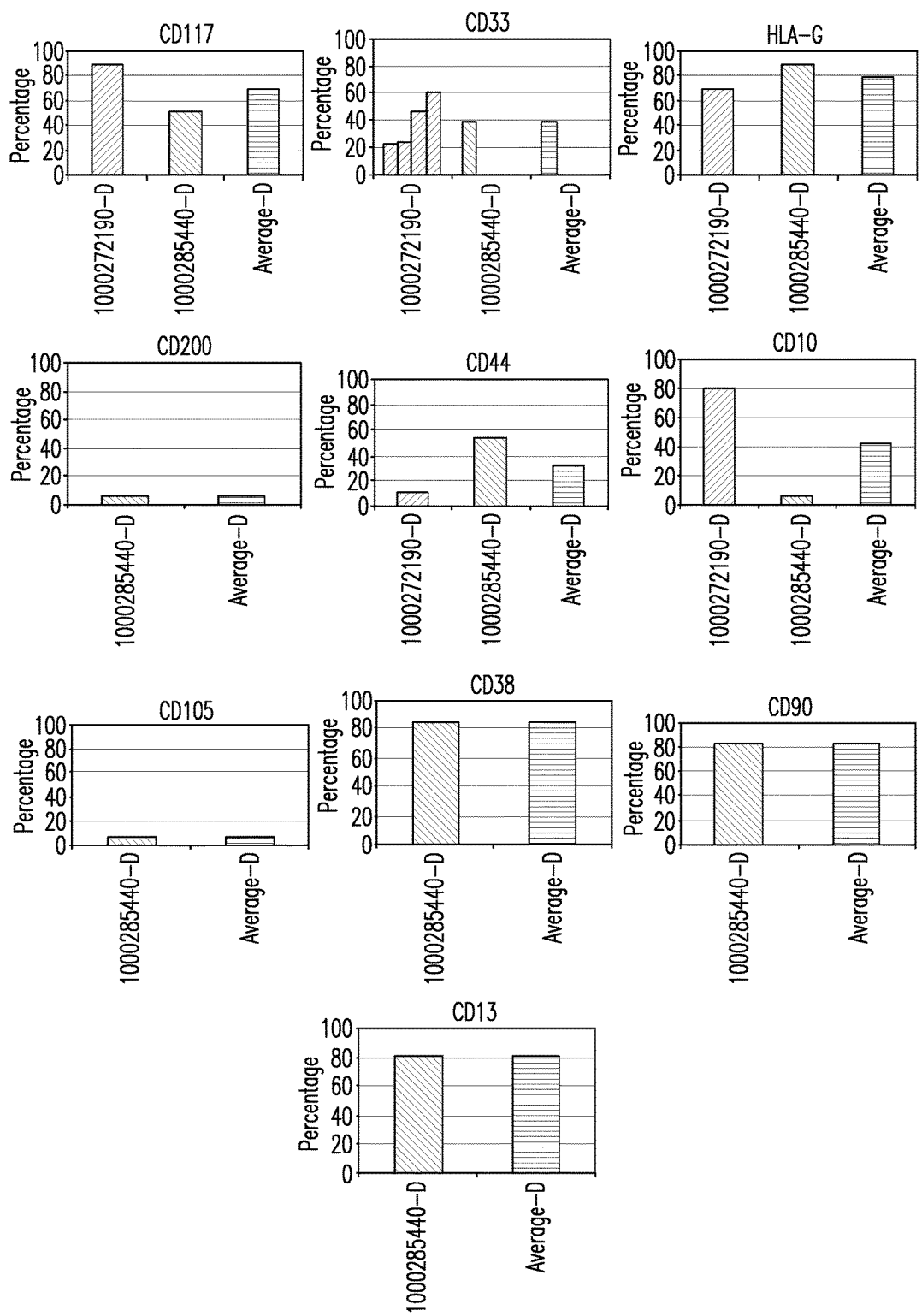

FIG. 7: HLA-G, CD10, CD13, CD33, CD38, CD44, CD90, CD105, CD117, CD200 expression in stem cells derived from amnion-chorion plate.

Figure 8:
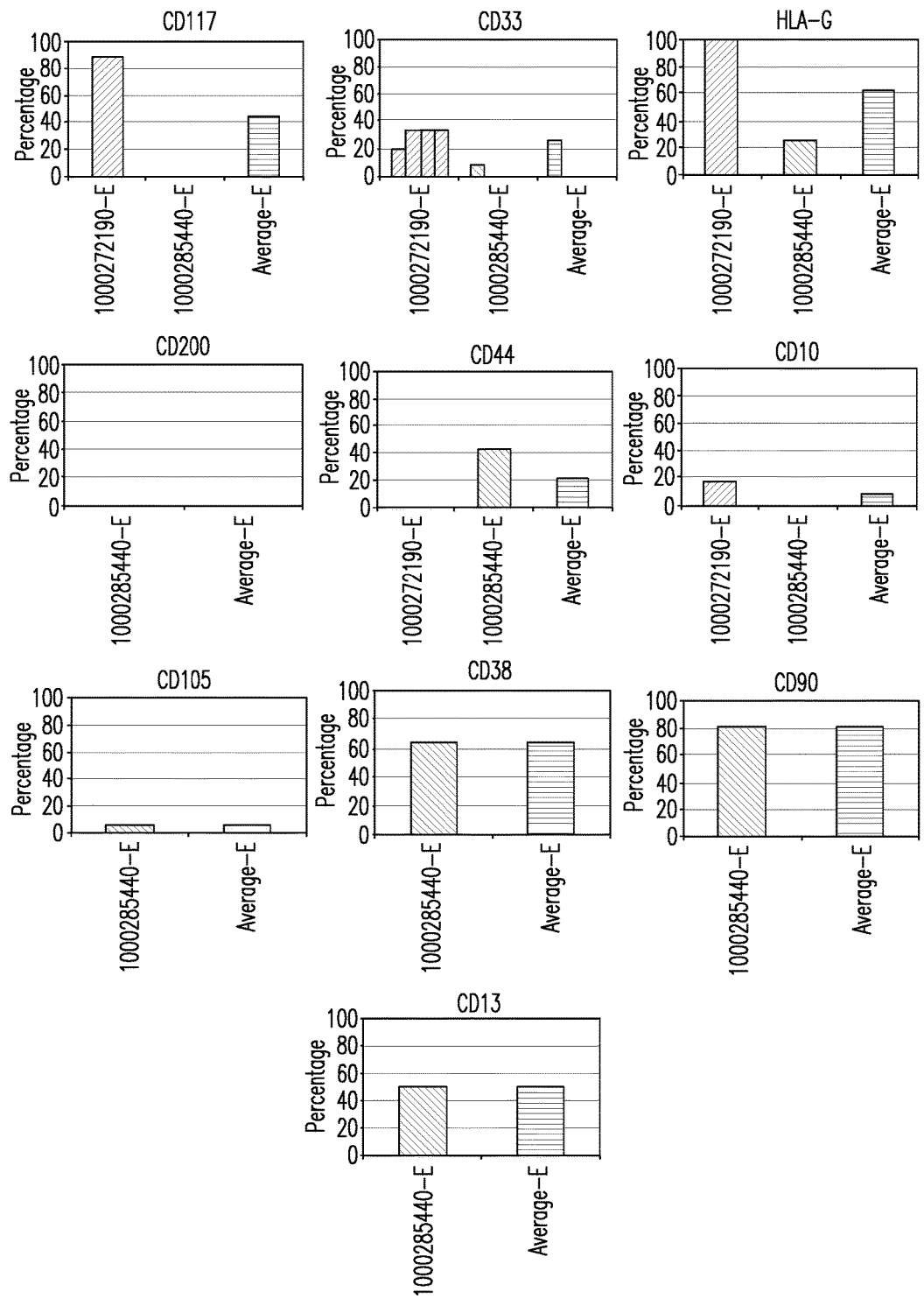

FIG. 8: HLA-G, CD10, CD13, CD33, CD38, CD44, CD90, CD105, CD117, CD200 expression in stem cells derived from umbilical cord.

Figure 9:
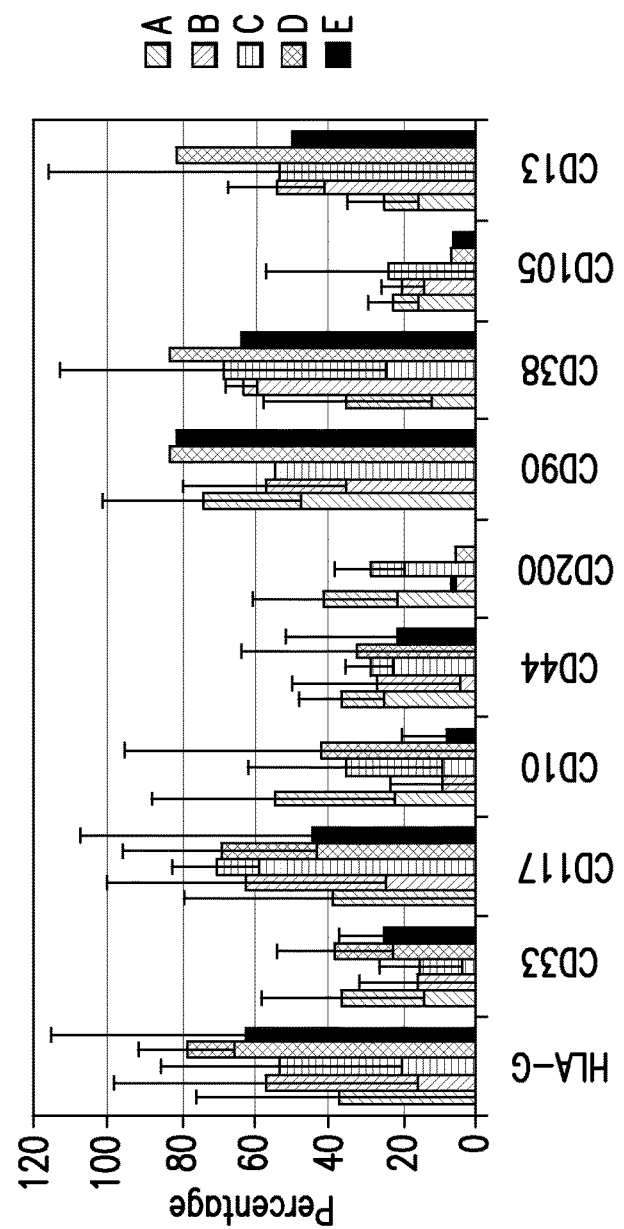

FIG. 9: Average expression of HLA-G, CD10, CD13, CD33, CD38, CD44, CD90, CD105, CD117, CD200 expression in stem cells derived from perfusion (A), amnion (B), chorion (C), amnion-chorion plate (D) or umbilical cord (E).

FIG. 10: Average percentage of total cells from six matched human placental perfusate and umbilical cord units. X axis: percent cells, of total nucleated cells, of the phenotype shown on the Y— axis.

5. DETAILED DESCRIPTION

5.1 Production of Hepatocytes

In the sections and discussions that follow, it will be understood by the skilled artisan that many of the various compositions and methods can be performed on or using placental stem cells or umbilical cord stem cells that have differentiated, or have been differentiated, down the hepatocyte lineage.

In one aspect, provided herein are methods and compositions for the production of hepatocytes and/or hepatogenic cells from placenta-derived cells, particularly placental stem cells or umbilical cord stem cells. As used herein, "placental stem cells" or "umbilical cord stem cells" means adherent stem cells unless otherwise specified. Stem cells may be obtained from a mammalian placenta or umbilical cord by perfusion (see, e.g., Hariri, U.S. Pat. Nos. 7,045,148 and 7,255,879, which are hereby incorporated herein in their entireties. Stem cells may also be obtained from placenta or umbilical cord by disruption (e.g., maceration) of a placenta or part thereof (see, e.g., Section 6.2, below). Cells displaying hepatocyte characteristics, e.g., hepatocytes and/or hepatogenic cells, may be obtained from placental stem cells. These cells are useful in the treatment of diseases, disorders or conditions associated with, for example, cirrhosis of the liver, including, but not limited to cirrhosis caused by alcohol ingestion, ingestion of hepatic toxins such as those found in, e.g., mushrooms of the genus *Amanita*, or caused by viral infections, e.g., hepatitis A, B, C, D, or E infection.

In one embodiment, differentiable cells, such as stem cells, may be obtained from the placenta or umbilical cord as follows. Primary cultures of mononuclear cells (MNCs) are isolated from placentas, e.g., from human placenta perfusates or from physically and/or enzymatically-disrupted placental tissue. The placentas are obtained following birth of full-term infants under informed consent of the donors. Briefly, for perfusion, umbilical vessels are cannulated then connected to a flow-controlled circuit, and the placenta is perfused at, e.g., 1 mL/min (room temperature, up to 24 hours) with Dulbecco's modified Eagle's medium (DMEM, Gibco/BRL) containing high glucose, 1% heparin and penicillin/streptomycin. Placenta perfusate (750 mL) is then pooled, centrifuged, and the cell pellet resuspended in PBS containing 1% fetal calf serum (FBS) then separated by differential gradient density centrifugation through LYMPHOPREP™ (Gibco/BRL). The buffy-coat interface containing mononucleated cells including adherent placental stem cells are recovered, resuspended in DMEM/10% FBS, plated on fibronectin-coated (Sigma) Falcon plates and incubated at 37° C. with 5% humidified $CO_2$. After a 24-hour incubation the nonadherent cells are discarded and the adherent cells are maintained and expanded in fresh culture media; individual cell colonies develop between 10 and 18 days and are expanded as placental stem cell lines.

Human adherent placental stem cells display fibroblast-like morphology in culture and are HLA-class I positive. Using FACS analysis these cells do not express the hematopoietic markers CD34 or CD45. However, they do express the multipotential cellular markers CD10 (CALLA), CD29 ($\beta_1$ integrin), CD54 (ICAM-1), CD90 (Thy-1) as well as SH2 (CD105), SH3 (CD73) and CD200. Under standard growth conditions the doubling time for placental stem cells is about 18 to 36 hours, and the cells maintain this phenotype for greater than 40 population doublings in vitro. Human adherent placental stem cells are distinguishable from human embryonic stem cells or embryonic germ cells in that human embryonic stem cells or germ cells are obtained only from the inner cell mass of the blastula or fetal gonads, not placentas. Human adherent placental stem cells are also distinguishable from mesenchymal stem cells from, e.g., bone marrow, cord blood or peripheral blood, or bone marrow-derived stem cells, in that placental stem cells form embryoid-like bodies in culture, while mesenchymal stem cells or bone marrow-derived stem cells do not, and placental stem cells display unique gene expression pattern relative to mesenchymal stem cells. See U.S. patent application Ser. No. 11/648,813, filed Dec. 28, 2006, the disclosure of which is hereby incorporated herein by reference in its entirety.

Placental stem cells may be differentiated to hepatocytes by culturing in culture medium comprising sodium butyrate or by encapsulating the cells in a suitable microcapsule polymer, e.g. alginate-poly-L-lysine. Hepatocytes can be produced from placenta-derived stem cells as described above, and maintained or cultured as described in below. Hepatocyte differentiation can be assessed using flow cytometry and monitoring for particular gene expression or enzymatic activity as described below.

5.2 Placental Stem Cells and Placental Stem Cell Populations

In one aspect, the methods provided herein use adherent placental stem cells, that is, stem cells obtainable from a placenta or part thereof, e.g., amnion, chorion, amnion/chorion plate, umbilical cord, etc., that (1) adhere to a tissue culture substrate; and (2) differentiate into one or more non-placental cell types, and/or cells having tissue-specific cell characteristics, under the appropriate differentiation conditions. Placental stem cells are not derived from, nor are they derivable from, blood, e.g., placental blood or umbilical cord blood, or from bone marrow.

Placental stem cells can be either fetal or maternal in origin (that is, can have the genotype of either the mother or fetus). Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by the morphological, marker, and culture characteristics discussed below.

5.2.1 Physical and Morphological Characteristics

The placental stem cells used in the methods disclosed herein, when cultured in primary culture or in cell culture, adhere to the tissue culture substrate, e.g., tissue culture container surface (e.g., tissue culture plastic). Placental stem cells in culture, e.g., on a tissue culture surface, assume a generally fibroblastoid appearance, with a number of cyotplasmic processes extending from the central cell body. The placental stem cells are, however, morphologically distinguishable from fibroblasts cultured under the same conditions, as the placental stem cells exhibit a greater number of such processes than do fibroblasts. Morphologically, placental stem cells are also distinguishable from hematopoietic stem cells, which generally assume a more rounded, or cobblestone, morphology in culture.

5.2.2 Cell Surface, Molecular and Genetic Markers

Adherent placental stem cells, and populations of adherent placental stem cells, useful in the methods and compositions described herein, express a plurality of markers that can be used to identify and/or isolate the stem cells, or populations of cells that comprise the stem cells. The placental stem cells, and stem cell populations (that is, two or more placental stem cells) described herein include stem cells and stem cell-containing cell populations obtained directly from the placenta, or any part thereof (e.g., amnion, chorion, placental cotyledons, umbilical cord, and the like). Placental stem cell populations also includes populations of (that is, two or more) placental stem cells in culture, and a population in a container, e.g., a bag. Placental stem cells are not, however, trophoblasts.

The placental stem cells described herein are multipotent in that they can be differentiated in vitro into cells representative of the three germ layers, e.g., adipocytic cells, chondrocytic cells, hepatic cells, neurogenic cells, cardiac cells, and the like. The placental stem cells described herein, however, need not differentiate in vivo to be considered multipotent, or to be useful. The term "placental stem cell," therefore, encompasses cells described herein that differentiate in vitro but not in vivo, differentiate in vivo but not in vitro, or both in vitro and in vivo. In one embodiment, the placental stem cells provided herein can be differentiated in vitro into cells representative of one or more of the three germ layers, but do not differentiate in vivo, e.g., in a NOD-SCID mouse.

Adherent (non-hematopoietic) placental stem cells generally express the markers CD73, CD105, CD200, HLA-G, and/or OCT-4, and do not express CD34, CD38, or CD45. Placental stem cells can also express HLA-ABC (MHC-1), but generally do not express HLA-DR. In a specific embodiment, adherent placental stem cells are $CD10^+$, $CD34^-$, $CD105^+$ and $CD200^+$. These markers can be used to identify placental stem cells, and to distinguish placental stem cells from other stem cell types. Because the placental stem cells can express CD73 and CD105, they can have mesenchymal stem cell-like characteristics. However, because the placental stem cells can express CD200 and HLA-G, a fetal-specific marker, they can be distinguished from mesenchymal stem cells, e.g., bone marrow-derived mesenchymal stem cells, which express neither CD200 nor HLA-G. In the same manner, the lack of expression of CD34, CD38 and/or CD45 identifies the placental stem cells as non-hematopoietic stem cells. Such placental stem cells, and populations of cells comprising such placental stem cells, can be differentiated into hepatocytes, hepatogenic cells, populations of hepatocytes, populations of hepatogenic cells, and combinations of the foregoing.

In one embodiment, the methods and compositions provided herein use an isolated placental stem cell that is $CD200^+$ and $HLA-G^+$. In specific embodiments, said stem cell is also $CD73^+$ and $CD105^+$. In another specific embodiment, said stem cell is also $CD34^-$, $CD38^-$ or $CD45^-$. In a more specific embodiment, said stem cell is also $CD34^-$, $CD38^-$, $CD45^-$, $CD73^+$ and $CD105^+$. In another specific embodiment, said stem cell has been expanded, for example, passaged at least once, at least three times, at least five times, at least 10 times, at least 15 times, or at least 20 times.

In another embodiment, the methods and compositions provided herein use an isolated cell population comprising a plurality of placental stem cells that are $CD200^+$, $HLA-G^+$. In various embodiments, at least 10%, at least 20%, at least 30%, at least 40%, at least 50% at least 60%, at least 70%, at least 80%, at least 90%, or at least 95% of said placental stem cells in said population are said $CD200^+$, $HLA-G^+$ stem cells. In a specific embodiment of the isolated populations, said stem cells are also $CD73^+$ and $CD105^+$. In another specific embodiment, said stem cells are also $CD34^-$, $CD38^-$ or $CD45^-$. In a more specific embodiment, said stem cells are also $CD34^-$, $CD38^-$, $CD45^-$, $CD73^+$ and $CD105^+$. In another embodiment, said isolated population produces one or more embryoid-like bodies when cultured under conditions that allow the formation of embryoid-like bodies. In another specific embodiment, said population has been expanded, for example, passaged at least once, at least three times, at least five times, at least 10 times, at least 15 times, or at least 20 times.

In another embodiment, the methods and compositions provided herein use an isolated placental stem cell that is CD73$^+$, CD105$^+$, CD200$^+$. In a specific embodiment of said populations, said stem cell is also HLA-G$^+$. In another specific embodiment, said stem cell is also CD34$^-$, CD38$^-$ or CD45$^-$. In another specific embodiment, said stem cell is also CD34$^-$, CD38$^-$ and CD45$^-$. In a more specific embodiment, said stem cell is also CD34$^-$, CD38$^-$, CD45$^-$, and HLA-G$^+$. In another specific embodiment, said stem cell has been expanded, for example, passaged at least once, at least three times, at least five times, at least 10 times, at least 15 times, or at least 20 times.

In another embodiment, the methods and compositions provided herein use an isolated cell population comprising a plurality of placental stem cells that are CD73$^+$, CD105$^+$, CD200$^+$. In various embodiments, at least 10%, at least 20%, at least 30%, at least 40%, at least 50% at least 60%, at least 70%, at least 80%, at least 90%, or at least 95% of said placental stem cells in said population are said CD73$^+$, CD105$^+$, CD200$^+$ cells. In a specific embodiment of said populations, said stem cells are HLA-G$^+$. In another specific embodiment, said stem cells are CD34$^-$, CD38$^-$ or CD45$^-$. In another specific embodiment, said stem cells are CD34$^-$, CD38$^-$ and CD45$^-$. In a more specific embodiment, said stem cells are CD34$^-$, CD38$^-$, CD45$^-$, and HLA-G$^+$. In another specific embodiment, said population of cells produces one or more embryoid-like bodies when cultured under conditions that allow the formation of embryoid-like bodies. In another specific embodiment, said population has been expanded, for example, passaged at least once, at least three times, at least five times, at least 10 times, at least 15 times, or at least 20 times.

In another embodiment, the methods and compositions provided herein use an isolated placental stem cell that is CD200$^+$, OCT-4$^+$. In a specific embodiment, said stem cell is also CD73$^+$ and CD105$^+$. In another specific embodiment, said stem cell is also HLA-G$^+$.

In another specific embodiment, said stem cell is also CD34$^-$, CD38$^-$ and CD45$^-$. In a more specific embodiment, said stem cell is also CD34$^-$, CD38$^-$, CD45$^-$, CD73$^+$, CD105$^+$ and HLA-G$^+$. In another specific embodiment, said stem cell has been expanded, for example, passaged at least once, at least three times, at least five times, at least 10 times, at least 15 times, or at least 20 times.

In another embodiment, the methods and compositions provided herein use an isolated cell population comprising a plurality of placental stem cells that are CD200$^+$, OCT-4$^+$. In various embodiments, at least 10%, at least 20%, at least 30%, at least 40%, at least 50% at least 60%, at least 70%, at least 80%, at least 90%, or at least 95% of said placental stem cells in said population are said CD200$^+$, OCT-4$^+$ cells. In a specific embodiment, said stem cells are CD73$^+$ and CD105$^+$. In another specific embodiment, said stem cells are HLA-G$^+$. In another specific embodiment, said stem cells are CD34$^-$, CD38$^-$ and CD45$^-$. In a more specific embodiment, said stem cells are CD34$^-$, CD38$^-$, CD45$^-$, CD73$^+$, CD105$^+$ and HLA-G$^+$. In another specific embodiment, the population produces one or more embryoid-like bodies when cultured under conditions that allow the formation of embryoid-like bodies.

In another specific embodiment, said population has been expanded, for example, passaged at least once, at least three times, at least five times, at least 10 times, at least 15 times, or at least 20 times.

In another embodiment, the methods and compositions provided herein use an isolated placental stem cell that is CD73$^+$, CD105$^+$ and HLA-G$^+$. In a specific embodiment of the above plurality, said stem cell is also CD34$^-$, CD38$^-$ or CD45$^-$. In another specific embodiment, said stem cell is also CD34$^-$, CD38$^-$ and CD45$^-$. In another specific embodiment, said stem cells are also OCT-4$^+$. In another specific embodiment, said stem cell is also CD200$^+$. In a more specific embodiment, said stem cell is also CD34$^-$, CD38$^-$, CD45$^-$, OCT-4$^+$ and CD200$^+$. In another specific embodiment, said stem cell has been expanded, for example, passaged at least once, at least three times, at least five times, at least 10 times, at least 15 times, or at least 20 times.

In another embodiment, the methods and compositions provided herein use an isolated cell population comprising a plurality of placental stem cells that are CD73$^+$, CD105$^+$ and HLA-G$^+$. In various embodiments, at least 10%, at least 20%, at least 30%, at least 40%, at least 50% at least 60%, at least 70%, at least 80%, at least 90%, or at least 95% of said placental stem cells in said population are said CD73$^+$, CD105$^+$ and HLA-G$^+$ cells. In a specific embodiment of the above plurality, said stem cells are also CD34$^-$, CD38$^-$ or CD45$^-$. In another specific embodiment, said stem cells are also CD34$^-$, CD38$^-$ and CD45$^-$. In another specific embodiment, said stem cells are also OCT-4$^+$. In another specific embodiment, said stem cells are also CD200$^+$. In a more specific embodiment, said stem cells are also CD34$^-$, CD38$^-$, CD45$^-$, OCT-4$^+$ and CD200$^+$. In another specific embodiment, said population has been expanded, for example, passaged at least once, at least three times, at least five times, at least 10 times, at least 15 times, or at least 20 times.

In another embodiment, the methods and compositions provided herein use an isolated cell population comprising a plurality of placental stem cells that are CD73$^+$, CD105$^+$ stem cells, wherein said plurality forms one or more embryoid-like bodies under conditions that allow formation of embryoid-like bodies. In various embodiments, at least 10%, at least 20%, at least 30%, at least 40%, at least 50% at least 60%, at least 70%, at least 80%, at least 90%, or at least 95% of said placental stem cells in said population are said CD73$^+$, CD105$^+$ stem cells. In a specific embodiment, said stem cells are also CD34$^-$, CD38$^-$ or CD45$^-$. In another specific embodiment, said stem cells are also CD34$^-$, CD38$^-$ and CD45$^-$. In another specific embodiment, said stem cells are also OCT-4$^+$. In a more specific embodiment, said stem cells are also OCT-4$^+$, CD34$^-$, CD38$^-$ and CD45$^-$. In another specific embodiment, said population has been expanded, for example, passaged at least once, at least three times, at least five times, at least 10 times, at least 15 times, or at least 20 times.

In another embodiment, the methods and compositions provided herein use an isolated cell population comprising a plurality of placental stem cells that are OCT-4$^+$ stem cells, wherein said population forms one or more embryoid-like bodies when cultured under conditions that allow the formation of embryoid-like bodies. In various embodiments, at least 10%, at least 20%, at least 30%, at least 40%, at least 50% at least 60%, at least 70%, at least 80%, at least 90%, or at least 95% of said placental cells in said population are said OCT4$^+$ stem cells. In a specific embodiment of the above populations, said stem cells are CD73$^+$ and CD105$^+$. In another specific embodiment, said stem cells are CD34$^-$, CD38$^-$, or CD45$^-$. In another specific embodiment, said stem cells are CD200$^+$. In a more specific embodiment, said stem cells are CD73$^+$, CD105$^+$, CD200$^+$, CD34$^-$, CD38$^-$, and CD45$^-$. In another specific embodiment, said population has been expanded, for example, passaged at least once, at least three times, at least five times, at least 10 times, at least 15 times, or at least 20 times.

In another embodiment, the methods and compositions provided herein use an isolated placental stem cell that is, or a cell population comprising a plurality of placental stem cells that are, CD29$^+$, CD44$^+$, CD73$^+$, CD90$^+$, CD105$^+$, CD200$^+$, CD34$^-$ and CD133$^-$.

In another embodiment, the methods and compositions provided herein use an isolated placental stem cell that is CD10$^+$, CD34$^-$, CD105$^+$, and CD200$^+$. Further provided herein is an isolated population of cells, e.g., placental stem cells, wherein at least about 70%, at least about 80%, at least about 90%, at least about 95% or at least about 99% of said placental stem cells are CD10$^+$, CD34, CD105$^+$, CD200$^+$. In a specific embodiment of the above embodiments, said stem cells are additionally CD90$^+$ and CD45$^-$. In a specific embodiment, said stem cell or population of placental stem cells is isolated away from placental cells that are not stem cells. In another specific embodiment, said stem cell or population of placental stem cells is isolated away from placental stem cells that do not display these characteristics. In another specific embodiment, said isolated placental stem cell is non-maternal in origin. In another specific embodiment, at least about 90%, at least about 95%, or at least about 99% of said cells in said isolated population of placental stem cells, are non-maternal in origin.

In another embodiment, the methods and compositions provided herein use an isolated placental stem cell that is HLA-A,B,C$^-$, CD45$^-$, CD133$^-$ and CD34$^-$. Further provided herein is the use of an isolated population of placental stem cells, wherein at least about 70%, at least about 80%, at least about 90%, at least about 95% or at least about 99% of said placental stem cells are HLA-A,B,C$^-$, CD45$^-$, CD133$^-$ and CD34$^-$. In a specific embodiment, said stem cell or population of placental stem cells is isolated away from placental cells that are not stem cells. In another specific embodiment, said population of placental stem cells is isolated away from placental stem cells that do not display these characteristics. In another specific embodiment, said isolated placental stem cell is non-maternal in origin. In another specific embodiment, at least about 90%, at least about 95%, or at least about 99% of said cells in said isolated population of placental stem cells, are non-maternal in origin. In another embodiment, the HLA-A,B,C$^-$, CD45$^-$, CD133$^-$ and CD34$^-$ placental stem cell is a stem cell isolated from placental perfusate. In another embodiment, the HLA-A,B,C$^-$, CD45$^-$, CD133 and CD34$^-$ placental stem cell is a stem cell isolated by physical and/or enzymatic disruption of placental tissue.

In another embodiment, the methods and compositions provided herein an isolated placental stem cell that is CD10$^+$, CD13$^+$, CD33$^+$, CD45$^-$, CD1 and CD133$^-$. Further provided herein is an isolated population of placental stem cells, wherein at least about 70%, at least about 80%, at least about 90%, at least about 95% or at least about 99% of said placental step m cells are CD10, CD13$^+$, CD33$^+$, CD45$^-$, CD117 and CD133$^-$. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least about 99% of said cells in said isolated population of placental stem cells, are non-maternal in origin. In another specific embodiment, said stem cell or population of placental stem cells is isolated away from placental stem cells that do not display these characteristics. In another embodiment, provided herein is a method of obtaining a placental stem cell that is CD10$^+$, CD13$^+$, CD33$^+$, CD45$^-$, CD117$^-$ and CD133$^-$ comprising isolating said cell from placental perfusate. In another embodiment, the HLA-A,B,C$^-$, CD45$^-$, CD133$^-$ and CD34$^-$ placental stem cell is a stem cell isolated by physical and/or enzymatic disruption of placental tissue.

In another embodiment, the methods and compositions provided herein an isolated placental stem cell that is CD10$^-$, CD33$^-$, CD44$^+$, CD45$^-$, and CD117$^-$. Further provided herein is an isolated population of placental stem cells, wherein at least about 70%, at least about 80%, at least about 90%, at least about 95% or at least about 99% of said placental stem cells are CD10$^-$, CD33$^-$, CD44$^+$, CD45$^-$, and CD117$^-$. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least 99% of said cells in said isolated population of placental stem cells, are non-maternal in origin. In another specific embodiment, said stem cell or population of placental stem cells is isolated away from placental stem cells that do not display these characteristics. In another embodiment, provided herein is a method of obtaining a placental stem cell that is CD10$^-$, CD33$^-$, CD44$^+$, CD45$^-$, CD117$^-$ comprising isolating said cell from placental perfusate. In another embodiment, the HLA-A,B, C$^-$, CD45$^-$, CD133$^-$ and CD34$^-$ placental stem cell is a stem cell isolated by physical and/or enzymatic disruption of placental tissue.

In another embodiment, the methods and compositions provided herein use an isolated placental stem cell that is CD10$^-$, CD13$^-$, CD33$^-$, CD45$^-$, and CD117$^-$. Further provided herein an isolated population of placental stem cells, wherein at least about 70%, at least about 80%, at least about 90%, at least about 95% or at least about 99% of said placental stem cells are CD10$^-$, CD13$^-$, CD33$^-$, CD45$^-$, and CD117$^-$. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least 99% of said cells in said isolated population of placental stem cells, are non-maternal in origin. In another specific embodiment, said stem cell or population of placental stem cells is isolated away from placental stem cells that do not display these characteristics. In another embodiment, provided herein is a method of obtaining a placental stem cell that is CD10$^-$, CD13$^-$, CD33$^-$, CD45$^-$, and CD117$^-$ comprising isolating said cell from placental perfusate. In another embodiment, the HLA-A,B,C$^-$, CD45$^-$, CD133$^-$ and CD34$^-$ placental stem cell is a stem cell isolated by physical and/or enzymatic disruption of placental tissue.

In another embodiment, the methods and compositions provided herein use an isolated placental stem cell that is HLA A,B,C$^-$, CD45$^-$, CD34$^-$, CD133$^-$, positive for CD10, CD13, CD38, CD44, CD90, CD105, CD200 and/or HLA-G, and/or negative for CD117. In another embodiment, the isolated population of placental stem cells used in the methods and compositions provided herein are HLA A,B, C$^-$, CD45$^-$, CD34$^-$, CD133$^-$, and at least about 20%, 25%, 30%, 35%, 40%, 45%, 50%, 55%, 60%, 65%, 70%, 75%, 80%, 85%, 90%, 95%, 98% or about 99% of the stem cells in the population are positive for CD10, CD13, CD38, CD44, CD90, CD105, CD200 and/or HLA-G, and/or negative for CD117. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least about 99%, of said cells in said isolated population of placental stem cells, are non-maternal in origin. In another specific embodiment, said stem cell or population of placental stem cells is isolated away from placental stem cells that do not display these characteristics. In another embodiment, provided herein is a method of obtaining a placental stem cell that is HLA A,B,C⁻, CD45⁻, CD34⁻, CD133⁻ and positive for CD10, CD13, CD38, CD44, CD90, CD105, CD200 and/or HLA-G, and/or negative for CD117, comprising isolating said cell from placental perfusate.

In another embodiment, the methods and compositions provided herein use a placental stem cell that is CD200⁺ and CD10⁺, as determined by antibody binding, and CD117-, as determined by both antibody binding and RT-PCR, or a population of such cells, or a population of cells comprising such isolated placental stem cells. In another embodiment, the methods and compositions provided herein use a placental stem cell that is CD10⁺, CD29⁻, CD54⁺, CD200⁺, HLA-G⁺, HLA class I⁻ and β-2-microglobulin⁻. In another embodiment, provided herein are placental stem cells, wherein the expression of at least one marker is at least two-fold higher than for a mesenchymal stem cell (e.g., a bone marrow-derived mesenchymal stem cell). In another specific embodiment, said isolated placental stem cell is non-maternal in origin. In another specific embodiment, at least about 90%, at least about 95%, or at least 99%, of said cells in said isolated population of placental stem cells, are non-maternal in origin.

In another embodiment, placental stem cells used in the methods and compositions provided herein are positive for cytokeratin 18. In another embodiment, provided herein is a population of placental stem cells, or cells differentiated therefrom, at least 50%, 70%, 80%, 90%, 95% or 99% of which are positive for cytokeratin 18. In another embodiment, provided herein is a population of cells comprising placental stem cells, or cells differentiated therefrom, wherein at least 50%, 70%, 80%, 90%, 95% or 99% of the placental stem cells or cells differentiated therefrom are positive for cytokeratin 18. In another embodiment, the invention provides a method of isolating a placental stem cell, or population of placental stem cells, or cells differentiated therefrom, comprising selecting a cytokeratin 18⁺ placental stem cell, or cytokeratin 18⁺ placental stem cells, and isolating said stem cell or stem cells from other placental cells.

In another embodiment, the methods and compositions provided herein use an isolated population of placental stem cells, wherein a plurality of said placental stem cells are positive for aldehyde dehydrogenase (ALDH), as assessed by an aldehyde dehydrogenase activity assay. Such assays are known in the art (see, e.g., Bostian and Betts, *Biochem. J.*, 173, 787, (1978)). In a specific embodiment, said ALDH assay uses ALDEFLUOR® (Aldagen, Inc., Ashland, Oreg.) as a marker of aldehyde dehydrogenase activity. In another specific embodiment, said plurality is between about 3% and about 25% of cells in said population of cells. In another embodiment, the methods and compositions provided herein use a population of placental stem cells, wherein a plurality of said placental stem cells are positive for aldehyde dehydrogenase, as assessed by an aldehyde dehydrogenase activity assay that uses ALDEFLUOR® as an indicator of aldehyde dehydrogenase activity. In a specific embodiment, said plurality is between about 3% and about 25% of cells in said population of cells. In another embodiment, said population of placental stem cells or umbilical cord stem cells shows at least three-fold, or at least five-fold, higher ALDH activity than a population of bone marrow-derived mesenchymal stem cells having the same number of cells and cultured under the same conditions.

In a specific embodiment of the above-mentioned placental stem cells, the placental stem cells constitutively secrete IL-6, IL-8 and monocyte chemoattractant protein (MCP-1).

Each of the above-referenced placental stem cells, or pluralities of placental stem cells, can comprise placental stem cells obtained and isolated directly from a mammalian placenta, or placental stem cells that have been cultured and passaged at least 1, 2, 3, 4, 5, 6, 7, 8, 9, 10, 12, 14, 16, 18, 20, 25, 30, 35, 40 or more times, or a combination thereof.

The pluralities of placental stem cells described above can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental stem cells.

5.2.3 Selecting and Producing Placental Stem Cell Populations

In another embodiment, provided herein is a method of selecting a plurality of placental stem cells from a plurality of placental cells, from which hepatocytes and/or hepatogenic cells can be differentiated, comprising selecting a population of placental cells wherein at least 10%, at least 20%, at least 30%, at least 40%, at least 50% at least 60%, at least 70%, at least 80%, at least 90%, or at least 95% of said cells are CD200⁺, HLA-G⁺ placental stem cells. In a specific embodiment, said selecting comprises selecting stem cells that are also CD73⁺ and CD105⁺. In another specific embodiment, said selecting comprises selecting stem cells that are also CD34⁻, CD38⁻ or CD45⁻. In another specific embodiment, said selecting comprises selecting placental stem cells that are also CD34⁻, CD38⁻, CD45⁻, CD73⁺ and CD105⁺. In another specific embodiment, said selecting also comprises selecting a plurality of placental stem cells that forms one or more embryoid-like bodies when cultured under conditions that allow the formation of embryoid-like bodies.

In another embodiment, provided herein is a method of selecting a plurality of placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73⁺, CD105⁺, CD200⁺ placental stem cells. In a specific embodiment, said selecting comprises selecting stem cells that are also HLA-G⁺. In another specific embodiment, said selecting comprises selecting placental stem cells that are also CD34⁻, CD38⁻ or CD45⁻. In another specific embodiment, said selecting comprises selecting placental stem cells that are also CD34⁻, CD38⁻ and CD45⁻. In another specific embodiment, said selecting comprises selecting placental stem cells that are also CD34⁻, CD38⁻, CD45⁻, and HLA-G⁺. In another specific embodiment, said selecting additionally comprises selecting a population of placental cells that produces one or more embryoid-like bodies when the population is cultured under conditions that allow the formation of embryoid-like bodies.

In another embodiment, provided herein is a method of selecting a plurality of placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD200$^+$, OCT-4$^+$ placental stem cells. In a specific embodiment, said selecting comprises selecting placental stem cells that are also CD73$^+$ and CD105$^+$. In another specific embodiment, said selecting comprises selecting placental stem cells that are also HLA-G$^+$. In another specific embodiment, said selecting comprises selecting placental stem cells that are also CD34$^-$, CD38$^-$ and CD45$^-$. In another specific embodiment, said selecting comprises selecting placental stem cells that are also CD34$^-$, CD38$^-$, CD45$^-$, CD73$^+$, CD105$^+$ and HLA-G$^+$.

In another embodiment, provided herein is a method of selecting a plurality of placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73$^+$, CD105$^+$ and HLA-G$^+$ placental stem cells. In a specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also CD200$^+$. In another specific embodiment, said selecting comprises selecting placental stem cells that are also CD34$^-$, CD38$^-$, CD45$^-$, OCT-4$^+$ and CD200$^+$.

In another embodiment, provided herein is a method of selecting a plurality of placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73$^+$, CD105$^+$ placental stem cells, and wherein said plurality forms one or more embryoid-like bodies under conditions that allow formation of embryoid-like bodies. In a specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also OCT-4$^+$. In a more specific embodiment, said selecting comprises selecting placental stem cells that are also OCT-4$^+$, CD34$^-$, CD38$^-$ and CD45$^-$.

In another embodiment, provided herein is a method of selecting a plurality of placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said isolated placental cells are OCT4$^+$ stem cells, and wherein said plurality forms one or more embryoid-like bodies under conditions that allow formation of embryoid-like bodies. In a specific embodiment, said selecting comprises selecting placental stem cells that are also CD73$^+$ and CD105$^+$. In another specific embodiment, said selecting comprises selecting placental stem cells that are also CD34$^-$, CD38$^-$, or CD45$^-$. In another specific embodiment, said selecting comprises selecting placental stem cells that are also CD200$^+$. In a more specific embodiment, said selecting comprises selecting placental stem cells that are also CD73$^+$, CD105$^+$, CD200$^+$, CD34, CD38$^-$, and CD45$^-$.

Also provided herein are methods of producing populations, or pluralities, of placental stem cells; such cells can be used in the methods and compositions provided herein. For example, provided herein is a method of producing a cell population, comprising selecting any of the pluralities of placental stem cells described above, and isolating the plurality of placental stem cells from other cells, e.g., other placental cells. In a specific embodiment, provided herein is a method of producing a cell population comprising selecting placental cells, wherein said placental cells (a) adhere to a substrate, and (b) express CD200 and HLA-G, or express CD73, CD105, and CD200, or express CD200 and OCT-4, or express CD73, CD105, and HLA-G, or express CD73 and CD105 and facilitate the formation of one or more embryoid-like bodies in a population of placental cells that comprise the stem cell, when said population is cultured under conditions that allow formation of embryoid-like bodies, or express OCT-4 and facilitate the formation of one or more embryoid-like bodies in a population of placental cells that comprise the stem cell, when said population is cultured under conditions that allow formation of embryoid-like bodies.

In a more specific embodiment, provided herein is a method of producing a cell population comprising selecting placental stem cells that (a) adhere to a substrate, and (b) express CD200 and HLA-G; and isolating said placental stem cells from other cells to form a cell population. In another specific embodiment, provided herein is a method of producing a cell population comprising selecting placental stem cells that (a) adhere to a substrate, and (b) express CD73, CD105, and CD200; and isolating said placental stem cells from other cells to form a cell population. In another specific embodiment, provided herein is a method of producing a cell population comprising selecting placental stem cells that (a) adhere to a substrate, and (b) express CD200 and OCT-4; and isolating said placental stem cells from other cells to form a cell population. In another specific embodiment, provided herein is a method of producing a cell population comprising selecting placental stem cells that (a) adhere to a substrate, (b) express CD73 and CD105, and (c) form embryoid-like bodies when cultured under conditions allowing the formation of embryoid-like bodies; and isolating said placental stem cells from other cells to form a cell population. In another specific embodiment, provided herein is a method of producing a cell population comprising selecting placental stem cells that (a) adhere to a substrate, and (b) express CD73, CD105, and HLA-G; and isolating said placental stem cells from other cells to form a cell population. A method of producing a cell population comprising selecting placental stem cells that (a) adhere to a substrate, (b) express OCT-4, and (c) form embryoid-like bodies when cultured under conditions allowing the formation of embryoid-like bodies; and isolating said placental stem cells from other cells to form a cell population.

5.2.4 Growth in Culture

The growth of the placental stem cells described herein, as for any mammalian cell, depends in part upon the particular medium selected for growth. Under optimum conditions, placental stem cells typically double in number in 3-5 days. During culture, the placental stem cells provided herein adhere to a substrate in culture, e.g. the surface of a tissue culture container (e.g., tissue culture dish plastic, fibronectin-coated plastic, and the like) and form a monolayer.

Populations of isolated placental cells that comprise the placental stem cells provided herein, when cultured under appropriate conditions, form embryoid-like bodies, that is, three-dimensional clusters of cells grow atop the adherent stem cell layer. Cells within the embryoid-like bodies are expected to express markers associated with very early stem cells, e.g., OCT-4, Nanog, SSEA3 and SSEA4. Cells within the embryoid-like bodies are typically not adherent to the culture substrate, as are the placental stem cells described herein, but remain attached to the adherent cells during culture. Embryoid-like body cells are dependent upon the adherent placental stem cells for viability, as embryoid-like bodies do not form in the absence of the adherent stem cells. The adherent placental stem cells thus facilitate the growth of one or more embryoid-like bodies in a population of placental cells that comprise the adherent placental stem cells. Without wishing to be bound by theory, the cells of the embryoid-like bodies are thought to grow on the adherent placental stem cells much as embryonic stem cells grow on a feeder layer of cells. Mesenchymal stem cells, e.g., bone marrow-derived mesenchymal stem cells, do not develop embryoid-like bodies in culture.

5.2.5 Differentiation

The placental stem cells, useful in the methods provided herein, are differentiable into different committed cell lineages. For example, the placental stem cells can be differentiated into cells of an hepatocytic lineage. Such differentiation can be accomplished, for example, by any method known in the art for differentiating, e.g., bone marrow-derived mesenchymal stem cells into similar cell lineages. See U.S. patent application Ser. No. 11/648,813, filed Dec. 28, 2006, the disclosure of which is hereby incorporated herein by reference in its entirety.

The placental stem cells to be differentiated can be contained in a polymer carrier, e.g., alginate. In one embodiment, provided herein is a composition comprising a plurality of cells encapsulated in alginate. The cells can be placental stem cells, not contacted with conditions that cause differentiation of a placental stem cell into a hepatocyte or a hepatogenic cell. The cells can also be hepatogenic cells or hepatocytes. The cells can also be a combination of any of the foregoing. Hepatogenic cells and/or hepatocytes contained within the polymer, e.g., alginate, are cells that are differentiated from placental stem cells. In one embodiment, said cells express at least one marker of a hepatocyte not expressed by, or expressed to a detectably different degree than, a placental stem cell. Preferably, the polymer, e.g., alginate, is in the form of beads that encapsulate a plurality of placental stem cells, hepatogenic cells, hepatocytes, or combination thereof. The beads can vary in size. for example, the beads can vary from about (e.g., 110%) 100 μm to about 1000 μm, between about In a specific embodiment, said beads are from about 200 μm to about 800 μm in size. In another specific embodiment, said beads average about 500 μm in size.

5.3 CD34$^+$CD45$^-$ Placental Stem Cells and Cell Populations Comprising Them

In another aspect, provided herein are isolated hematopoietic CD34$^+$, CD45$^-$ placental stem cells and/or CD34$^+$CD45$^{dim}$, placental stem cells, and isolated populations of cells enriched in CD34$^+$, CD45$^-$ placental stem cells. As used herein, "CD34$^+$CD45$^-$ placental stem cell" indicates a cell that is capable of differentiating into at least one type of mature blood cell or progenitor of a mature blood cell, which is obtained from the placenta but not from placental or umbilical cord blood, and in certain embodiments includes CD34$^+$CD45$^{dim}$ placental stem cells. The CD34$^+$, CD45$^-$ placental stem cell is detectably positive for the marker CD34, e.g., using a labeled antibody to CD34, and is dim or negative for CD45, e.g., does not label with a fluorescently-labeled antibody to CD45 such that the cell is detectable above background. CD34$^+$, CD45$^-$ placental stem cells and CD34$^+$CD45$^{dim}$ placental stem cells placental stem cells are typically non-adherent, that is, they do not adhere to a tissue culture surface.

Also provided herein are populations of placental cells enriched for CD34$^+$CD45$^-$ placental stem cells and/or CD34$^+$CD45$^{dim}$ placental stem cells. As used herein, "enriched" indicates that the placental stem cell population comprises a higher number or higher percentage of CD34$^+$CD45$^-$ cells than is found in placental perfusate, when said placental perfusate comprises about 750 mL of perfusion solution (e.g., 0.9% NaCl) passed through a human placenta at a rate of about 50 mL/min. after the placenta has been drained of cord blood and placental blood and pre-perfused with about 100 mL of perfusion solution. In a specific embodiment, CD34$^+$CD45$^-$ placental stem cells are present in a cell population at a higher percentage than found in placental perfusate, e.g., the placental stem cells constitute at least 1%, 2%, 3%, 4%, 5%, 7%, 10%, 15%, 20%, 30%, 40%, 50%, 60%, 70%, 80%, 90% or 95% of the cells in the cell population. In another specific embodiment, the stem cell population comprises about, or at least, $1 \times 10^3$, $5 \times 10^3$, $1 \times 10^4$, $5 \times 10^4$, $1 \times 10^5$, $5 \times 10^5$, $1 \times 10^6$, $5 \times 10^6$ or $1 \times 10^7$ CD34$^+$CD45$^-$ placental stem cells.

Typically, from a population of about 100 million total nucleated cells in placental perfusate, about 5% are CD34$^+$ cells, and the final yield from a placenta, taking into account viability, is about 1 million CD34$^+$ stem cells. CD34$^+$ stem cells, when collected, appear round, with low cellular complexity.

Populations of placental stem cells that comprise CD34$^+$CD45$^-$ placental stem cells can also comprise other populations of CD34$^+$ cells, for example, CD34$^+$CD38$^+$ cells and/or CD34$^+$CD38$^-$ cells. In a specific embodiment, said CD34$^+$CD38 cells comprise CD34$^+$CD38$^-$ lin$^-$ stem cells. In another specific embodiment, said CD34$^+$ placental stem cells comprise cells that are ALDH$^+$, that is, CD34$^+$, ALDH$^+$ placental stem cells.

In another embodiment, CD34$^+$, CD45$^-$ placental stem cells are combined with stem cells of a second type. In one embodiment, the stem cells of a second type comprises adherent placental stem cells that are OCT-4$^+$ or ABC$^-$ p$^+$. In another more specific embodiment, said adherent placental stem cells comprise cells that are OCT4$^+$ ABC$^-$ p$^+$. In another more specific embodiment, said hematopoietic placental stem cells are contained within placental perfusate substantially lacking red blood cells and cellular debris.

In another embodiment, the adherent placental stem cells, which are combined with the hematopoietic placental stem cells, e.g., CD34$^+$CD45$^-$ placental stem cells, comprise cells that express one or more of markers CD10, CD29, CD44, CD54, CD90, CD73 or CD105, and lack expression of one or more of markers CD34, CD38, CD45, SSEA3 and SSEA4. In another embodiment, the adherent placental stem cells comprise cells that are positive for CD10, CD29, CD44, CD54, CD90, CD73 or CD105, and negative for CD34, CD38, CD45, SSEA3 and SSEA4. In another embodiment, the adherent placental stem cells comprise cells that comprise one or more of markers CD10, CD29, CD44, CD54, CD90, CD73 and CD105, and lack one or more of markers CD34, CD38, CD45, SSEA3 and SSEA4. In another embodiment, the adherent placental stem cells comprise cells that are positive for CD10, CD29, CD44, CD54, CD90, CD73 and CD105, and negative for CD34, CD38, CD45, SSEA3 and SSEA4. In another embodiment, the adherent placental stem cells comprise CD34$^-$ cells. In a specific embodiment, the adherent placental stem cells are CD34$^-$CD38$^-$ placental stem cells. In another embodiment, the adherent placental stem cells comprise cells that are positive for at least one of CD10, CD29, CD33, CD44, CD73, CD105, CD117, and CD133, and negative for at least one of CD34 or CD45. In another embodiment, the adherent placental stem cells comprise cells that are positive for CD10, CD29, CD33, CD44, CD73, CD105, CD117, and CD133, and negative for CD34 or CD45. In a more specific embodiment, the adherent placental stem cells comprise cells that are HLA-ABC$^+$. In a more specific embodiment, the adherent placental stem cells comprise cells that are HLA-ABC$^-$. In a more specific embodiment, the adherent placental stem cells comprise cells that are HLA-DR$^+$. In a more specific embodiment, the adherent placental stem cells comprise cells that are HLA-DR$^-$. In another specific embodiment, the adherent placental stem cells comprise cells that are CD200$^+$ or HLA-G$^+$. In another specific embodiment, the adherent placental stem cells comprise cells that are CD200$^+$ and HLA-G$^+$. In another specific embodiment, the adherent placental stem cells comprise cells that are CD73$^+$, CD105$^+$ and CD200$^+$. In another specific embodiment, the adherent placental stem cells comprise cells that are CD200$^+$ and OCT-4$^+$. In another specific embodiment, the adherent placental stem cells comprise cells that are CD73$^+$, CD105$^+$ and facilitate the formation of embryoid-like bodies in a population of isolated placental cells comprising said stem cells, when said population is cultured under conditions that allow the formation of embryoid-like bodies. In another specific embodiment, the adherent placental stem cells comprise cells that are CD73$^+$, CD105$^+$ and HLA-G$^+$. In another specific embodiment, the adherent placental stem cells comprise cells that are OCT-4$^+$ and facilitate the formation of embryoid-like bodies in a population of isolated placental cells comprising said stem cells, when said population is cultured under conditions that allow the formation of embryoid-like bodies.

In another embodiment, the second population of stem cells comprises cord blood stem cells and/or bone marrow stem cells.

CD34$^+$CD45$^-$ placental stem cells and other stem cells, to be combined, may be identically HLA-matched, that is, they may be derived from the same individual. In another embodiment, the CD34$^+$CD45 placental stem cells and other stem cells may be HLA-mismatched, that is, they may be derived from different individuals. The combination of CD34$^+$CD45$^-$ placental stem cells and other stem cells can comprise stem cells that are either HLA-matched, partially HLA-matched, and/or HLA-mismatched to an intended recipient. For combined stem cell populations comprising non-cord blood stem cells, it is preferred that at least the stem cells from a second source be HLA-matched or partially HLA-matched to an intended recipient.

In various embodiments, the ratio of CD34$^+$CD45$^-$ placental stem cells to a second type of stem cell can be about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population, or comparing total numbers of stem cells in each population. In various preferred embodiments, the ratio is about 1:10 to about 10:1, or is about 3:1 to about 1:3.

Further provided herein are populations of stem cells comprising CD34$^+$CD45$^-$ placental stem cells and a second type of stem cell, wherein the population of stem cells comprises a therapeutically-effective amount of CD34$^+$CD45$^-$ placental stem cells, second type of stem cell, or both. In various combinations, the populations comprise at least 1×10$^4$, 5×10$^4$, 1×10$^5$, 5×10$^5$, 1×10$^6$, 5×10$^6$, 1×10$^7$, 5×10$^7$, 1×10$^8$, 5×10$^8$, 1×10$^9$, 5×10$^9$, 1×10$^{10}$, 5×10$^{10}$, or 1×10$^{11}$ CD34$^+$CD45$^-$ placental stem cells, second type of stem cell, or both, or no more than 1×10$^4$, 5×10$^4$, 1×10$^5$, 5×10$^5$, 1×10$^6$, 5×10$^6$, 1×10$^7$, 5×10$^7$, 1×10$^8$, 5×10$^8$, 1×10$^9$, 5×10$^9$, 1×10$^{10}$, 5×10$^{10}$, or 1×10$^{11}$ CD34$^+$CD45$^-$ placental stem cells, second type of stem cells, or both, or, alternatively, 3, 5, 10, 20, 30, 40, or 50 units or more, of total nucleated cells, from both the placental stem cell population and the second type of stem cell.

5.4 Methods of Obtaining Placental Stem Cells 5.4.1 Stem Cell Collection Composition The placental stem cells, e.g., adherent placental stem cells and/or CD34$^+$, CD45$^-$ placental stem cells, used in the methods and compositions provided herein can be collected by any means known in the art for collecting cells from tissue, e.g., by perfusion of a placenta and/or by physical and/or enzymatic disruption of placental tissue. Generally, stem cells are obtained from a mammalian placenta using a physiologically-acceptable solution, e.g., a stem cell collection composition. A stem cell collection composition is described in detail in related U.S. Application Publication No. 2007/0190042, entitled "Improved Composition for Collecting Placental Stem Cells and Preserving Organs" filed on Dec. 28, 2006.

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The stem cell collection composition can comprise one or more components that tend to preserve placental stem cells, that is, prevent the placental stem cells from dying, or delay the death of the placental stem cells, reduce the number of placental stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, a hyaluronidase, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., *Pseudomonas aeruginosa, Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 µM to about 100 µM); a reducing agent (e.g., N-acetylcysteine present at about 0.1 mM to about 5 mM); an agent that prevents calcium entry into cells (e.g., verapamil present at about 2 µM to about 25 µM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 µM to about 5 µM).

5.4.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental stem cells can be used, in light of the medical history, for personalized medicine for the infant associated with the placenta, or for parents, siblings or other relatives of the infant.

Prior to recovery of placental stem cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifebankUSA, Cedar Knolls, N.J.; ViaCord; Cord Blood Registry; Cryocell; and the like. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in U.S. Pat. No. 7,147,626 or in United States Patent Application Publication No. 2006/0060494. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to stem cell collection, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5° C. to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental stem cells are collected.

The mammalian placenta or a part thereof, once collected and prepared generally as above, can be treated in any art-known manner, e.g., can be perfused or disrupted, e.g., digested with one or more tissue-disrupting enzymes, to obtain stem cells.

5.4.3 Physical Disruption and Enzymatic Digestion of Placental Tissue

In one embodiment, stem cells are collected from a mammalian placenta by physical disruption, e.g., enzymatic digestion, of the organ. For example, the placenta, or a portion thereof, may be, e.g., crushed, sheared, minced, diced, chopped, macerated or the like, while in contact with the stem cell collection composition described herein, and the tissue subsequently digested with one or more enzymes. The placenta, or a portion thereof, may also be physically disrupted and digested with one or more enzymes, and the resulting material then immersed in, or mixed into, the stem cell collection composition described herein. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

The placenta can be dissected into components prior to physical disruption and/or enzymatic digestion and stem cell recovery. For example, placental stem cells can be obtained from all or a portion of the amniotic membrane, chorion, placental cotyledons, or any combination thereof. Preferably, placental stem cells are obtained from placental tissue comprising amnion and chorion. Typically, placental stem cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume.

A preferred stem cell collection composition comprises one or more tissue-disruptive enzyme(s). Enzymatic digestion preferably uses a combination of enzymes, e.g., a combination of a matrix metalloprotease and a neutral protease, for example, a combination of collagenase and dispase. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Any combination of tissue digestion enzymes can be used. Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental stem cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the stem cells with the stem cell collection composition.

It will be appreciated that where an entire placenta, or portion of a placenta comprising both fetal and maternal cells (for example, where the portion of the placenta comprises the chorion or cotyledons), the placental stem cells collected will comprise a mix of placental stem cells derived from both fetal and maternal sources. Where a portion of the placenta that comprises no, or a negligible number of, maternal cells (for example, amnion), the placental stem cells collected will comprise almost exclusively fetal placental stem cells.

5.4.4 Placental Perfusion

Placental stem cells useful in the methods and compositions provided herein can also be obtained by perfusion of the mammalian placenta. Methods of perfusing mammalian placenta to obtain stem cells are disclosed, e.g., in Hariri, U.S. Pat. Nos. 7,045,148 and 7,255,879, and in U.S. Application Publication No. 2007/0190042, entitled "Improved Composition for Collecting and Preserving Organs."

Placental stem cells can be collected by perfusion, e.g., through the placental vasculature, using, e.g., a stem cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid, e.g., a stem cell collection composition as provided herein, through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins, that is, is passed through only the placental vasculature (fetal tissue). This can be referred to as the "closed circuit" method of perfusion. The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain stem cells by enzymatic digestion, or to produce, e.g., an amniotic membrane biomaterial, e.g., the biomaterial described in U.S. Application Publication No. 2004/0048796. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate are then collected, e.g., by centrifugation.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 mL of perfusion fluid is adequate to initially exsanguinate the placenta, but more or less perfusion fluid may be used depending on the observed results.

The volume of perfusion liquid used to collect placental stem cells may vary depending upon the number of stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the stem cell collection composition, or a standard perfusion solution (e.g., a normal saline solution such as phosphate buffered saline ("PBS") with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 μg/ml), penicillin (e.g., at 40 U/ml), amphotericin B (e.g., at 0.5 μg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of cells, e.g., stem cells. Perfusates from different time points can also be pooled.

Without wishing to be bound by any theory, after exsanguination and a sufficient time of perfusion of the placenta, placental stem cells are believed to migrate into the exsanguinated and perfused microcirculation of the placenta where, according to the methods described herein, they are collected, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Perfusion according to the methods described herein typically results in the collection of significantly more placental stem cells than the number obtainable from a mammalian placenta not perfused with said solution, and not otherwise treated to obtain stem cells (e.g., by tissue disruption, e.g., enzymatic digestion). In this context, "significantly more" means at least 10% more. Perfusion as described herein yields significantly more placental stem cells than, e.g., the number of placental stem cells obtainable from culture medium in which a placenta, or portion thereof, has been cultured.

Stem cells can be isolated from placenta by perfusion with a solution comprising one or more proteases or other tissue-disruptive enzymes. In a specific embodiment, a placenta or portion thereof (e.g., amniotic membrane, amnion and chorion, placental lobule or cotyledon, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The stem cells are washed after several minutes with a cold (e.g., 4° C.) stem cell collection composition.

It will be appreciated that perfusion using the pan method, that is, whereby perfusate is collected after it has exuded from the maternal side of the placenta, results in a mix of fetal and maternal cells. As a result, the cells collected by this method comprise a mixed population of placental stem cells of both fetal and maternal origin. In contrast, perfusion solely through the placental vasculature, whereby perfusion fluid is passed through one or two placental vessels and is collected solely through the remaining vessel(s), results in the collection of a population of placental stem cells almost exclusively of fetal origin.

5.4.5 Isolation, Sorting, and Characterization of Placental Stem Cells

Stem cells from mammalian placenta, whether obtained by perfusion or enyzmatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using LYMPHOPREP™ (Nycomed Pharma, Oslo, Norway) according to the manufacturer's recommended procedure.

As used herein, "isolating" placental stem cells means to remove at least 20%, 30%, 40%, 50%, 60%, 70%, 80%, 90%, 95% or 99% of the cells with which the stem cells are normally associated in the intact mammalian placenta. A stem cell from an organ is "isolated" when it is present in a population of cells that comprises fewer than 50% of the cells with which the stem cell is normally associated in the intact organ.

Placental cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental stem cells typically detach from plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex). In one embodiment of isolation of adherent cells, aliquots of, for example, about 5–10×10$^6$ cells are placed in each of several T-75 flasks, preferably fibronectin-coated T75 flasks. In such an embodiment, the cells can be cultured with commercially available Mesenchymal Stem Cell Growth Medium (MSCGM™) (Cambrex), and placed in a tissue culture incubator (37° C., 5% $CO_2$). After 10 to 15 days, non-adherent cells are removed from the flasks by washing with PBS. The PBS is then replaced by MSCGM™. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34; if so, the cell is CD34$^+$. Likewise, if a cell produces enough OCT-4 RNA to be detectable by RT-PCR, or significantly more OCT-4 RNA than an adult cell, the cell is OCT-4$^+$ Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, *Methods Enzymol*, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, stem cells from placenta are sorted on the basis of expression of the markers CD34, CD38, CD44, CD45, CD73, CD105, CD117, CD200, OCT-4 and/or HLA-G. This can be accomplished in connection with procedures to select stem cells on the basis of their adherence properties in culture. For example, an adherence selection stem can be accomplished before or after sorting on the basis of marker expression. In one embodiment, for example, cells are sorted first on the basis of their expression of CD34; CD34$^-$ cells are retained, and cells that are CD200$^+$HLA-G$^+$ are separated from all other CD34$^-$ cells. In another embodiment, cells from placenta are based on their expression of markers CD200 and/or HLA-G; for example, cells displaying either of these markers are isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental cells are sorted by expression, or lack thereof, of CD200, HLA-G, CD73, CD105, CD34, CD38 and CD45, and placental cells that are CD200$^+$, HLA-G$^+$, CD73$^+$, CD105$^+$, CD34, CD38$^-$ and CD45$^-$ are isolated from other placental cells for further use.

With respect to antibody-mediated detection and sorting of placental stem cells, any antibody, specific for a particular marker, can be used, in combination with any fluorophore or other label suitable for the detection and sorting of cells (e.g., fluorescence-activated cell sorting). Antibody/fluorophore combinations to specific markers include, but are not limited to, fluorescein isothiocyanate (FITC) conjugated monoclonal antibodies against HLA-G (available from Serotec, Raleigh, N.C.), CD10 (available from BD Immunocytometry Systems, San Jose, Calif.), CD44 (available from BD Biosciences Pharmingen, San Jose, Calif.), and CD105 (available from R&D Systems Inc., Minneapolis, Minn.); phycoerythrin (PE) conjugated monoclonal antibodies against CD44, CD200, CD117, and CD13 (BD Biosciences Pharmingen); phycoerythrin-Cy7 (PE Cy7) conjugated monoclonal antibodies against CD33 and CD10 (BD Biosciences Pharmingen); allophycocyanin (APC) conjugated streptavidin and monoclonal antibodies against CD38 (BD Biosciences Pharmingen); and Biotinylated CD90 (BD Biosciences Pharmingen). Other antibodies that can be used include, but are not limited to, CD133-APC (Miltenyi), KDR-Biotin (CD309, Abcam), CytokeratinK-Fitc (Sigma or Dako), HLA ABC-Fitc (BD), HLA DRDQDP-PE (BD), β-2-microglobulin-PE (BD), CD80-PE (BD) and CD86-APC (BD).

Other antibody/label combinations that can be used include, but are not limited to, CD45-PerCP (peridin chlorophyll protein); CD44-PE; CD19-PE; CD10-F (fluorescein); HLA-G-F and 7-amino-actinomycin-D (7-AAD); HLA-ABC-F; and the like.

Placental stem cells can be assayed for CD117 or CD133 using, for example, phycoerythrin-Cy5 (PE Cy5) conjugated streptavidin and biotin conjugated monoclonal antibodies against CD117 or CD133; however, using this system, the cells can appear to be positive for CD117 or CD133, respectively, because of a relatively high background.

Placental stem cells can be labeled with an antibody to a single marker and detected and/sorted. Placental stem cells can also be simultaneously labeled with multiple antibodies to different markers.

In another embodiment, magnetic beads can be used to separate cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental stem cells can also be characterized and/or sorted based on cell morphology and growth characteristics.

For example, placental stem cells can be characterized as having, and/or selected on the basis of, e.g., a fibroblastoid appearance in culture. Placental stem cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture are isolated from other placental cells. In another embodiment, OCT-4⁺ placental cells that produce one or more embryoid-like bodies in culture are isolated from other placental cells.

In another embodiment, placental stem cells can be identified and characterized by a colony forming unit assay. Colony forming unit assays are commonly known in the art, such as MESENCULT® medium (Stem Cell Technologies, Inc., Vancouver British Columbia)

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (ATCC; to assess proliferation). Longevity may be determined by methods well known in the art, such as by determining the maximum number of population doubling in an extended culture.

Placental stem cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.5 Culture of Placental Stem Cells 5.5.1 Culture Media

Isolated placental stem cells, or placental stem cell population, or cells or placental tissue from which placental stem cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL (BD Discovery Labware, Bedford, Mass.)).

Placental stem cells can be cultured in any medium, and under any conditions, recognized in the art as acceptable for the culture of stem cells. Preferably, the culture medium comprises serum. Placental stem cells can be cultured in, for example, DMEM-LG (Dulbecco's Modified Essential Medium, low glucose)/MCDB201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GLUTAMAX™ and gentamicin; DMEM comprising 10% FBS, GLUTAMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media that can be used to culture placental stem cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE™.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; one or more antibiotic and/or antimycotic agents to control microbial contamination, such as, for example, penicillin G, streptomycin sulfate, amphotericin B, gentamicin, and nystatin, either alone or in combination; and one or more neuroectoderm specification factors, for example, sonic hedgehog (shh) and/or retinoic acid (ra).

Placental stem cells can be cultured in standard tissue culture conditions, e.g., in tissue culture dishes or multiwell plates. Placental stem cells can also be cultured using a hanging drop method. In this method, placental stem cells are suspended at about 1×10⁴ cells per mL in about 5 mL of medium, and one or more drops of the medium are placed on the inside of the lid of a tissue culture container, e.g., a 100 mL Petri dish. The drops can be, e.g., single drops, or multiple drops from, e.g., a multichannel pipetter. The lid is carefully inverted and placed on top of the bottom of the dish, which contains a volume of liquid, e.g., sterile PBS sufficient to maintain the moisture content in the dish atmosphere, and the stem cells are cultured.

In one embodiment, the placental stem cells are cultured in the presence of a compound that acts to maintain an undifferentiated phenotype in the placental stem cell. In a specific embodiment, the compound is a substituted 3,4-dihydropyridimol[4,5-d]pyrimidine. In a more specific embodiment, the compound is a compound having the following chemical structure:

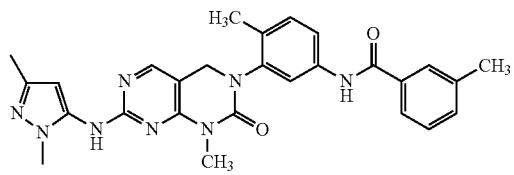

The compound can be contacted with a placental stem cell, or population of placental stem cells, at a concentration of, for example, between about 1 μM to about 10 μM.

5.5.2 Expansion and Proliferation of Placental Stem Cells

Once an isolated placental stem cell, or isolated population of stem cells (e.g., a stem cell or population of stem cells separated from at least 50% of the placental cells with which the stem cell or population of stem cells is normally associated in vivo), the stem cell or population of stem cells can be proliferated and expanded in vitro. For example, a population of placental stem cells can be cultured in tissue culture containers, e.g., dishes, flasks, multiwell plates, or the like, for a sufficient time for the stem cells to proliferate to 70-90% confluence, that is, until the stem cells and their progeny occupy 70-90% of the culturing surface area of the tissue culture container.

Placental stem cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Placental stem cells preferably are grown under low oxidative stress (e.g., with addition of glutathione, ascorbic acid, catalase, tocopherol, N-acetylcysteine, or the like).

Once 70%-90% confluence is obtained, the cells may be passaged. For example, the cells can be enzymatically treated, e.g., trypsinized, using techniques well-known in the art, to separate them from the tissue culture surface. After removing the cells by pipetting and counting the cells, about 20,000-100,000 stem cells, preferably about 50,000 stem cells, are passaged to a new culture container containing fresh culture medium. Typically, the new medium is the same type of medium from which the stem cells were removed. Also provided herein are populations of placental stem cells that have been passaged at least 1, 2, 3, 4, 5, 6, 7, 8, 9, 10, 12, 14, 16, 18, or 20 times, or more.

5.5.3 Placental Stem Cell Populations

In one aspect, placental stem cells and populations of placental stem cells are used as a source of differentiated cells, e.g., hepatocytes and/or hepatogenic cells, or chondrocytes and/or chondrogenic cells. Placental stem cell populations can be isolated directly from one or more placentas; that is, the placental stem cell population can be a population of placental cells, comprising placental stem cells, obtained from, or contained within, perfusate, or obtained from, or contained within, digestate (that is, the collection of cells obtained by enzymatic digestion of a placenta or part thereof). Isolated placental stem cells described herein can also be cultured and expanded to produce placental stem cell populations. Populations of placental cells comprising placental stem cells can also be cultured and expanded to produce placental stem cell populations.

Placental stem cell populations provided herein comprise placental stem cells, for example, placental stem cells as described herein. In various embodiments, at least 10%, 20%, 30%, 40%, 50%, 60%, 70%, 80%, 90%, 95%, or 99% of the cells in an isolated placental stem cell population are placental stem cells. That is, a placental stem cell population can comprise, e.g., as much as 1%, 5%, 10%, 20%, 30%, 40%, 50%, 60%, 70%, 80%, 90% non-stem cells.

Further provided herein are methods of producing isolated placental stem cell population by, e.g., selecting placental stem cells, whether derived from enzymatic digestion or perfusion, that express particular markers and/or particular culture or morphological characteristics. Such placental stem cells can be used to produce, e.g., hepatocytes and/or hepatogenic cells, or mixed populations of undifferentiated placental stem cells and hepatogenic cells and/or hepatocytes differentiated from placental stem cells; or chondrocytes and/or chondrogenic cells, or mixed populations of undifferentiated placental stem cells and chondrocytes and/or chondrogenic cells.

Cell populations comprising placental stem cells can be produced in a variety of different ways. In one embodiment, for example, a cell population comprising placental stem cells can be produced by selecting placental cells that (a) adhere to a substrate, and (b) express CD200 and HLA-G; and isolating said cells from other cells to form a cell population. In another embodiment, the method of producing a cell population comprises selecting placental cells that (a) adhere to a substrate, and (b) express CD73, CD105, and CD200; and isolating said cells from other cells to form a cell population. In another embodiment, the method of producing a cell population comprises selecting placental cells that (a) adhere to a substrate and (b) express CD200 and OCT-4; and isolating said cells from other cells to form a cell population. In another embodiment, the method of producing a cell population comprises selecting placental cells that (a) adhere to a substrate, (b) express CD73 and CD105, and (c) facilitate the formation of one or more embryoid-like bodies in a population of placental cells comprising said stem cell when said population is cultured under conditions that allow for the formation of an embryoid-like body; and isolating said cells from other cells to form a cell population. In another embodiment, the method of producing a cell population comprises selecting placental cells that (a) adhere to a substrate, and (b) express CD73, CD105 and HLA-G; and isolating said cells from other cells to form a cell population. In another embodiment, the method of producing a cell population comprises selecting placental cells that (a) adhere to a substrate, (b) express OCT-4, and (c) facilitate the formation of one or more embryoid-like bodies in a population of placental cells comprising said stem cell when said population is cultured under conditions that allow for the formation of an embryoid-like body; and isolating said cells from other cells to form a cell population. In any of the above embodiments, the method can additionally comprise selecting placental cells that express ABC$^-$ p (a placenta-specific ABC transporter protein; see, e.g., Allikmets et al., *Cancer Res.* 58(23): 5337-9 (1998)). The method can also comprise selecting cells exhibiting at least one characteristic specific to, e.g., a mesenchymal stem cell, for example, expression of CD29, expression of CD44, expression of CD90, or expression of a combination of the foregoing.

In any of the above embodiments of producing a cell population, the resulting population of cells can be additionally assessed for the ability of the cells, or of the population, to produce, e.g., hepatocytes, hepatogenic cells, chondrocytes, or chondrocytic cells.

In the above embodiments, the substrate can be any surface on which culture and/or selection of cells, e.g., placental stem cells, can be accomplished. Typically, the substrate is plastic, e.g., tissue culture dish or multiwell plate plastic. Tissue culture plastic can be coated with a biomolecule, e.g., laminin or fibronectin.

Cells, e.g., placental stem cells, can be selected for a placental stem cell population by any means known in the art of cell selection. For example, cells can be selected using an antibody or antibodies to one or more cell surface markers, for example, in flow cytometry or FACS. Selection can be accomplished using antibodies in conjunction with magnetic beads. Antibodies that are specific for certain stem cell-related markers are known in the art. For example, antibodies to OCT-4 (Abcam, Cambridge, Mass.), CD200 (Abcam), HLA-G (Abcam), CD73 (BD Biosciences Pharmingen, San Diego, Calif.), CD105 (Abcam; BioDesign International, Saco, Me.), etc. Antibodies to other markers are also available commercially, e.g., CD34, CD38 and CD45 are available from, e.g., StemCell Technologies or BioDesign International.

The isolated placental stem cell population can comprise placental cells that are not stem cells, or cells that are not placental cells.

Isolated placental stem cell populations can be combined with one or more populations of non-stem cells or non-placental cells. For example, an isolated population of placental stem cells can be combined with blood (e.g., placental blood or umbilical cord blood), blood-derived stem cells (e.g., stem cells derived from placental blood or umbilical cord blood), populations of blood-derived nucleated cells, bone marrow-derived mesenchymal cells, bone-derived stem cell populations, crude bone marrow, adult (somatic) stem cells, populations of stem cells contained within tissue, cultured stem cells, populations of fully-differentiated cells (e.g., chondrocytes, fibroblasts, amniotic cells, osteoblasts, muscle cells, cardiac cells, etc.) and the like. Cells in an isolated placental stem cell population can be combined with a plurality of cells of another type in ratios of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated placental stem cell population can be combined with a plurality of cells of a plurality of cell types, as well.

In one, an isolated population of placental stem cells is combined with a plurality of hematopoietic stem cells. Such hematopoietic stem cells can be, for example, contained within unprocessed placental, umbilical cord blood or peripheral blood; in total nucleated cells from placental blood, umbilical cord blood or peripheral blood; in an isolated population of CD34$^+$ cells from placental blood, umbilical cord blood or peripheral blood; in unprocessed bone marrow; in total nucleated cells from bone marrow; in an isolated population of CD34$^+$ cells from bone marrow, or the like.

Additional placental stem cells and placental stem cell populations that can be used in connection with the compositions and methods provided herein are described, for example, in U.S. patent application Ser. No. 11/648,813, and in U.S. Provisional Application No. 60/846,641, each of which is hereby incorporated by reference in its entirety.

5.5.4 Induction of Differentiation into Hepatic Cells

Differentiation of placental stem cells into hepatic cells can be accomplished, for example, by placing placental stem cells in cell culture conditions that induce differentiation into hepatic cells. In a specific embodiment, the placental stem cells are contacted with sodium butyrate for a time sufficient for the placental stem cells to exhibit one or more characteristics of a hepatocyte or hepatogenic cell.

An example hepatogenic medium comprises DMEM supplemented with sodium butyrate. Cells are cultured, e.g., for 14-28 days, refeeding every 3-4 days. Differentiation can be confirmed by assaying for, e.g., increased production of cytokeratin 18 (relative to an undifferentiated placental stem cell). Typically, placental stem cells express cytokeratin 18, but do not express at least one other cytokeratin expressed by hepatocytes. Differentiation can also be affirmed by the presence of one or more of asialogylcoprotein receptor, alpha-1-antitrypsin, albumin and cytochrome P450 activity. A placental stem cell is considered to have differentiated into a hepatic cell when the cell displays one or more of these characteristics.

In one aspect, provided herein are methods of producing and isolated population of hepatocytes and/or hepatogenic cells by, e.g., selecting a plurality of placental stem cells, whether derived from enzymatic digestion or perfusion, that express particular markers and/or particular culture or morphological characteristics, and exposing such cells to conditions that cause the differentiation of at least some of said placental stem cells into hepatocytes and/or hepatogenic cells. In one embodiment, for example, provided herein is a method of producing hepatocytes and/or hepatogenic cells comprising (1) selecting placental cells that (a) adhere to a substrate, and (b) express CD200 and HLA-G, or express CD73, CD105, and CD200, or express CD200 and OCT-4, or express CD73, CD105 and HLA-G, or express CD73 and CD105 and facilitate the formation of one or more embryoid-like bodies in a population of placental cells comprising said stem cell when said population is cultured under conditions that allow for the formation of an embryoid-like body, or express OCT-4 and (c) facilitate the formation of one or more embryoid-like bodies in a population of placental cells comprising said stem cell when said population is cultured under conditions that allow for the formation of an embryoid-like body; (2) isolating said placental cells from other placental cells; and exposing said cells to sodium butyrate for a time sufficient to produce a detectable number of said hepatocytes and/or hepatogenic cells. In a specific embodiment, the placental stem cells are CD10$^+$, CD34$^-$, CD105$^+$ and CD200$^+$.

In various specific embodiments of the above methods, at least, or about, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 98% of said placental stem cells differentiate into said hepatocytes and/or hepatogenic cells. In another specific embodiment of any of the above embodiments of the method, said placental cells are exposed to sodium butyrate for a time sufficient for a plurality of said cells to exhibit a detectable increase in the production of cytokeratin 18 relative to an undifferentiated placental stem cell, a detectable amount of asialogylcoprotein receptor, or a detectable amount of cytochrome P4507A1 activity, a detectable amount of albumin, or a detectable amount of expression of a gene encoding albumin. In another specific embodiment, 5.5.5 Induction of Differentiation into Chondrocytic Cells Chondrogenic differentiation of adherent placental stem cells can be accomplished, for example, by placing the placental stem cells in cell culture conditions that induce differentiation into chondrocytes. A preferred chondrocytic medium comprises MSCGM (Cambrex) or Dulbecco's Modified Eagle's Medium (DMEM) supplemented with 15% cord blood serum. In one embodiment, placental stem cells are aliquoted into a sterile polypropylene tube, centrifuged (e.g., at 150×g for 5 minutes), and washed twice in Incomplete Chondrogenesis Medium (Cambrex). The cells are resuspended in Complete Chondrogenesis Medium (Cambrex) containing 0.01 μg/ml transforming growth factor beta-3 (TGF-β3) at a concentration of about 1–20×10$^5$ cells/ml. In other embodiments, placental stem cells are contacted with exogenous growth factors, e.g., GDF-5 or TGF-β3, with or without ascorbate.

Another example chondrogenic medium comprises DMEM, 1% FBS, insulin, ascorbate 2-phosphate, and TGF-β1. A similar chondrogenic medium comprises, in 1 L, DMEM, 1% FBS, 1% penicillin-streptomycin, 37.5 µg/ml ascorbate-2-phophate, ITS premix (comprising, e.g., 100 mg of insulin, 100 mg of transferrin, and 100 pg of sodium selenate), and 10 ng/ml TGF-1 Another example chondrogenic medium is a defined medium (any standard defined medium suitable for mammalian cell culture) that includes 100 nM dexamethasone and 10 ng/ml transforming growth factor-β3 (TGF-β3).

Chondrogenic medium can be supplemented with amino acids including proline and glutamine, sodium pyruvate, dexamethasone, ascorbic acid, and insulin/transferrin/selenium. Chondrogenic medium can be supplemented with sodium hydroxide and/or collagen.

The adherent placental stem cells may be cultured at high or low density. Cells are preferably cultured in the absence of serum. Placental stem cells can be cultured under chondrogenic conditions either statically or dynamically, e.g., under conditions in which medium is circulated around cells. Cell culture can proceed for a detectable amount of differentiation occurs. In specific embodiments, adherent placental stem cells are cultured for about 28 days to about 56 days under chondrogenic conditions.

Adherent placental stem cells can be induced to differentiate into chondrocytes or chondrocytic cells by seeding the cells onto an electrospun nonwoven microfibrous or nanofibrous mat and culturing the cells under chondrogenic conditions. Such mats, and their production, are described in Section 5.7.1.4 herein.

Chondrogenesis can be assessed by e.g., observation of production of esoinophilic ground substance, safranin-O staining for glycosaminoglycan expression; methylene blue dye binding for determination of glycosaminoglycan expression; hematoxylin/eosin staining, assessing cell morphology, and/or RT/PCR confirmation of, or staining for, collagen 2 and collagen 9 gene expression. Chondrogenesis can also be observed by growing the stem cells in a pellet, formed, e.g., by gently centrifuging stem cells in suspension (e.g., at about 800 g for about 5 minutes). After about 1-28 days, the pellet of stem cells begins to form a tough matrix and demonstrates a structural integrity not found in non-induced, or non-chondrogenic, cell lines, pellets of which tend to fall apart when challenged. Chondrogenesis can also be demonstrated, e.g., in such cell pellets, by staining with a stain that stains collagen, e.g., Sirius Red, and/or a stain that stains glycosaminoglycans (GAGs), such as, e.g., Alcian Blue (also called Alcian blue 8GX, Ingrain blue 1, or C.I. 74240). A placental stem cell is considered to have differentiated into a chondrocytic cell when the cell displays one or more of these characteristics. Chondrogenesis can also be assessed by determination of gene expression, e.g., by real-time PCR, for early stage chondrogenesis markers fibromodulin and cartilage oligomeric matrix protein; gene expression for mid-stage chondrogenesis markers aggrecan, versican, decorin and biglycan; and gene expression for types II and X collagens and chondroadherin, which are markers of mature chondrocytes.

5.6 Preservation of Placental Stem Cells

Placental stem cells, and cells differentiated therefrom, e.g., hepatocytes and/or hepatogenic cells, chondrocytes and/or chondrocytic cells, can be preserved, that is, placed under conditions that allow for long-term storage, or conditions that inhibit cell death by, e.g., apoptosis or necrosis.

Placental stem cells, and cells differentiated therefrom, e.g., hepatocytes and/or hepatogenic cells, chondrocytes and/or chondrocytic cells, can be preserved using, e.g., a composition comprising an apoptosis inhibitor, necrosis inhibitor and/or an oxygen-carrying perfluorocarbon, as described in related U.S. application Ser. No. 11/648,812, entitled "Improved Composition for Collecting Placental Stem Cells and Preserving Organs" filed on Dec. 28, 2006. In one embodiment, provided herein is a method of preserving a population of cells, e.g., placental stem cells, and/or hepatocytes and/or hepatogenic cells, chondrocytes and/or chondrocytic cells differentiated therefrom, comprising contacting said cells with a stem cell collection composition comprising an inhibitor of apoptosis and an oxygen-carrying perfluorocarbon, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the cells. In another more specific embodiment, said apoptosis inhibitor and said perfluorocarbon are between about 2° C. and 10° C., or between about 2° C. and about 5° C., at the time of contacting the cells. In another more specific embodiment, said contacting is performed during transport of said population of stem cells. In another more specific embodiment, said contacting is performed during freezing and thawing of said population of stem cells.

In another embodiment, provided herein is a method of preserving a population of placental stem cells, and/or hepatocytes and/or hepatogenic cells, chondrocytes and/or chondrocytic cells differentiated therefrom, comprising contacting said population of cells with an inhibitor of apoptosis and an organ-preserving compound, wherein said inhibitor of apoptosis is present in an amount and for a time sufficient to reduce or prevent apoptosis in the population of cells, as compared to a population of cells not contacted with the inhibitor of apoptosis. In a specific embodiment, the organ-preserving compound is UW solution (described in U.S. Pat. No. 4,798,824; also known as VIASPAN®; see also Southard et al., *Transplantation* 49(2):251-257 (1990)) or a solution described in Stem et al., U.S. Pat. No. 5,552,267. In another embodiment, said organ-preserving compound is hydroxyethyl starch, lactobionic acid, raffinose, or a combination thereof. In another embodiment, the stem cell collection composition additionally comprises an oxygen-carrying perfluorocarbon, either in two phases or as an emulsion.

In another embodiment of the method, placental stem cells are contacted with a stem cell collection composition comprising an apoptosis inhibitor and oxygen-carrying perfluorocarbon, organ-preserving compound, or combination thereof, during perfusion. In another embodiment, said cells are contacted during a process of tissue disruption, e.g., enzymatic digestion. In another embodiment, placental stem cells are contacted with said stem cell collection compound after collection by perfusion, or after collection by tissue disruption, e.g., enzymatic digestion.

Typically, during placental cell collection, enrichment and isolation, it is preferable to minimize or eliminate cell stress due to hypoxia and mechanical stress. In another embodiment of the method, therefore, a stem cell, or population of stem cells, is exposed to a hypoxic condition during collection, enrichment or isolation for less than six hours during said preservation, wherein a hypoxic condition is a concentration of oxygen that is less than normal blood oxygen concentration. In a more specific embodiment, said population of stem cells is exposed to said hypoxic condition for less than two hours during said preservation. In another more specific embodiment, said population of stem cells is exposed to said hypoxic condition for less than one hour, or less than thirty minutes, or is not exposed to a hypoxic condition, during collection, enrichment or isolation. In another specific embodiment, said population of stem cells is not exposed to shear stress during collection, enrichment or isolation.

The placental stem cells used in the compositions and methods provided herein can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, methylcellulose and/or glycerol. Placental stem cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

5.7 Uses of Placental Stem Cells

5.7.1 Compositions Comprising Placental Stem Cells

The methods described herein can use compositions comprising placental stem cells, or biomolecules therefrom. In the same manner, the pluralities and populations of placental stem cells described herein can be combined with any physiologically-acceptable or medically-acceptable compound, composition or device for use in, e.g., research or therapeutics.

5.7.1.1 Cryopreserved Placental Stem Cells

The placental stem cell populations described herein can be preserved, for example, cryopreserved for later use. Methods for cryopreservation of cells, such as stem cells, are well known in the art. Placental stem cell populations can be prepared in a form that is easily administrable to an individual. For example, provided herein is a placental stem cell population that is contained within a container that is suitable for medical use. Such a container can be, for example, a sterile plastic bag, flask, jar, or other container from which the placental stem cell population can be easily dispensed. For example, the container can be a blood bag or other plastic, medically-acceptable bag suitable for the intravenous administration of a liquid to a recipient. The container is preferably one that allows for cryopreservation of the combined stem cell population.

Cryopreserved placental stem cell populations can comprise placental stem cells derived from a single donor, or from multiple donors. The placental stem cell population can be completely HLA-matched to an intended recipient, or partially or completely HLA-mismatched.

Cryopreserved placental stem cells can be, for example, in the form of a composition comprising an placental stem cell population in a container. In a specific embodiment, the stem cell population is cryopreserved. In another specific embodiment, the container is a bag, flask, or jar. In a more specific embodiment, said bag is a sterile plastic bag. In a more specific embodiment, said bag is suitable for, allows or facilitates intravenous administration of said placental stem cell population. The bag can comprise multiple lumens or compartments that are interconnected to allow mixing of the placental stem cells and one or more other solutions, e.g., a drug, prior to, or during, administration. In another specific embodiment, the composition comprises one or more compounds that facilitate cryopreservation of the combined stem cell population. In another specific embodiment, said placental stem cell population is contained within a physiologically-acceptable aqueous solution. In a more specific embodiment, said physiologically-acceptable aqueous solution is a 0.9% NaCl solution. In another specific embodiment, said placental stem cell population comprises placental cells that are HLA-matched to a recipient of said stem cell population. In another specific embodiment, said combined stem cell population comprises placental cells that are at least partially HLA-mismatched to a recipient of said stem cell population. In another specific embodiment, said placental stem cells are derived from a plurality of donors.

5.7.1.2 Pharmaceutical Compositions

Populations of placental stem cells, or populations of cells comprising placental stem cells, can be formulated into pharmaceutical compositions for use in vivo. Such pharmaceutical compositions comprise a population of placental stem cells, or a population of cells comprising placental stem cells, in a pharmaceutically-acceptable carrier, e.g., a saline solution or other accepted physiologically-acceptable solution for in vivo administration. Pharmaceutical compositions provided herein, comprising placental stem cells, can comprise any of the placental stem cell populations, or placental stem cell types, described elsewhere herein. The pharmaceutical compositions can comprise fetal, maternal, or both fetal and maternal placental stem cells. The pharmaceutical compositions can further comprise placental stem cells obtained from a single individual or placenta, or from a plurality of individuals or placentae.

The pharmaceutical compositions can comprise any number of placental stem cells. For example, a single unit dose of placental stem cells can comprise, in various embodiments, about, at least, or no more than $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more placental stem cells.

The pharmaceutical compositions may comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, and the like.

5.7.1.3 Placental Stem Cell Conditioned Media

The placental stem cells provided herein can be used to produce conditioned medium, that is, medium comprising one or more biomolecules secreted or excreted by the stem cells. In various embodiments, the conditioned medium comprises medium in which placental stem cells have grown for at least 1, 2, 3, 4, 5, 6, 7, 8, 9, 10, 11, 12, 13, 14 or more days. In other embodiments, the conditioned medium comprises medium in which placental stem cells have grown to at least 30%, 40%, 50%, 60%, 70%, 80%, 90% confluence, or up to 100% confluence. Such conditioned medium can be used to support the culture of a separate population of placental stem cells, or stem cells of another kind. In another embodiment, the conditioned medium comprises medium in which placental stem cells have been differentiated into an adult cell type. In another embodiment, conditioned medium comprises medium in which placental stem cells and non-placental stem cells have been cultured.

Thus, in one embodiment, provided herein is a composition comprising culture medium, e.g., conditioned medium, from a culture of adherent placental stem cells, wherein said adherent placental stem cells (a) adhere to a substrate; (b) express CD200 and HLA-G, or express CD73, CD105, and CD200, or express CD200 and OCT-4, or express CD73, CD105, and HLA-G, or express CD73 and CD105 and facilitate the formation of one or more embryoid-like bodies in a population of placental cells that comprise the placental stem cells, when said population is cultured under conditions that allow formation of embryoid-like bodies, or express OCT-4 and facilitate the formation of one or more embryoid-like bodies in a population of placental cells that comprise the placental stem cells when said population is cultured under conditions that allow formation of embryoid-like bodies, wherein said culture of placental stem cells has been cultured in said medium for 24 hours or more. In a specific embodiment, said composition comprises medium conditioned by $CD34^+$, $CD45^-$ placental stem cells. In another specific embodiment, the composition further comprises a plurality of said placental stem cells, e.g., a plurality of adherent placental stem cells and/or a plurality of non-adherent, $CD34^+$, $CD45^-$ placental stem cells. In another specific embodiment, the composition comprises a plurality of non-placental cells. In a more specific embodiment, said non-placental cells comprise $CD34^+$ cells, e.g., hematopoietic progenitor cells, derived from a non-placental source such as peripheral blood hematopoietic progenitor cells, cord blood hematopoietic progenitor cells, or placental blood hematopoietic progenitor cells. The non-placental cells can also comprise other stem cells, such as mesenchymal stem cells, e.g., bone marrow-derived mesenchymal stem cells. The non-placental cells can also be one or more types of adult cells or cell lines. In another specific embodiment, the composition comprises an anti-proliferative agent, e.g., an anti-MIP-1α or anti-MIP-1β antibody.

In another embodiment, conditioned medium is, or comprises, medium conditioned by a population of hepatocytes, hepatogenic cells, chondrocytes and/or chondrocytic cells differentiated from placental stem cells. Such a population can comprise placental stem cells, hepatogenic cells or chondrogenic cells differentiated from placental stem cells, hepatocytes or chondrocytes differentiated from placental stem cells, or any combination of the foregoing. Thus, in one embodiment, provided herein is a composition comprising culture medium from a culture of hepatocytes, hepatogenic cells, chondrocytes and/or chondrocytic cells differentiated from placental stem cells, wherein said placental stem cells (a) adhere to a substrate; (b) express CD200 and HLA-G, or express CD73, CD105, and CD200, or express CD200 and OCT-4, or express CD73, CD105, and HLA-G, or express CD73 and CD105 and facilitate the formation of one or more embryoid-like bodies in a population of placental cells that comprise the placental stem cells, when said population is cultured under conditions that allow formation of embryoid-like bodies, or express OCT-4 and facilitate the formation of one or more embryoid-like bodies in a population of placental cells that comprise the placental stem cells when said population is cultured under conditions that allow formation of embryoid-like bodies, wherein said culture of hepatocytes, hepatogenic cells, chondrocytes and/or chondrocytic cells has been cultured in said medium for 24 hours or more. In a specific embodiment, the composition further comprises a plurality of said placental stem cells. In another specific embodiment, the composition comprises a plurality of non-placental cells, e.g., hepatocytes from primary culture; hepatocyte cell line cells; hepatoma cells, and the like. In a more specific embodiment, said non-placental cells comprise $CD34^+$ cells, e.g., hematopoietic progenitor cells, such as peripheral blood hematopoietic progenitor cells, cord blood hematopoietic progenitor cells, or placental blood hematopoietic progenitor cells. The non-placental cells can also comprise other stem cells, such as mesenchymal stem cells, e.g., bone marrow-derived mesenchymal stem cells. The non-placental cells can also be one or more types of adult cells or cell lines. In another specific embodiment, the composition comprises an anti-proliferative agent, e.g., an anti-MIP-1α or anti-MIP-1β antibody.

5.7.1.4 Matrices Comprising Placental Stem Cells

In another aspect, provided herein are matrices, hydrogels, scaffolds, and the like that comprise a population of hepatocytes, hepatogenic cells, chondrocytes and/or chondrocytic cells, differentiated from the adherent placental stem cells described herein.

Placental stem cells, or hepatocytes, hepatogenic cells, chondrocytes and/or chondrocytic cells differentiated from the placental stem cells, can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which placental stem cells can be seeded are described in Hariri, U.S. Application Publication No. 2004/0048796.

Placental stem cells, or cells differentiated therefrom, e.g., hepatocytes, hepatogenic cells, chondrocytes and/or chondrocytic cells, can be suspended in a hydrogel solution suitable for, e.g., injection. Suitable hydrogels for such compositions include self-assembling peptides, such as RAD 16. In one embodiment, a hydrogel solution comprising the cells can be allowed to harden, for instance in a mold, to form a matrix having cells dispersed therein for implantation. Cells in such a matrix can also be cultured so that the cells are mitotically expanded prior to implantation. The hydrogel can be, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix is biodegradable.

In some embodiments, the formulation comprises an in situ polymerizable gel (see, e.g., U.S. Patent Application Publication 2002/0022676; Anseth et al., *J. Control Release*, 78(1-3): 199-209 (2002); Wang et al., *Biomaterials*, 24(22): 3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The placental stem cells, or hepatocytes, hepatogenic cells, chondrocytes and/or chondrocytic cells differentiated from the placental stem cells, or co-cultures thereof can be seeded onto a three-dimensional framework or scaffold and implanted in vivo. Such a framework can be implanted in combination with any one or more growth factors, cells, drugs or other components that stimulate tissue formation.

Examples of scaffolds that can be used include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

In another embodiment, the scaffold is, or comprises, a nanofibrous scaffold, e.g., an electrospun nanofibrous scaffold. In a more specific embodiment, said nanofibrous scaffold comprises poly(L-lactic acid) (PLLA), poly lactic glycolic acid (PLGA), type I collagen, a copolymer of vinylidene fluoride and trifluoroethylene (PVDF-TrFE), poly(-caprolactone), poly(L-lactide-co-ε-caprolactone) [P(LLA-CL)] (e.g., 75:25), and/or a copolymer of poly(3-hydroxybutyrate-co-3-hydroxyvalerate) (PHBV) and type I collagen. In another more specific embodiment, said scaffold promotes the differentiation of placental stem cells into chondrocytes. Methods of producing nanofibrous scaffolds, e.g., electrospun nanofibrous scaffolds, are known in the art. See, e.g., Xu et al., *Tissue Engineering* 10(7): 1160-1168 (2004); Xu et al., *Biomaterials* 25:877-886 (20040; Meng et al., *J. Biomaterials Sci., Polymer Edition* 18(1):81-94 (2007).

The compositions listed above can be electrospun into a nonwoven mat comprising nanoscale fiber meshes with controllable porosity. In electrospinning, a high voltage is used to create an electrically charged jet of polymer solution, which dries or solidifies to leave a polymer fiber. One electrode is placed into the polymer solution in, e.g., a tube or capillary, e.g., a needle, and the other attached to a collector. An electric field is passed to the end of the tube or capillary, inducing a charge on the surface of the liquid. Mutual charge repulsion causes a force directly opposite to the surface tension of the solution. As the intensity of the electric field is increased, the repulsive electrostatic force overcomes the surface tension, and a charged jet of fluid is ejected from the solution at the tip of the tube or capillary. Solvent in the discharged polymer solution jet evaporates, leaving behind a charged polymer fiber, which lays itself randomly on a grounded collecting metal screen. The thickness of the mat, and the thickness of the fibers in the mat, can be adjusted by increasing or decreasing the distance between tube and collection screen, with increasing distance generally resulting in finer fibers and a less-dense mat; by increasing or decreasing the electric potential, in kilovolts, with increasing potential generally resulting in decreased fiber thickness; by increasing or decreasing the flow rate, with increasing flow rate generally resulting in thicker fibers; or increasing or decreasing the polymer concentration in solution, with increasing polymer concentration generally resulting in increased fiber thickness. The diameter of the tube at the tip can also be varied. In specific embodiments, any polymer, e.g., any of the polymers disclosed herein, suitable for electrospinning to create nanoscale nonwoven fibrous meshes or mats, e.g., PLLA or PLGA, can be electrospun at a voltage of, e.g., about 5 kV, 10 kV, 15 kV, 20 kV, 25 kV, 30 kV, 35 kV or about 40 kV; and the needle distance can be varied, e.g., from about 1, 2, 3, 4, 5, 6, 7, 8, 9, 0, 12, 14, 16, 18, 20, 22, 24, 26, 28, 30, 32, 34, 36, 38, 40, 42, 44, 46, 48 or about 50 cm between needle tip and collection screen. The needle gauge can be varied, e.g., from about 8G to about 24G, e.g., 12G or 22G. The flow rate can be varied, e.g., from about 0.01 to about 1.0 mL/min, e.g., about 0.05 to about 0.1 mL/min. The solution concentration, using any of the polymers, can range from about 5% to about 50% w/w in solution, e.g., about 10% to about 25% w/w. In specific embodiments, PLLA or PLGA at about 10% to about 25% w/w in solution can be electrospun using a 12G needle or 22G needle using a tip to collection screen distance of 30 cm and a flow rate of about 0.05 mL/min to about 0.1 mL/min to produce electrospun mats comprising fibers of an average diameter of about 250 nm to about 10 μm.

Placental stem cells of the invention can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, A G, Bettlach, Switzerland), and mineralized collagen bone grafting products such as HEALOS™. (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, placental stem cells, or hepatocytes and/or hepatogenic cells differentiated from the placental stem cells, can be seeded onto, or contacted with, a felt, which can be, e.g., composed of a multifilament yarn made from a bioabsorbable material such as PGA, PLA, PCL copolymers or blends, or hyaluronic acid.

The placental stem cells, or hepatocytes, hepatogenic cells, chondrocytes and/or chondrocytic cells differentiated from the placental stem cells, can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1 M acetic acid followed by incubation in polylysine, PBS, and/or collagen, prior to inoculation of cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with placental stem cells.

Thus, in another aspect, provided herein is a composition comprising isolated adherent $CD10^+$, $CD34^-$, $CD105^+$, $CD200^+$ placental stem cells and an electrospun nanofibrous scaffold. In a specific embodiment, said nanofibrous scaffold comprises fibers of poly(L-lactic acid) (PLLA), poly lactic glycolic acid (PLGA), type I collagen, a copolymer of vinylidene fluoride and trifluoroethylene (PVDF-TrFE), poly(-caprolactone), poly(L-lactide-co-ε-caprolactone) [P(LLA-CL)] (e.g., 75:25), and/or a copolymer of poly(3-hydroxybutyrate-co-3-hydroxyvalerate) (PHBV) and type I collagen. In another specific embodiment, said nanofibrous scaffold comprises fibers that average between about 250 nanometers and about 10 µm in thickness. In another specific embodiment, said composition is contacted with conditions in which the placental stem cells differentiate into chondrogenic cells or chondrocytes. In another embodiment, provided herein is a method of making a composition comprising contacting adherent $CD10^+$, $CD34^-$, $CD105^+$, $CD200^+$ placental stem cells with an electrospun nanofibrous scaffold, wherein said nanofibrous scaffold is made by electrospinning PLLA or PLGA at about 20 kV at about 30 cm needle to collector distance and about 0.05 mL/min. to about 0.1 mL/min flow rate, wherein said PLLA or PLGA are in solution at about 10% w/w to about 20% w/w.

5.7.2 Genetically Modified Placental Stem Cells

In another aspect, the placental stem cells and umbilical cord stem cells described herein can be genetically modified, e.g., to produce a nucleic acid or polypeptide of interest, or to produce a differentiated cell, e.g., a hepatocyte, hepatogenic cell, chondrocyte and/or chondrocytic cell, that produces a nucleic acid or polypeptide of interest. Genetic modification can be accomplished, e.g., using virus-based vectors including, but not limited to, non-integrating replicating vectors, e.g., papilloma virus vectors, SV40 vectors, adenoviral vectors; integrating viral vectors, e.g., retrovirus vector or adeno-associated viral vectors; or replication-defective viral vectors. Other methods of introducing DNA into cells include the use of liposomes, electroporation, a particle gun, direct DNA injection, or the like.

Stem cells can be, e.g., transformed or transfected with DNA controlled by or in operative association with, one or more appropriate expression control elements, for example, promoter or enhancer sequences, transcription terminators, polyadenylation sites, internal ribosomal entry sites. Preferably, such a DNA incorporates a selectable marker. Following the introduction of the foreign DNA, engineered stem cells can be, e.g., grown in enriched media and then switched to selective media. In one embodiment, the DNA used to engineer a placental stem cell comprises a nucleotide sequence encoding a polypeptide of interest, e.g., a cytokine, growth factor, differentiation agent, or therapeutic polypeptide.

The DNA used to engineer the stem cell can comprise any promoter known in the art to drive expression of a nucleotide sequence in mammalian cells, e.g., human cells. For example, promoters include, but are not limited to, CMV promoter/enhancer, SV40 promoter, papillomavirus promoter, Epstein-Barr virus promoter, elastin gene promoter, and the like. In a specific embodiment, the promoter is regulatable so that the nucleotide sequence is expressed only when desired. Promoters can be either inducible (e.g., those associated with metallothionein and heat shock proteins) or constitutive.

In another specific embodiment, the promoter is tissue-specific or exhibits tissue specificity. Examples of such promoters include but are not limited to: myelin basic protein gene control region (Readhead et al., 1987, *Cell* 48:703) (oligodendrocyte cells); elastase I gene control region (Swit et al., 1984, *Cell* 38:639; Ornitz et al., 1986, *Cold Spring Harbor Symp. Quant. Biol.* 50:399; MacDonald, 1987, *Hepatology* 7:425) (pancreatic acinar cells); insulin gene control region (Hanahan, 1985, *Nature* 315:115) (pancreatic beta cells); myosin light chain-2 gene control region (Shani, 1985, *Nature* 314:283) (skeletal muscle).

The cells of the invention may be engineered to "knock out" or "knock down" expression of one or more genes. The expression of a gene native to a cell can be diminished by, for example, inhibition of expression by inactivating the gene completely by, e.g., homologous recombination. In one embodiment, for example, an exon encoding an important region of the protein, or an exon 5' to that region, is interrupted by a positive selectable marker, e.g., neo, preventing the production of normal mRNA from the target gene and resulting in inactivation of the gene. A gene may also be inactivated by creating a deletion in part of a gene or by deleting the entire gene. By using a construct with two regions of homology to the target gene that are far apart in the genome, the sequences intervening the two regions can be deleted (Mombaerts et al., 1991, *Proc. Nat. Acad. Sci. U.S.A.* 88:3084). Antisense, DNAzymes, small interfering RNA, and ribozyme molecules that inhibit expression of the target gene can also be used to reduce the level of target gene activity in the stem cells. For example, antisense RNA molecules which inhibit the expression of major histocompatibility gene complexes (HLA) have been shown to be most versatile with respect to immune responses. Triple helix molecules can be utilized in reducing the level of target gene activity. See, e.g., L. G. Davis et al. (eds), 1994, BASIC METHODS IN MOLECULAR BIOLOGY, 2nd ed., Appleton & Lange, Norwalk, Conn., which is incorporated herein by reference.

In a specific embodiment, the placental or umbilical cord stem cells of the invention can be genetically modified with a nucleic acid molecule comprising a nucleotide sequence encoding a polypeptide of interest, wherein expression of the polypeptide of interest is controllable by an exogenous factor, e.g., polypeptide, small organic molecule, or the like. Such a polypeptide can be a therapeutic polypeptide. In a more specific embodiment, the polypeptide of interest is IL-12 or interleukin-1 receptor antagonist (IL-1Ra). In another more specific embodiment, the polypeptide of interest is a fusion of interleukin-1 receptor antagonist and dihydrofolate reductase (DHFR), and the exogenous factor is an antifolate, e.g., methotrexate. Such a construct is useful in the engineering of placental or umbilical cord stem cells that express IL-1Ra, or a fusion of IL-1Ra and DHFR, upon contact with methotrexate. Such a construct can be used, e.g., in the treatment of rheumatoid arthritis. In this embodiment, the fusion of IL-1Ra and DHFR is translationally upregulated upon exposure to an antifolate such as methotrexate. Therefore, in another specific embodiment, the nucleic acid used to genetically engineer a placental stem cell or umbilical cord stem cell can comprise nucleotide sequences encoding a first polypeptide and a second polypeptide, wherein said first and second polypeptides are expressed as a fusion protein that is translationally upregulated in the presence of an exogenous factor. The polypeptide can be expressed transiently or long-term (e.g., over the course of weeks or months).

Such a nucleic acid molecule can additionally comprise a nucleotide sequence encoding a polypeptide that allows for positive selection of engineered stem cells, or allows for visualization of the engineered stem cells. In another more specific embodiment, the nucleotide sequence encodes a polypeptide that is, e.g., fluorescent under appropriate visualization conditions, e.g., luciferase (Luc). In a more specific embodiment, such a nucleic acid molecule can comprise IL-1Ra-DHFR-IRES-Luc, where IL-1Ra is interleukin-1 receptor antagonist, IRES is an internal ribosomal entry site, and DHFR is dihydrofolate reductase.

5.7.3 Immortalized Placental Stem Cell Lines

Mammalian placental cells can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. in one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{CMV^*-1}$, a minimal promoter from human cytomegalovirus fused to tet operator sequences. tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed. Cells carrying $neo^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized placental stem cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human placental stem cell line prepared as described above. In general, such clonal cell lines may be isolated using standard techniques, such as by limit dilution or using cloning rings, and expanded. Clonal cell lines may generally be fed and passaged as described above.

Conditionally-immortalized human placental stem cell lines, which may, but need not be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

5.7.4 Assays

The placental stem cells, or hepatocytes and/or hepatogenic cells, described herein can be used in assays to determine the influence of culture conditions, environmental factors, molecules (e.g., biomolecules, small inorganic molecules. etc.) and the like on the proliferation, expansion, and/or differentiation of such cells, compared to cells not exposed to such conditions.

In one embodiment, the hepatocytes and/or hepatogenic cells described herein are assayed for changes in proliferation, expansion or differentiation upon contact with a molecule. In one embodiment, for example, provided herein is a method of identifying a compound that modulates the proliferation of a plurality of hepatocytes and/or hepatogenic cells differentiated from placental stem cells, comprising contacting said cells with said compound under conditions that allow proliferation, wherein if said compound causes a detectable change in proliferation of said cells compared to such cells not contacted with said compound, said compound is identified as a compound that modulates proliferation of hepatocytes and/or hepatogenic cells. In a specific embodiment, said compound is identified as an inhibitor of proliferation. In another specific embodiment, said compound is identified as an enhancer of proliferation.

In another embodiment, provided herein is a method of identifying a compound that modulates the expansion of a plurality of hepatocytes and/or hepatogenic cells differentiated from placental stem cells, comprising contacting said hepatocytes and/or hepatogenic cells with said compound under conditions that allow expansion, wherein if said compound causes a detectable change in expansion of said hepatocytes and/or hepatogenic cells compared to a plurality of hepatocytes and/or hepatogenic cells not contacted with said compound, said compound is identified as a compound that modulates expansion of hepatocytes and/or hepatogenic cells. In a specific embodiment, said compound is identified as an inhibitor of expansion. In another specific embodiment, said compound is identified as an enhancer of expansion.

In another embodiment, provided herein is a method of identifying a compound that modulates the differentiation of a placental stem cell, e.g., differentiation to a hepatocyte and/or a hepatogenic cell, comprising contacting said stem cells with said compound under conditions that allow differentiation to a hepatocyte or a hepatogenic cell, wherein if said compound causes a detectable change in differentiation of said stem cells compared to a stem cell not contacted with said compound, said compound is identified as a compound that modulates proliferation of placental stem cells. In a specific embodiment, said compound is identified as an inhibitor of differentiation. In another specific embodiment, said compound is identified as an enhancer of differentiation.

5.7.5 Cell Banks

Stem cells from postpartum placentas can be cultured in a number of different ways to produce a set of lots, e.g., a set of individually-administrable doses, of placental stem cells. Such lots can, for example, be obtained from stem cells from placental perfusate or from enzyme-digested placental tissue. Sets of lots of placental stem cells, obtained from a plurality of placentas, can be arranged in a bank of placental stem cells for, e.g., long-term storage. Generally, adherent stem cells are obtained from an initial culture of placental material to form a seed culture, which is expanded under controlled conditions to form populations of cells from approximately equivalent numbers of doublings. Lots are preferably derived from the tissue of a single placenta, but can be derived from the tissue of a plurality of placentas.

In one embodiment, stem cell lots are obtained as follows. Placental tissue is first disrupted, e.g., by mincing, digested with a suitable enzyme, e.g., collagenase (see Section 5.2.3, above). The placental tissue preferably comprises, e.g., the entire amnion, entire chorion, or both, from a single placenta, but can comprise only a part of either the amnion or chorion. The digested tissue is cultured, e.g., for about 1-3 weeks, preferably about 2 weeks. After removal of non-adherent cells, high-density colonies that form are collected, e.g., by trypsinization. These cells are collected and resuspended in a convenient volume of culture medium, and defined as Passage 0 cells.

Passage 0 cells are then used to seed expansion cultures. Expansion cultures can be any arrangement of separate cell culture apparatuses, e.g., a Cell Factory by NUNC™. Cells in the Passage 0 culture can be subdivided to any degree so as to seed expansion cultures with, e.g., $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, or $10 \times 10^4$ stem cells. Preferably, from about $2 \times 10^4$ to about $3 \times 10^4$ Passage 0 cells are used to seed each expansion culture. The number of expansion cultures can depend upon the number of Passage 0 cells, and may be greater or fewer in number depending upon the particular placenta(s) from which the stem cells are obtained.

Expansion cultures are grown until the density of cells in culture reaches a certain value, e.g., about $1 \times 10^5$ cells/cm$^2$. Cells can either be collected and cryopreserved at this point, or passaged into new expansion cultures as described above. Cells can be passaged, e.g., 2, 3, 4, 5, 6, 7, 8, 9, 10, 11, 12, 13, 14, 15, 16, 17, 18, 19 or 20 times prior to use. A record of the cumulative number of population doublings is preferably maintained during expansion culture(s). The cells from a Passage 0 culture can be expanded for 2, 3, 4, 5, 6, 7, 8, 9, 10, 12, 14, 16, 18, 20, 22, 24, 26, 28, 30, 32, 34, 36, 38 or 40 doublings, or up to 60 doublings. Preferably, however, the number of population doublings, prior to dividing the population of cells into individual doses, is between about 15 and about 30, preferably about 20 doublings. The cells can be culture continuously throughout the expansion process, or can be frozen at one or more points during expansion.

Cells to be used for individual doses can be frozen, e.g., cryopreserved for later use. Individual doses can comprise, e.g., about 1 million to about 100 million cells per ml, and can comprise between about $10^6$ and about $10^9$ cells in total.

In a specific embodiment, of the method, Passage 0 cells are cultured for approximately 4 doublings, then frozen in a first cell bank. Cells from the first cell bank are frozen and used to seed a second cell bank, the cells of which are expanded for about another eight doublings. Cells at this stage are collected and frozen and used to seed new expansion cultures that are allowed to proceed for about eight additional doublings, bringing the cumulative number of cell doublings to about 20. Cells at the intermediate points in passaging can be frozen in units of about 100,000 to about 10 million cells per ml, preferably about 1 million cells per ml for use in subsequent expansion culture. Cells at about 20 doublings can be frozen in individual doses of between about 1 million to about 100 million cells per ml for administration or use in making a stem cell-containing composition.

In a preferred embodiment, the donor from which the placenta is obtained (e.g., the mother) is tested for at least one pathogen. If the mother tests positive for a tested pathogen, the entire lot from the placenta is discarded. Such testing can be performed at any time during production of placental stem cell lots, including before or after establishment of Passage 0 cells, or during expansion culture. Pathogens for which the presence is tested can include, without limitation, hepatitis A, hepatitis B, hepatitis C, hepatitis D, hepatitis E, human immunodeficiency virus (types I and II), cytomegalovirus, herpesvirus, and the like.

In a modification of the above banks, a plurality, or all, of the placental stem cells in a bank, e.g., placental stem cells from a single placenta, or from multiple placentas, are exposed to conditions that cause differentiation of the cells into hepatocytes and/or hepatogenic cells. Such cells can be selected based on the expression of one or more hepatocyte markers not present in, or present at a detectably different level in, placental stem cells. In such an embodiment, a bank of cells can comprise populations of hepatocytes and/or hepatogenic cells, alone or in combination with placental stem cells not differentiated to hepatocytes or hepatogenic cells.

5.7.6 Treatment of Liver Disease

In another aspect, provided herein is a method of treating a subject having a disease, disorder or condition associated with abnormal liver function, comprising introducing a hepatocyte, or population of hepatocytes, produced according to the methods of differentiating placental stem cells into hepatocytes disclosed herein, into said subject. In a more specific embodiment, the disease, disorder or condition is cirrhosis of the liver. In certain embodiments, the disease or conditions results from liver toxicity caused by, e.g., alcohol or ingestion of toxins such as, e.g., mushroom toxins. In certain embodiments, the disease or condition is a viral infection, e.g., a hepatitis A, B, C, D, or E infection.

An individual having a disease associated with abnormal liver function, e.g., an individual diagnosed with cirrhosis, can be treated with a plurality of placental stem cells, and, optionally, one or more therapeutic agents, at any time during the progression of the disease. For example, the individual can be treated immediately after diagnosis, or within 1, 2, 3, 4, 5, 6 days of diagnosis, or within 1, 2, 3, 4, 5, 6, 7, 8, 9, 10, 15, 20, 25, 30, 35, 40, 45, 50 or more weeks, or 1, 2, 3, 4, 5, 6, 7, 8, 9, 10 or more years after diagnosis. The individual can be treated once, or multiple times during the clinical course of the disease. In one embodiment, the individual is administered a dose of about 300 million placental stem cells. Dosage, however, can vary according to the individual's physical characteristics, e.g., weight, and can range from 1 million to 10 billion placental stem cells per does, preferably between 10 million and 1 billion per dose, or between 100 million and 50 million placental stem cells per dose.

The administration is preferably intravenous, but can be by any art-accepted route for the administration of live cells. Placental stem cells, e.g., placental stem cells that have been differentiated into cells that express one or more characteristics of a hepatocyte, can be transplanted directly into one or more sites of a liver, e.g., in a buffer or medium solution, hydrogel, alginate. In one embodiment, the placental stem cells are from a cell bank.

In another embodiment, the plurality of placental stem cells has been contacted with one or more agents that promote differentiation of the placental stem cells into hepatocytes or into hepatogenic cells. In such a plurality of cells, some of the cells can be undifferentiated placental stem cells (i.e., placental stem cells that have not begun to differentiate into hepatocytes); some of the cells can be placental stem cells that have begun to express one or more characteristics of hepatocytes; and some can be cells, differentiated from placental stem cells, that have begun to express a plurality, a majority, or all of the characteristics of a terminally-differentiated hepatocyte.

5.7.7 Use of Placental Stem Cell-Derived Hepatocytes to Identify Antiviral Agents The hepatocytes and hepatocyte cultures described herein can be used in in vitro or in vivo assays to determine whether a compound is an antiviral agent.

In vitro assays. A plurality (e.g., population) of placental stem cells can be used to identify antiviral agents in one embodiment as follows. A population of placental stem cells is established as described elsewhere herein. The population of placental stem cells is contacted with one or more compounds or agents that promote the differentiation of the placental stem cells into hepatocytes. The placental stem cells are then cultured until at least a plurality of the placental stem cells express one or more markers characteristic of hepatocytes, or, in the case of, e.g., cytokeratin 18, at a level characteristic of hepatocytes.

Placenta-derived hepatocytes, or hepatogenic cells, are then infected with virus. The virus is preferably a virus that specifically infects hepatic tissue, e.g., hepatitis A, B, C, D or E. Virus stocks can be obtained from the serum of one or more individuals infected with the virus who have detectable level of the virus in their serum. Virus can also be obtained from infected animals, e.g., from infected rodents, rabbits, or the like; from commercial sources, or from cell lines infected with the virus.

Regardless of source, the virus is contacted with the placenta-derived hepatocytes, or population of placental stem cells comprising hepatocytes and/or hepatogenic cells, and is given sufficient time to infect. The hepatocytes or population of placental cells can be about, at least or at most 10%, 20%, 30%, 40%, 50%, 60%, 70%, 80%, 90% or 95% confluent at the time of infection, e.g., in a tissue culture dish or flask. In various embodiments, the hepatocytes or hepatogenic cells, or population of hepatocytes or hepatogenic cells, differentiated from placental stem cells, are infected with a virus, e.g., a hepatotrophic virus, e.g., with about $1 \times 10^8$ to $1 \times 10^9$ virions.

In a specific embodiment, placenta-derived hepatocytes or populations of placental stem cells comprising hepatocytes and/or hepatogenic cells are collected from cell culture by trypsinization and centrifugation, washed, an resuspended in medium. Aliquots of cells are placed on coverslips in a 12-well plate, and treated with 2% dimethylsulfoxide (DMSO) and optionally for 6-10 days. Cells are then incubated with virions, e.g., in infected serum, at 37° C. for 10-20 hours. In another embodiment, placental stem cell-derived hepatocytes or populations of placental stem cells comprising hepatocytes and/or hepatogenic cells are infected by co-culture with an virus-infected cells line that sheds virus, e.g., hepatoma cell line HB 611, which is infected with HBV (see Ochiya et al., "An In Vitro System for Infection with Hepatitis B Virus That Uses Primary Human Fetal Hepatocytes," *Proc. Natl. Acad. Sci. U.S.A.* 86:1875-1879 (1989).

At 2-5 days post-infection, the cells are collected, and the level of virus present is determined. Viral levels can be determined using, e.g., one or more antibodies that recognize a viral antigen, e.g., hepatitis A virus surface antigen (antibodies available from AbD Serotec); hepatitis B virus HBsAg of HBeAg; hepatitis C virus core antigen; hepatitis D core antigen or hepatitis E core antigen. In another embodiment, the level of virus in the infected cells is determined by quantitative or semi-quantitative PCR. In a specific embodiment, the primers used detect or are specific for a replicating form of the virus, e.g., are specific for the covalently closed circular form of HBV (cccHBV). In another specific embodiment, the primers used can amplify both cccHBV and the relaxed circular form of HBV.

A compound or agent can be tested for antiviral activity at several points in the above-outlined procedure. For example, the compound can be contacted with the hepatocytes or hepatogenic cells provided herein at the time of collection from culture; after centrifugation but before contact with the virus; at the same time as contact with the virus (e.g., simultaneously or within minutes); or after contact with the virus. For example, in one embodiment, contact between the compound and hepatocytes or hepatogenic cells provided herein can be accomplished prior to infection with the virus, to determine the effect the compound has on initial infection. In another embodiment, the compound can be contacted with infected hepatocytes or hepatogenic cells provided herein from about 1 to about 5 days after infection to determine, e.g., if the compound has an effect on production of virus compared to cells that are not contacted with the compound. In another embodiment, infected cells can be contacted with the compound of interest and cocultured with uninfected hepatocytes or hepatogenic cells provided herein, or primary hepatocyte cultures, to determine if the compound has any effect on infection of uninfected cells.

In a specific embodiment, a compound is an antiviral compound if the compound causes a detectable reduction in the amount of virus produced by infected hepatocytes or hepatogenic cells provided herein at any time, e.g., within 1, 2, 3, 4, 5, 6 or 7 days after contact with the compound, compared to hepatocytes or hepatogenic cells not contacted with the compound. In another specific embodiment, a compound is an antiviral compound if the compound causes a detectable reduction in the number of infected hepatocytes in a coculture of infected hepatocytes and uninfected hepatocytes in the presence of the compound, compared to a coculture in the absence of the compound.

In vivo assays. Hepatocytes or hepatogenic cells, differentiated from placental stem cells, can be used as part of an in vivo assay to identify antiviral compounds. In the assay, hepatocytes or hepatogenic cells are infected with a virus, e.g., hepatitis B virus, and implanted into a specific mouse host to cause an initiation of viremia within the mouse. A compound is then administered to the mouse, and the effects of the compound on the resulting viral load or viral replication is determined. Such an assay is described in detail in Example 10.

In one embodiment, the assays uses a normal host mouse that is irradiated with an otherwise-lethal dose of gamma irradiation, and protected by the administration of bone marrow from an immune-restricted mouse, e.g., a NOD/SCID mouse. At the same time as the bone marrow is administered to the host mouse, or within 6-7 days after administration of bone marrow, a plurality of infected placental stem cell-derived hepatocytes or hepatogenic cells is administered to the host mouse, e.g., intraperitoneally, under the kidney capsule, into the host mouse liver, into the ear pinnae, etc. Within 6-20 days post-transplantation, a compound of interest is administered to the mouse. Such administration can be by any medically-acceptable route, but administration is preferably intraperitoneal or topical.

The host mouse can be assessed an any time after administration of the compound to determine, e.g., viral load in the serum, or for other indicia of viral presence or replication. In various embodiments, a tissue from the mouse is assayed for the presence of virions, e.g replicating forms of the virus. As above, viral levels can be determined using, e.g., one or more antibodies that recognize a viral antigen, e.g., hepatitis A virus surface antigen (antibodies available from AbD Serotec); hepatitis B virus HBsAg of HBeAg; hepatitis C virus core antigen; hepatitis D core antigen or hepatitis E core antigen. In a specific embodiment, for example, the presence of hepatitis B virus in a serum sample from a host mouse is detected using one or more antibodies to a hepatitis B virus envelope protein, surface antigen, or core antigen. In another embodiment, the level of virus in the infected cells is determined by quantitative or semi-quantitative PCR. In a specific embodiment, the primers used detect or are specific for a replicating form of the virus, e.g., are specific for the covalently closed circular form of HBV (cccHBV). In another specific embodiment, the primers used can amplify both cccHBV and the relaxed circular form of HBV.

5.7.8 Treatment of Cartilage Damage

In other embodiments, isolated placental stem cells, isolated populations of placental stem cells, and/or chondrocytic cells or chondrocytes differentiated therefrom, may be used in autologous or allogeneic tissue regeneration or replacement therapies or protocols, including, but not limited to repair of cartilage tissue. In a specific embodiment, placental stem cells can be used to heal or repair a disease, disorder or condition affecting cartilage, including trauma to cartilage (e.g., breaks, tears, etc.). In a more specific embodiment, the cartilage is articular cartilage. Placental stem cells can be administered to the cartilage directly, e.g., in a cell suspension, or can be administered to the cartilage in combination with a matrix, e.g., an electrospun nanofibrous scaffold, such as electrospun nanofibrous scaffolds described in Section 5.7.1.4, above. Placental stem cells contacted with (e.g., seeded onto) to the cartilage, with or without a scaffold, are preferably CD200, CD105$^+$, CD90$^+$, CD34, CD45$^-$ placental stem cells, but can be any of the placental stem cells described herein. All or a plurality of the placental stem cells used to treat a disease, disorder or condition in cartilage can be differentiated to chondrocytic cells prior to administration to the cartilage, or can be administered in an undifferentiated state. The chondrocytic cells or chondrocytes can be administered alone, or in combination with placental stem cells and/or another type of stem cell, in a cell suspension, or can be administered to the cartilage in combination with a matrix, e.g., an electrospun nanofibrous scaffold.

The effectiveness of a particular population of placental stem cells, alone or in combination with a scaffold, e.g., an electrospun nanofibrous scaffold, can be evaluated in an animal model that does not spontaneously heal a cartilage injury, e.g., a rabbit osteochondral defect model, e.g., as described in Example 14, below.

5.7.9 Uses of CD34$^+$, CD45$^-$ Placental Stem Cells

CD34$^+$, CD45$^-$ placental stem cells, and cell populations enriched for CD34$^+$, CD45$^-$ placental stem cells, provided herein can be used to treat an individual in need of hematopoietic stem cells, e.g., an individual in need of hematopoietic reconstitution, for example, after chemotherapy or myeloablation. In one embodiment, placental CD34$^+$CD45$^-$ stem cells alone are used to treat such an individual. In another embodiment, placental CD34$^+$CD45$^-$ stem cells are used in combination with, or to supplement, a second type of stem cell, or a second population of stem cells. Stem cells in such a second population can comprise hematopoietic stem cells, non-hematopoietic stem cells, or both. In one embodiment, the second population of stem cells comprises stem cells in cord blood. In another embodiment, the second population of stem cells comprises stem cells in bone marrow. In a specific embodiment, the stem cells are transplanted into the individual.

Typically, a patient receiving a stem cell infusion, for example for a bone marrow transplantation, receives one unit of nucleated cells, where a unit is approximately $1 \times 10^9$ nucleated cells (corresponding to $1\text{-}2 \times 10^6$ CD34$^+$ stem cells). Thus, in one embodiment, the number of nucleated cells, comprising CD34$^+$CD45$^-$ placental stem cells, administered to an individual, is at least five times the number of cells normally administered in a bone marrow replacement. In another specific embodiment of the method, the number of nucleated cells administered to an individual is at least ten times the number of cells normally administered in a bone marrow replacement. In another specific embodiment, the number of nucleated cells administered to an individual is at least fifteen times the number of cells normally administered in a bone marrow replacement. In another embodiment of the method, the total number of nucleated cells, which includes $CD34^+CD45^-$ placental stem cells, administered to an individual is between $1-1000\times10^8$ per kilogram of body weight.

In other embodiments, $CD34^+CD45^-$ placental stem cells, e.g., a cell population enriched in $CD34^+CD45^-$ placental stem cells, improves engraftment in an individual in need of stem cells, e.g., hematopoietic stem cells, compared to engraftment in an individual not receiving a population of hematopoietic stem cells enriched in $CD34^+CD45^-$ placental stem cells. In various embodiments, the engraftment is improved at least, or at, 1, 2, 3, 4, 5, 6, 7, 8, 9, 10, 11, 12, 13, 14, 15, 16, 17, 18, 19, 20 or 21 days post-transplant. In another more specific embodiment, $CD34^+CD45^-$ placental stem cells improve engraftment in an individual in need of stem cells at least, or at, more than 21 days post-transplant. In specific embodiments, $CD34^+CD45^-$ placental stem cells improves engraftment in an individual in need of stem cells at least, or at, more than 25, 30, 35, 40, 45, 50, 55 weeks, or 1 year or longer post-transplant.

The $CD34^+CD45^-$ placental stem cells, and populations of stem cells comprising such stem cells, can be prepared in a form that is easily administrable to an individual. For example, the cells or cell population can be contained within a container suitable for medical use. Such a container can be, for example, a sterile plastic bag, flask, jar, or other container from which the combined stem cell population can be easily dispensed. Preferably, the container is a container that allows, or facilitates, intravenous administration of a combined stem cell population. The container, e.g., bag, can hold the placenta-derived stem cells and stem cells from a second source together, e.g., as a mixed cell population, or can hold the two stem cell populations separately. In the latter embodiment, the bag preferably comprises multiple lumens or compartments that are interconnected to allow mixing of the placenta-derived stem cells and stem cells from a second source prior to, or during, administration. The container is preferably one that allows for cryopreservation of the combined stem cell population.

Thus, in one embodiment, provided herein is a composition comprising a $CD34^+CD45^-$ placental stem cell-enriched cell population in a container. In another embodiment, provided herein is a composition comprising a stem cell population, wherein said stem cell population comprises $CD34^+CD45^-$ placenta-derived stem cells and second type of stem cells in a container. In a specific embodiment, the container is a bag, flask, or jar. In a more specific embodiment, said placenta-derived stem cells and said second type of stem cells are contained together in said bag. In another more specific embodiment, said placenta-derived stem cells and said second type of stem cells from a second source are contained separately within said bag. In another specific embodiment, the composition comprises one or more compounds that facilitate cryopreservation of the combined stem cell population. In another specific embodiment, said combined stem cell population is contained within a physiologically-acceptable aqueous solution. In a more specific embodiment, said physiologically-acceptable aqueous solution is a 0.9% NaCl solution. In another more specific embodiment, said bag is a sterile plastic bag. In a more specific embodiment, said bag allows or facilitates intravenous administration of said stem cells. In another specific embodiment, the stem cells comprise $CD34^+CD45^-$ placental cells that are HLA-matched to said stem cells from a second source. In another specific embodiment, stem cells comprise $CD34^+CD45^-$ placental stem cells that are at least partially HLA-mismatched to the second type of stem cell. In another specific embodiment, said placenta-derived stem cells are derived from a plurality of donors. In another specific embodiment, said stem cells from a second source are derived from a plurality of donors.

$CD34^+CD45^-$ stem cells and cell populations comprising $CD34^+CD45^-$ placental stem cells can be cultured for a period of time prior to administration to an individual. For example, in one embodiment, the stem cells can be cultured in medium comprising Notch agonist, e.g., a deletion form of a Notch protein consisting essentially of the intracellular domain of the Notch protein, or a Delta protein. See U.S. 2004/0067583.

In another embodiment, a population of $CD34^+CD45^-$ placental stem cells provided herein and a population of umbilical cord blood cells are administered sequentially to a patient in need thereof. In one embodiment, the population of placental stem cells is administered first and the population of stem cells of a second type is administered second. In another embodiment, the stem cells of a second type are administered first and the $CD34^+CD45^-$ placental stem cells are administered second.

Combined populations of $CD34^+CD45^-$ placental stem cells, and stem cells of a second type, e.g., cord blood-derived stem or progenitor cells, or cord blood, including banked or cryopreserved cord blood, can be mixed, prior to transplantation, by any medically-acceptable means. In one embodiment, the two populations are physically mixed. In another embodiment of the method, populations are mixed immediately prior to (i.e., within 1, 2, 3, 4, 5, 7, 10 minutes of) administration to said individual. In another embodiment, populations are mixed at a point in time more than five minutes prior to administration to said individual. In another embodiment of the method, the $CD34^+CD45^-$ placental stem cells, and/or stem cells of a second type, are cryopreserved and thawed prior to administration to said individual. In another embodiment, stem cells are mixed at a point in time more than 1, 2, 3, 4, 5, 6, 7, 8, 9, 10, 11, 12, 13, 14, 15, 16, 17, 18, 19, 20, 21, 22, 23, or 24 hours prior to administration to said individual, wherein either or both of the populations of stem cells have been cryopreserved and thawed prior to said administration. In another embodiment, the stem cell populations may be administered more than once.

In another embodiment, the $CD34^+CD45^-$ placental stem cells and/or stem cells of a second type are preconditioned prior to transplantation. In a preferred embodiment, preconditioning comprises storing the cells in a gas-permeable container generally for a period of time at about $-5°$ C. to about 23° C., about 0° C. to about 10° C., or preferably about 4° C. to about 5° C. The cells may be stored between 18 hours and 21 days, between 48 hours and 10 days, preferably between 3-5 days. The cells may be cryopreserved prior to preconditioning or, may be preconditioned immediately prior to administration.

Either or both of the $CD34^+CD45^-$ placental stem cells, or stem cells of a second type, may be differentiated prior to contacting an individual in need of stem cells. For example, for contacting for the purpose of hematopoietic engraftment, the stem cells may be differentiated to cells in the hematopoietic lineage. In certain embodiments, the method of transplantation of stem cell populations comprises (a) induction of differentiation of the CD34$^+$CD45$^-$ placental stem cells, (b) mixing the placental stem cells with a population of stem cells of a second type, e.g., cord blood stem cells, to form a combined cell population, and (c) administration of the combined cell population to an individual in need thereof. In another embodiment the method of transplantation comprises (a) induction of differentiation of stem cells of a second type; (b) mixing the differentiated cells with CD34$^+$CD45$^-$ placental stem cells to form a combined cell population; and (c) administration of the combined cell population to an individual in need thereof. In another embodiment, the method of transplantation of combined stem cell populations comprises (a) mixing CD34$^+$CD45$^-$ placental stem cells with a population of cord blood cells; (b) induction of differentiation of the mixture of the cord blood cells and CD34$^+$CD45$^-$ placental stem cells and (c) administration of the mixture to a patient in need thereof.

The stem cell populations provided herein, enriched for CD34$^+$CD45$^-$ placental stem cells, may be transplanted into a patient in any pharmaceutically or medically acceptable manner, including by injection, e.g., intravenous injection, intramuscular injection, intraperitoneal injection, intraocular injection, direct injection into a particular tissue, transfusion, etc. For example, combined stem cell populations, e.g., placental stem cells in combination with cord blood-derived stem cells) may be transplanted by intravenous infusion. In another embodiment, a combined stem cell population comprising placental stem cells and cardiac stem cells, in suspension, may be injected directly into cardiac tissue, e.g., an ischemic area in a heart. The combined stem cell populations may comprise, or be suspended in, any pharmaceutically-acceptable carrier. The combined stem cell populations may be carried, stored, or transported in any pharmaceutically or medically acceptable container, for example, a blood bag, transfer bag, plastic tube or vial.

After transplantation, engraftment in a human recipient may be assessed using, e.g., nucleic acid or protein detection or analytical methods. For example, the polymerase chain reaction (PCR), STR, SSCP, RFLP analysis, AFLP analysis, and the like, may be used to identify engrafted cell-specific nucleotide sequences in a tissue sample from the recipient. Such nucleic acid detection and analysis methods are well-known in the art. In one embodiment, engraftment may be determined by the appearance of engrafted cell-specific nucleic acids in a tissue sample from a recipient, which are distinguishable from background. The tissue sample analyzed may be, for example, a biopsy (e.g., bone marrow aspirate) or a blood sample.

In one embodiment, a sample of peripheral blood is taken from a patient immediately prior to a medical procedure, e.g., myeloablation. After the procedure, a combined stem cell as provided herein is administered to the patient. At least once post-administration, a second sample of peripheral blood is taken. An STR profile is obtained for both samples, e.g., using PCR primers for markers (alleles) available from, e.g., LabCorp (Laboratory Corporation of America). A difference in the number or characteristics of the markers (alleles) post-administration indicates that engraftment has taken place.

Engraftment can also be demonstrated by detection of re-emergence of neutrophils.

In another example, engrafted cell-specific markers may be detected in a tissue sample from the recipient using antibodies directed to markers specific to either the transplanted stem cells, or cells into which the transplanted stem cells would be expected to differentiate. In one embodiment, engraftment of a combination of placental stem cells and cord blood-derived stem cells may be assessed by FACS analysis to determine the presence of CD45$^+$, CD19$^+$, CD33$^+$, CD7$^+$ and/or CD3$^+$ cells by adding the appropriate antibody and allowing binding; washing (e.g., with PBS); fixing the cells (e.g., with 1% paraformaldehyde); and analyzing on an appropriate FACS apparatus (e.g., a FACSCalibur flow cytometer (Becton Dickinson)). Where placental stem cells and/or stem cells from a second source are from an individual of a different sex than a recipient, e.g., male donor and female recipient, engraftment can be determined by detection of sex-specific markers, e.g., Y-chromosome-specific markers. Placental stem cells and/or stem cells from a second source may also be genetically modified to express a unique marker or nucleic acid sequence that facilitates identification, e.g., an RFLP marker, expression of β-galactosidase or green fluorescent protein, or the like.

The degree of engraftment may be assessed by any means known in the art. In one embodiment, the degree of engraftment is assessed by a grading system as follows, which uses a thin section of fixed and antibody-bound tissue from the transplant recipient. In this example grading system, engraftment is graded as follows: 0=no positive cells (that is, no cells bound by an antibody specific to an engrafted cell); 0.5=one or two positive cells, perhaps positive, but difficult to differentiate from background or non-specific staining; 1=2-20 scattered positive cells; 2=approximately 20-100 scattered or clustered positive cells throughout the tissue; 3=more than 100 positive cells comprising less than 50% of the tissue; 4=more than 50% of cells are positive. In specific embodiments, engraftment is determined where greater than 0.5%, 1%, 2%, 3%, 4%, 5%, 7.5%, 10%, 15%, 20% or greater of the cells are positively stained.

In another embodiment, the degree of engraftment is determined by analysis of the gain of one or more biological functions carried out by the engrafted cells. For example, where a recipient, who has undergone myeloablative therapy, receives a transplant of a combined stem cell population comprising placental stem cells and cord blood-derived stem cells, the degree of engraftment may be determined by the degree to which normal hematopoiesis, blood cell populations and blood function return to normal.

Where the combined stem cell population in whole or in part is HLA-mismatched to an intended recipient, it may be necessary to treat the recipient to reduce immunological rejection of the donor cells. Methods for reducing immunological rejection are disclosed in, e.g., U.S. Pat. Nos. 5,800,539 and 5,806,529, both of which are incorporated herein by reference.

In one embodiment, therefore, combined stem cell populations comprising hematopoietic stem cells can be used to treat patients having a blood cancer, such as a lymphoma, leukemia (such as chronic or acute myelogenous leukemia, acute lymphocytic leukemia, Hodgkin's disease, etc.), myelodysplasia, myelodysplastic syndrome, and the like. In another embodiment, the disease, disorder or condition is chronic granulomatous disease.

Because hematopoietic reconstitution can be used in the treatment of anemias, further provided herein is the treatment of an individual with CD34$^+$CD45$^-$ placental stem cells of the invention, wherein the individual has an anemia or disorder of the blood hemoglobin. The anemia or disorder may be natural (e.g., caused by genetics or disease), or may be artificially-induced (e.g., by accidental or deliberate poisoning, chemotherapy, and the like). In another embodiment, the disease or disorder is a marrow failure syndrome (e.g., aplastic anemia, Kostmann syndrome, Diamond-Blackfan anemia, amegakaryocytic thrombocytopenia, and the like), a bone marrow disorder or a hematopoietic disease or disorder. In a specific embodiment, the $CD34^+CD45^-$ placental stem cells are administered with a plurality of mesenchymal stem cells and/or a plurality of adherent placental stem cells.

In another embodiment, the $CD34^+CD45^-$ placental stem cells provided herein can be introduced, alone or in combination with a second type of stem cell, e.g., a mesenchymal stem cell or an adherent placental stem cell, into a damaged organ for organ neogenesis and repair of injury in vivo. Such injury may be due to conditions and disorders including, but not limited to, myocardial infarction, seizure disorder, multiple sclerosis, stroke, hypotension, cardiac arrest, ischemia, inflammation, age-related loss of cognitive function, cerebral palsy, neurodegenerative disease, Alzheimer's disease, Parkinson's disease, Leigh disease, AIDS dementia, memory loss, amyotrophic lateral sclerosis, ischemic renal disease, brain or spinal cord trauma, heart-lung bypass, glaucoma, retinal ischemia, or retinal trauma.

In other embodiments, the disease, disorder or condition includes, but is not limited to lysosomal storage diseases, such as Tay-Sachs, Niemann-Pick, Fabry's, Gaucher's disease (e.g., glucocerebrosidase deficiency), Hunter's, and Hurler's syndromes, Maroteaux-Lamy syndrome, fucosidosis (fucosidase deficiency), Batten disease (CLN3), as well as other gangliosidoses, mucopolysaccharidoses, and glycogenoses.

In other embodiments, the $CD34^+CD45^-$ placental stem cells provided herein can be used as autologous or heterologous transgene carriers in gene therapy to correct, for example, inborn errors of metabolism, adrenoleukodystrophy (e.g., co-A ligase deficiency), metachromatic leukodystrophy (arylsulfatase A deficiency) (e.g., symptomatic, or presymptomatic late infantile or juvenile forms), globoid cell leukodystrophy (Krabbe's disease; galactocerebrosidase deficiency), acid lipase deficiency (Wolman disease), cystic fibrosis, glycogen storage disease, hypothyroidism, sickle cell anemia, thalassemia (e.g., beta thalassemia), Pearson syndrome, Pompe's disease, phenylketonuria (PKU), porphyrias, maple syrup urine disease, homocystinuria, mucoplysaccharidosis, chronic granulomatous disease and tyrosinemia and Tay-Sachs disease or to treat solid tumors or other pathological conditions.

In other embodiments, the disease, disorder or condition is a disease, disorder or condition requiring replacement or repair of one or more tissues. For example, the CD34 CD45 placental stem cells provided herein, alone or in combination with a second type of stem cell, e.g., a mesenchymal stem cell or an adherent placental stem cell, can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair. The combined stem cell populations provided herein can also be used for augmentation, repair or replacement of, e.g., cartilage, tendon, or ligaments. For example, in certain embodiments, prostheses (e.g., hip prostheses) are coated with replacement cartilage tissue constructs grown from combined stem cell populations provided herein. In other embodiments, joints (e.g., knee) are reconstructed with cartilage tissue constructs grown from combined stem cell populations. Cartilage tissue constructs can also be employed in major reconstructive surgery for different types of joints (for protocols, see e.g., Resnick, D., and Niwayama, G., eds., 1988, DIAGNOSIS OF BONE AND JOINT DISORDERS, 2D ED., W. B. Saunders Co.). The combined stem cell populations can be used to repair damage of tissues and organs resulting from trauma, metabolic disorders, or disease. In one embodiment, a patient can be administered a combined stem cell population to regenerate or restore tissues or organs which have been damaged as a consequence of disease, e.g., to repair heart tissue following myocardial infarction.

In another embodiment, the $CD34^+CD45^-$ placental stem cells provided herein, alone or in combination with a second type of stem cell, e.g., a mesenchymal stem cell or an adherent placental stem cell, may be used to treat an individual who has received a lethal or sub-lethal dose of radiation. Such radiation may be accidentally received, for example in a nuclear incident, whether work- or aggression-related, or therapeutic, for example, as part of a medical procedure. The particular type of radiation (e.g., alpha, beta, gamma) is not critical. The combined stem cell populations provided herein may be used to ameliorate one or more symptoms of radiation sickness, for example, nausea, loss of appetite, lethargy, dyspnea, decreased white blood cell count, chronic anemia, fatigue, weakness, paleness, difficulty breathing, feelings of malaise, and the like, whether such symptoms are indicative of recoverable or fatal radiation sickness. In another embodiment, the individual has one or more symptoms associated with acute radiation syndrome (ARS). The combined stem cell populations provided herein may also be used to partially or fully reconstitute the hematopoietic system of an individual that has received a lethal or sub-lethal dose of radiation, such that the individual becomes partially or fully chimeric. Such chimerism may be temporary or permanent (e.g., may persist for 1, 2, 3 weeks, or 1, 2, 3, 4, 5, 6, 7, 8, 9, 10, 11 months or longer). In a preferred embodiment, a combined stem cell population provided herein is provided to the individual within the first 24 hours after exposure. The individual may be administered a combined stem cell population within the first hour, 2 hours, 3 hours, 4 hours, 5 hours, 6 hours, 9 hours, 12 hours, 15 hours, 18 hours, or 21 hours after exposure to radiation. A combined stem cell population as provided herein may also be administered within 2 days, 3 days, 4 days, 5 days, 6 days, one week, 2 weeks, 3 weeks, 4 weeks or 5 weeks after exposure to radiation.

Therapeutic or prophylactic treatment of an individual with the $CD34^+CD45^-$ placental stem cells provided herein may be considered effective if the disease, disorder or condition is measurably improved in any way. Such improvement may be shown by a number of indicators. Measurable indicators include, for example, detectable changes in a physiological condition or set of physiological conditions associated with a particular disease, disorder or condition (including, but not limited to, blood pressure, heart rate, respiratory rate, counts of various blood cell types, levels in the blood of certain proteins, carbohydrates, lipids or cytokines or modulation expression of genetic markers associated with the disease, disorder or condition). Treatment of an individual with the $CD34^+CD45^-$ placental stem cells provided herein would be considered effective if any one of such indicators responds to such treatment by changing to a value that is within, or closer to, the normal value. The normal value may be established by normal ranges that are known in the art for various indicators, or by comparison to such values in a control. Introduction of a combined stem cell population as provided herein for the purposes of engraftment, e.g., hematopoietic engraftment, would be considered successful if the individual to whom the combined stem cell population is introduced exhibits any indications of engraftment (e.g., markers of engrafted cells appearing in biopsy or tissue samples, or blood sample; detection of one or more biochemical functions performed by the engrafted cells, etc.). In medical science, the efficacy of a treatment is also often characterized in terms of an individual's impressions and subjective feeling of the individual's state of health. Improvement therefore may also be characterized by subjective indicators, such as the individual's subjective feeling of improvement, increased well-being, increased state of health, improved level of energy, or the like, after administration of the stem cells or supplemented cell populations provided herein.

6. EXAMPLES

6.1 Example 1: Obtaining Placental Stem Cells

6.1.1 Tissue Disruption/Enzymatic Digestion

An exemplary protocol for obtaining stem cells from placental tissue by enzymatic digestion is as follows. Frozen placental tissue (three pieces of approximately ~1×1×0.5 cm each) is obtained. The tissue is umbilical cord, maternal surface of the placenta, or amniotic membrane. Digestive enzymes used include trypsin-EDTA (0.25%, GIBCO BRL); collagenase IA (Sigma), collagenase I (Worthington), collagenase 1A (Sigma)+Trypsin-EDTA, collagenase 1 (Worthington)+Trypsin-EDTA, or Elastase+Collagenase I+Collagenase IV+Daspase (Worthington). Digestion of placental tissue is as follows. Tissue is minced in the presence of enzymes (1 g in 10 ml in 50 ml tube) at 37° C., 250 rpm shaking, tube position at 45° angle for 1 hr (C25 Incubator Shaker, New Brunswick Scientific, Edison, N.J., USA). The supernatant is then discarded. The pellet is washed with 20 ml Hank's+5% FCS (3 times), and re-suspended in 12 ml culture medium. 3 ml of the resulting suspension are aliquoted into T-75 flasks containing 10 ml culture medium each (four flasks per digestion). Optionally, 10 ml Trypsin/EDTA is added for 30 min at 37° C., with shaking at 250 rpm, with recentrifugation and an additional wash with 10 ml Hank's+5% FCS. Cells are plated and cultured, selecting for adherent cells.

The following method may also be used. A placenta is obtained less than 24 hours after expulsion. After cleaning the placenta, a hemostat is clamped to the distal end of the umbilical cord. The umbilical cord is cut at the junction with the placenta and transferred to a sterile dish. After cutting the cord below the hemostat, the cord is massaged to remove blood clots, and transferred to 500 ml PBS containing gentamicin and amphotericin B. 5 g of this cord is used. A scalpel is used to trim the remaining placental material by cutting in a radius of about 3 inches from the umbilical cord attachment point. Blood clots are forced from the remaining material, and 5 g of the amnion-chorion, centered at the umbilical cord root, is transferred to the same container as the umbilical cord. The umbilical cord and amnion-chorion tissue is sliced, then minced to pieces about 1 mm³ in size. The tissue is then digested with 1 mg/ml Collagenase 1A (20 ml/g tissue) for 1 hour at 37□C followed by Trypsin-EDTA (10 ml/g tissue) for 30 minutes at 37□C. After three washes in 5% FBS in PBS, the tissue is resuspended in culture medium (20 ml/g tissue) and transferred to T flasks at about 0.22 ml/cm².

6.1.2 Perfusion

A post-partum placenta is obtained within 24 hours after birth. The umbilical cord is clamped with an umbilical cord clamp approximately 3 to 4 inches about the placental disk, and the cord is cut above the clamp. The umbilical cord is either discarded, or processed to recover, e.g., umbilical cord stem cells, and/or to process the umbilical cord membrane for the production of a biomaterial. Excess amniotic membrane and chorion is cut from the placenta, leaving approximately ¼ inch around the edge of the placenta. The trimmed material is discarded.

Starting from the edge of the placental membrane, the amniotic membrane is separated from the chorion using blunt dissection with the fingers. When the amniotic membrane is entirely separated from the chorion, the amniotic membrane is cut around the base of the umbilical cord with scissors, and detached from the placental disk. The amniotic membrane can be discarded, or processed, e.g., to obtain stem cells by enzymatic digestion, or to produce, e.g., an amniotic membrane biomaterial.

The fetal side of the remaining placental material is cleaned of all visible blood clots and residual blood using sterile gauze, and is then sterilized by wiping with an iodine swab than with an alcohol swab. The umbilical cord is then clamped crosswise with a sterile hemostat beneath the umbilical cord clamp, and the hemostat is rotated away, pulling the cord over the clamp to create a fold. The cord is then partially cut below the hemostat to expose a cross-section of the cord supported by the clamp. Alternatively, the cord is clamped with a sterile hemostat. The cord is then placed on sterile gauze and held with the hemostat to provide tension. The cord is then cut straight across directly below the hemostat, and the edge of the cord near the vessel is re-clamped.

The vessels exposed as described above, usually a vein and two arteries, are identified, and opened as follows. A closed alligator clamp is advanced through the cut end of each vessel, taking care not to puncture the clamp through the vessel wall. Insertion is halted when the tip of the clamp is slightly above the base of the umbilical cord. The clamp is then slightly opened, and slowly withdrawn from the vessel to dilate the vessel.

Plastic tubing, connected to a perfusion device or peristaltic pump, is inserted into each of the placental arteries. Plastic tubing, connected to a 250 mL collection bag, is inserted into the placental vein. The tubing is taped into place.

A small volume of sterile injection grade 0.9% NaCl solution to check for leaks. If no leaks are present, the pump speed is increased, and about 750 mL of the injection grade 0.9% NaCl solution is pumped through the placental vasculature. Perfusion can be aided by gently massaging the placental disk from the outer edges to the cord. When a collection bag is full, the bag is removed from the coupler connecting the tubing to the bag, and a new bag is connected to the tube.

When collection is finished, the collection bags are weighed and balanced for centrifugation. After centrifugation, each bag is placed inside a plasma extractor without disturbing the pellet of cells. The supernatant within the bags is then removed and discarded. The bag is then gently massaged to resuspend the cells in the remaining supernatant. Using a sterile 1 mL syringe, about 300-500 µL of cells is withdrawn from the collection bag, via a sampling site coupler, and transferred to a 1.5 mL centrifuge tube. The weight and volume of the remaining perfusate are determined, and ⅓ volume of hetastarch is added to the perfusate and mixed thoroughly. The number of cells per mL is determined. Red blood cells are removed from the perfusate using a plasma extractor.

Placental cells are then immediately cultured to isolate placental stem cells, or are cryopreserved for later use.

6.1.3 Culture of Isolated Stem Cells

Primary Culture:

The purpose of primary culture is to establish cells from digested placental tissue. The digested tissue is suspended in culture medium and placed into Corning T-flasks, which are incubated in a humidified chamber maintained at 37° C. with 5% $CO_2$. Half of the medium is replenished after 5 days of culture. High-density colonies of cells form by 2 weeks of culture. Colonies are harvested with Trypsin-EDTA, which is then quenched with 2% FBS in PBS. Cells are centrifuged and resuspended in culture medium for seeding expansion cultures. These cells are defined as Passage 0 cells having doubled 0 times.

Expansion Culture:

Cells harvested from primary culture, harvested from expansion culture, or thawed from the cell bank are used to seed expansion cultures. Cell Factories (NUNC™) are treated with 5% $CO_2$ in air at 50 ml/min/tray for 10 min through a sterile filter and warmed in a humidified incubator maintained at 37° C. with 5% $CO_2$. Cell seeds are counted on a hemacytometer with trypan blue, and cell number, viability, passage number, and the cumulative number of doublings are recorded. Cells are suspended in culture medium to about $2.3 \times 10^4$ cells/ml and 110 ml/tray are seeded in the Cell Factories. After 3-4 days and again at 5-6 days of culture, culture medium is removed and replaced with fresh medium, followed by another treatment with 5% $CO_2$ in air. When cells reach approximately 10 cells/$cm^2$, cells are harvested with Trypsin-EDTA, followed by quenching with 2% FBS in PBS. Cell are then centrifuged and resuspended in culture medium.

6.2 Example 2: Isolation and Characterization of Placental Stem Cells from Perfusate This Example demonstrates the collection and characterization of placental stem cells from several different perfusion experiments.

Materials and Methods

Placenta donors were recruited from expectant mothers that enrolled in private umbilical cord blood banking programs and provided informed consent permitting the use of the exsanguinated placenta following recovery of cord blood for research purposes. These donors also permitted use of blinded data generated from the normal processing of their umbilical cord blood specimens for cryopreservation. This allowed comparison between the composition of the collected cord blood and the effluent perfusate recovered using this experimental method described below. All donor data was kept confidential.

Following exsanguination of the umbilical cord and placenta, the placenta was placed in a sterile, insulated container at room temperature and delivered to the laboratory within 4 hours of birth. Placentas were discarded if, on inspection, they had evidence of physical damage such as fragmentation of the organ or avulsion of umbilical vessels. Placentas were maintained at room temperature (23±2° C.) or refrigerated (4° C.) in sterile containers for 2 to 20 hours. Periodically, the placentas were immersed and washed in sterile saline at 25±3° C. to remove any visible surface blood or debris. The umbilical cord was transected approximately 5 cm from its insertion into the placenta and the umbilical vessels were cannulated with Teflon or polypropylene catheters connected to a sterile fluid path allowing bidirectional perfusion of the placenta and recovery of the effluent fluid.

Placental Conditioning

Placentas were obtained from delivery rooms along with cord blood after obtaining written parental consent, and were processed at room temperature within 12 to 24 hours after delivery. Before processing, the membranes were removed and the maternal site washed clean of residual blood. The placenta was maintained under varying conditions in an attempt to simulate and sustain a physiologically compatible environment for the proliferation and recruitment of residual cells. The umbilical vessels were cannulated with catheters made from 20 gauge Butterfly needles use for blood sample collection. The cannula was flushed with IMDM serum-free medium (GibcoBRL, NY) containing 2 U/ml heparin (EJkins-Sinn, N.J.). Placentas were then perfused with heparinized (2 U/mL) Dulbecco's modified Eagle Medium (DMEM) at the rate of 15 mL/minute for 10 minutes and the perfusates were collected from the maternal sites within one hour and the nucleated cells counted. Perfusion of the placenta continued at a rate of 50 mL per minute until approximately 150 mL of perfusate was collected. This volume of perfusate was labeled "early fraction". The perfusion and collection procedures were repeated once or twice until the number of recovered nucleated cells fell below 100/microL. Continued perfusion of the placenta at the same rate resulted in the collection of a second fraction of approximately 150 mL and was labeled "late fraction". During the course of the procedure, the placenta was gently massaged to aid in the perfusion process and assist in the recovery of cellular material. Effluent fluid was collected from the perfusion circuit by both gravity drainage and aspiration through the arterial cannula.

The perfusates were pooled and subjected to light centrifugation to remove platelets, debris and denucleated cell membranes. The nucleated cells were then isolated by Ficoll-Hypaque density gradient centrifugation and after washing, resuspended in DMEM. For isolation of the adherent cells, aliquots of $5-10 \times 10^6$ cells were placed in each of several T-75 flasks and cultured with commercially available Mesenchymal Stem Cell Growth Medium (MSCGM) obtained from BioWhittaker, and placed in a tissue culture incubator (37° C., 5% $CO_2$). After 10 to 15 days, non-adherent cells were removed by washing with PBS, which was then replaced by MSCGM. The flasks were examined daily for the presence of various adherent cell types and in particular, for identification and expansion of clusters of adherent fibroblastoid cells.

Cell Recovery and Isolation

Cells were recovered from the perfusates by centrifugation at 400×g for 15 minutes at room temperature. The cell pellets were resuspended in IMDM serum-free medium containing 2 U/ml heparin and 2 mM EDTA (GibcoBRL, NY). The total mononuclear cell fraction was isolated using LYMPHOPREP™ (Nycomed Pharma, Oslo, Norway) according to the manufacturer's recommended procedure and the mononuclear cell fraction was resuspended. Cells were counted using a hemocytometer. Viability was evaluated by trypan blue exclusion. Isolation of mesenchymal cells was achieved by differential trypsinization using a solution of 0.05% trypsin with 0.2% EDTA (Sigma). Differential trypsinization was possible because fibroblastoid cells, including adherent placental stem cells, detached from plastic surfaces within about five minutes whereas other adherent populations required more than 20-30 minutes incubation.

The detached fibroblastoid cells were harvested following trypsinization and trypsin neutralization, using Trypsin Neutralyzing Solution (TNS, BioWhitaker). The cells were washed in DMEM and resuspended in MSCGM. Flow cytometry was carried out using a Becton-Dickinson FACSCalibur instrument and FITC and PE labeled monoclonal antibodies, selected on the basis of known markers for bone marrow-derived MSC (mesenchymal stem cells), including antibodies to CD10, CD34, CD44, CD45 and CD90. Antibodies were purchased from Becton-Dickinson and Caltag laboratories (South San Francisco, Calif.), and SH2, SH3 and SH4 antibody-producing hybridomas were obtained from the American Type Culture Collection. Reactivities of the MoAbs in their cultured supernatants were detected by FITC or PE labeled F(ab)'$_2$ goat anti-mouse antibodies. Lineage differentiation was carried out using the commercially available induction and maintenance culture media (BioWhittaker), used as per manufacturer's instructions.

Isolation of Placental Stem Cells

Microscopic examination of the adherent cells in the culture flasks revealed morphologically different cell types, including spindle-shaped cells; round cells with large nuclei and numerous perinuclear small vacuoles; and star-shaped cells with several projections, through one of which the cells were attached to the flask. Although no attempts were made to further characterize these adherent cells, similar cells were observed in the culture of bone marrow, cord and peripheral blood, and therefore considered to be non-stem cell in nature.

Fibroblastoid adherent cells, appearing as clusters, were similar in appearance to mesenchymal stem cells (MSC), and were isolated by differential trypsinization and subcultured in secondary flasks. The cells appeared rounded after trypsinization. Phase microscopy of the rounded cells, after trypsinization, showed the cells to be highly granulated and similar to bone marrow-derived MSC produced in the laboratory or purchased from commercial sources, e.g., BioWhittaker. When subcultured, the adherent placental cells, in contrast to their earlier phase, adhered within hours, assumed the characteristic fibroblastoid shape, and formed a growth pattern similar to the reference bone marrow-derived MSC. Moreover, during subculturing and refeeding, loosely bound mononuclear cells were washed out and the cultures remained homogeneous and devoid of any visible non-fibroblastoid cell contaminants.

Flow Cytometry

The expression of CD34, CD38, SH2, SH3, SH4 and other stem cell-associated surface markers on early and late fraction purified mononuclear cells was assessed by flow cytometry. In a specific case, cells were washed in PBS and then double-stained with anti-CD34 phycoerythrin and anti-CD38 fluorescein isothiocyanate (Becton Dickinson, Mountain View, Calif.).

In separate experiments, placental stem cells obtained from separate perfusions, designated PLSC-1 through PLSC-29, were assessed for the expression of CD10, CD29, CD34, CD44, CD45, CD54, CD90, SH2 (CD105), SH3 (CD73), SH4 (CD73) and HLA-1 by flow cytometry. Adherent cells designated PLSC-1 to PLSC-3, PLSC-5 to PLSC-10, PLSC-15 to PLSC-21, PLSC-23, PLSC-26 and PLSC-27 were found to be positive for CD10, CD29, CD54, SH2, SH3 and SH4, and negative for CD34 and CD45. Adherent cells designated PLSC-15 to PLSC-21, PLSC-23, PLSC-26 and PLSC-27 were additionally found to be positive for CD44, CD90 and HLA1. See Table 1, below.

mRNA was collected from adherent cells from PLSC-3 and PLCS-6 to PLSC-10 cells, and rtPCR was performed using primers specific to OCT-4 (POU5F). All of the cell populations tested were positive for OCT-4 mRNA.

TABLE 1

Characterization of placental stem cells (PLSC) collected from separate perfusion experiments.

| ID # | Medium | Frozen (Vials) | CD34 | CD45 | CD10 | CD29 | CD54 | SH2 | SH3 | SH4 | SSEA4 | CD44 | HLA1 | CD90 | Oct4 |
|---|---|---|---|---|---|---|---|---|---|---|---|---|---|---|---|
| PLSC-1 | BW | Y (2) | − | − | + | + | + | + | + | + | | | | | |
| PLSC-2 | BW | Y (6) | − | − | + | + | + | + | + | + | | | | | |
| PLSC-3 | BW | Y (2) | − | − | + | + | + | + | + | + | | | | | + |
| PLSC-4 | BW | None | | | | | | | | | | | | | |
| PLSC-5 | BW | Y (9) | − | − | + | + | + | + | + | + | | | | | |
| PLSC-6 | BW | Y (26) | − | − | +/low | + | + | + | + | + | | | | | + |
| PLSC-7 | BW | Y (2) | − | − | + | + | + | + | + | + | | | | | + |
| PLSC-8 | BW | Y (10) | − | − | + | + | + | + | + | + | | | | | + |
| PLSC-9 | BW | Y (11) | − | − | + | + | + | + | + | + | | | | | + |
| PLSC-10 | BW | Y (10) | − | − | + | + | + | + | + | + | | | | | + |
| PLSC-11 | D-5% FCS | Y (9) | | | | | | | | | | | | | |
| PLSC-12 | D-5% FCS | Y (7) | | | | | | | | | | | | | |
| PLSC-13 | D-5% FCS | Y (5) | | | | | | | | | | | | | |
| PLSC-14 | D-5% FCS | Y (9) | | | | | | | | | | | | | |
| PLSC-15 | Anthro-1 | Y (7) | − | − | + | + | + | + | + | + | | + | + | + | |
| PLSC-16 | Anthro-1 | Y (8) | − | − | + | + | + | + | + | + | | + | + | + | |
| PLSC-17 | Anthro-1 | Y (8) | − | − | + | + | + | + | + | + | | + | + | + | |
| PLSC-18 | Anthro-1 | Y (8) | − | − | + | + | + | + | + | + | | + | + | + | |
| PLSC-19 | BWtoA | Y (17) | − | − | + | + | + | + | + | + | | + | + | + | |
| PLSC-20 | BWtoA | Y (40) | − | − | + | + | + | + | + | + | | + | + | + | |
| PLSC-21 | BWtoA | Y (9) | − | − | + | + | + | + | + | + | +/− | + | + | + | |
| PLSC-22 | BWtoA | FTE | | | | | | | | | | | | | |
| PLSC-23 | Anthro-1 | Y (10) | − | − | + | + | + | + | + | + | | + | + | + | |
| PLSC-24 | Anthro-1 | FTE | | | | | | | | | | | | | |
| PLSC-25 | Anthro-1 | FTE | | | | | | | | | | | | | |
| PLSC-26 | Anthro-1 | Y (15) | − | − | + | + | + | + | + | + | | + | + | + | |
| PLSC-27 | Anthro-1 | Y (25) | − | − | + | + | + | + | + | + | | + | + | + | |

+: Detected by flow cytometry, or, for OCT-4, gene expression detected by RT-PCR.
−: Not detected.
Blank: Presence of marker was not tested.
FTE: Failed to expand.
BW—BioWhittaker complete medium (RPMI 1640 + 10% FBS).
D-5% FCS: DMEM-5% FCS.
BWtoA: BW to Anthro-1 medium Differentiation In separate experiments, the adherent fibroblastoid cells were demonstrated to be stem cells. The cells were differentiated in vitro into cells of adipocytic lineage, as evidenced by the formation of oil droplets detectable by the stain Oil Red. The cells were also differentiated in vitro into cells of a neurogenic lineage as evidenced by the development of dendrite-like spindles characteristic of neural cells, and the appearance of glial acid fibrillary protein and neurofilament proteins, both markers of neural cells. The cells were also differentiated in vitro into cells of a chondrogenic lineage, as evidenced by the appearance of glycosaminoglycans, produced by cartilage-producing cells, that were detectable by Periodic Acid Schiff reagent. In a separate experiment, it was determined that placental stem cells did not differentiate in a NOD-SCID mouse model.

6.3 Example 3: Isolation of Placental Stem Cells from Placental Structures

6.3.1 Materials & Methods 6.3.1.1 Isolation of Populations of Placental Cells Comprising Placental Stem Cells Distinct populations of placental cells were obtained from the placentas of normal, full-term pregnancies. All donors provided full written consent for the use of their placentas for research purposes. Placental stem cells were obtained from the following sources: (1) placental perfusate (from perfusion of the placental vasculature); and enzymatic digestions of (2) amnion, (3) chorion, (4) amnion-chorion plate, and (5) umbilical cord. The various placental tissues were cleaned in sterile PBS (Gibco-Invitrogen Corporation, Carlsbad, Calif.) and placed on separate sterile Petri dishes. The various tissues were minced using a sterile surgical scalpel and placed into 50 mL Falcon Conical tubes. The minced tissues were digested with 1× Collagenase (Sigma-Aldrich, St. Louis, Mo.) for 20 minutes in a 37° C. water bath, centrifuged, and then digested with 0.25% Trypsin-EDTA (Gibco-Invitrogen Corp) for 10 minutes in a 37° C. water bath. The various tissues were centrifuged after digestion and rinsed once with sterile PBS (Gibco-Invitrogen Corp). The reconstituted cells were then filtered twice, once with 100 μm cell strainers and once with 30 μm separation filters, to remove any residual extracellular matrix or cellular debris.

6.3.1.2 Cellular Viability Assessment and Cell Counts

The manual trypan blue exclusion method was employed post digestion to calculate cell counts and assess cellular viability. Cells were mixed with Trypan Blue Dye (Sigma-Aldrich) at a ratio of 1:1, and the cells were read on hemacytometer.

6.3.1.3 Cell Surface Marker Characterization

Cells that were HLA ABC$^-$/CD45$^-$/CD34$^-$/CD133$^+$ were selected for characterization. Cells having this phenotype were identified, quantified, and characterized by two of Becton-Dickinson flow cytometers, the FACSCalibur and the FACS Aria (Becton-Dickinson, San Jose, Calif., USA). The various placental cells were stained, at a ratio of about 10 μL of antibody per 1 million cells, for 30 minutes at room temperature on a shaker. The following anti-human antibodies were used: Fluorescein Isothiocyanate (FITC) conjugated monoclonal antibodies against HLA-G (Serotec, Raleigh, N.C.), CD10 (BD Immunocytometry Systems, San Jose, Calif.), CD44 (BD Biosciences Pharmingen, San Jose, Calif.), and CD105 (R&D Systems Inc., Minneapolis, Minn.); Phycoerythrin (PE) conjugated monoclonal antibodies against CD44, CD200, CD117, and CD13 (BD Biosciences Pharmingen); Phycoerythrin-Cy5 (PE Cy5) conjugated Streptavidin and monoclonal antibodies against CD117 (BD Biosciences Pharmingen); Phycoerythrin-Cy7 (PE Cy7) conjugated monoclonal antibodies against CD33 and CD10 (BD Biosciences); Allophycocyanin (APC) conjugated streptavidin and monoclonal antibodies against CD38 (BD Biosciences Pharmingen); and Biotinylated CD90 (BD Biosciences Pharmingen). After incubation, the cells were rinsed once to remove unbound antibodies and were fixed overnight with 4% paraformaldehyde (USB, Cleveland, Ohio) at 4° C. The following day, the cells were rinsed twice, filtered through a 30 μm separation filter, and were run on the flow cytometer(s).

Samples that were stained with anti-mouse IgG antibodies (BD Biosciences Pharmingen) were used as negative controls and were used to adjust the Photo Multiplier Tubes (PMTs). Samples that were single stained with anti-human antibodies were used as positive controls and were used to adjust spectral overlaps/compensations.

6.3.1.4 Cell Sorting and Culture

One set of placental cells (from perfusate, amnion, or chorion), prior to any culture, was stained with 7-Amino-Actinomycin D (7AAD; BD Biosciences Pharmingen) and monoclonal antibodies specific for the phenotype of interest. The cells were stained at a ratio of 10 μL of antibody per 1 million cells, and were incubated for 30 minutes at room temperature on a shaker. These cells were then positively sorted for live cells expressing the phenotype of interest on the BD FACS Aria and plated into culture. Sorted (population of interest) and "All" (non-sorted) placental cell populations were plated for comparisons. The cells were plated onto a fibronectin (Sigma-Aldrich) coated 96 well plate at the cell densities listed in Table 2 (cells/cm$^2$). The cell density, and whether the cell type was plated in duplicate or triplicate, was determined and governed by the number of cells expressing the phenotype of interest.

TABLE 2

| Conditions Cell Source | Cell plating densities 96 Well Plate Culture Density of Plated Cells | | |
|---|---|---|---|
| | Sorted | All | All Max. Density |
| | Perfusate | | |
| Set #1: | 40.6 K/cm$^2$ | 40.6 K/cm$^2$ | 93.8 K/cm$^2$ |
| Set #2 | 40.6 K/cm$^2$ | 40.6 K/cm$^2$ | 93.8 K/cm$^2$ |
| Set #3: | 40.6 K/cm$^2$ | 40.6 K/cm$^2$ | 93.8 K/cm$^2$ |
| | Amnion | | |
| Set #1: | 6.3 K/cm$^2$ | 6.3 K/cm$^2$ | 62.5 K/cm$^2$ |
| Set #2 | 6.3 K/cm$^2$ | 6.3 K/cm$^2$ | 62.5 K/cm$^2$ |
| | Chorion | | |
| Set #1: | 6.3 K/cm$^2$ | 6.3 K/cm$^2$ | 62.5 K/cm$^2$ |
| Set #2 | 6.3 K/cm$^2$ | 6.3 K/cm$^2$ | 62.5 K/cm$^2$ |

Complete medium (60% DMEM-LG (Gibco) and 40% MCDB-201 (Sigma); 2% fetal calf serum (Hyclone Labs.); 1× insulin-transferrin-selenium (ITS); 1× linoleic acid-bovine serum albumin (LA-BSA); 10$^{-9}$ M dexamethasone (Sigma); 10$^{-4}$ M ascorbic acid 2-phosphate (Sigma); epidermal growth factor 10 ng/mL (R&D Systems); and platelet-derived growth factor (PDGF-BB) 10 ng/mL (R&D Systems)) was added to each well of the 96 well plate and the plate was placed in a 5% CO$_2$/37° C. incubator. On day 7, 100 μL of complete medium was added to each of the wells. The 96 well plate was monitored for about two weeks and a final assessment of the culture was completed on day 12. This is very early in the placental stem cell culture, and represents passage 0 cells.

6.3.1.5 Data Analysis

FACSCalibur data was analyzed in FlowJo (Tree star, Inc) using standard gating techniques. The BD FACS Aria data was analyzed using the FACSDiva software (Becton-Dickinson). The FACS Aria data was analyzed using doublet discrimination gating to minimize doublets, as well as, standard gating techniques. All results were compiled in Microsoft Excel and all values, herein, are represented as average±standard deviation (number, standard error of mean).

6.3.2 Results

6.3.2.1 Cellular Viability

Post-digestion viability was assessed using the manual trypan blue exclusion method (FIG. 1). The average viability of cells obtained from the majority of the digested tissue (from amnion, chorion or amnion-chorion plate) was around 70%. Amnion had an average viability of 74.35%±10.31% (n=6, SEM=4.21), chorion had an average viability of 78.18%±12.65% (n=4, SEM=6.32), amnion-chorion plate had an average viability of 69.05%±10.80% (n=4, SEM=5.40), and umbilical cord had an average viability of 63.30%±20.13% (n=4, SEM=10.06). Cells from perfusion, which did not undergo digestion, retained the highest average viability, 89.98±6.39% (n=5, SEM=2.86).

6.3.2.2 Cell Quantification

The populations of placental cells and umbilical cord cells were analyzed to determine the numbers of HLA ABC$^-$/CD45$^-$/CD34$^-$/CD133$^+$ cells. From the analysis of the BD FACSCalibur data, it was observed that the amnion, perfusate, and chorion contained the greatest total number of these cells, 30.72±21.80 cells (n=4, SEM=10.90), 26.92±22.56 cells (n=3, SEM=13.02), and 18.39±6.44 cells (n=2, SEM=4.55) respectively (data not shown). The amnion-chorion plate and umbilical cord contained the least total number of cells expressing the phenotype of interest, 4.72±4.16 cells (n=3, SEM=2.40) and 3.94±2.58 cells (n=3, SEM=1.49) respectively (data not shown).

Similarly, when the percent of total cells expressing the phenotype of interest was analyzed, it was observed that amnion and placental perfusate contained the highest percentages of cells expressing this phenotype (0.0319%±0.0202% (n=4, SEM=0.0101) and 0.0269%±0.0226% (n=3, SEM=0.0130) respectively (FIG. 2). Although umbilical cord contained a small number of cells expressing the phenotype of interest (FIG. 2), it contained the third highest percentage of cells expressing the phenotype of interest, 0.020±0.0226% (n=3, SEM=0.0131) (FIG. 2). The chorion and amnion-chorion plate contained the lowest percentages of cells expressing the phenotype of interest, 0.0184±0.0064% (n=2, SEM=0.0046) and 0.0177±0.0173% (n=3, SEM=0.010) respectively (FIG. 2).

Consistent with the results of the BD FACSCalibur analysis, the BD FACS Aria data also identified amnion, perfusate, and chorion as providing higher numbers of HLA ABC$^-$/CD45$^-$/CD34$^-$/CD133$^+$ cells than the remaining sources. The average total number of cells expressing the phenotype of interest among amnion, perfusate, and chorion was 126.47±55.61 cells (n=15, SEM=14.36), 81.65±34.64 cells (n=20, SEM=7.75), and 51.47±32.41 cells (n=15, SEM=8.37), respectively (data not shown). The amnion-chorion plate and umbilical cord contained the least total number of cells expressing the phenotype of interest, 44.89±37.43 cells (n=9, SEM=12.48) and 11.00±4.03 cells (n=9, SEM=1.34) respectively (data not shown).

BD FACS Aria data revealed that the perfusate and amnion produced the highest percentages of HLA ABC$^-$/CD45$^-$/CD34$^-$/CD133$^+$ cells, 0.1523±0.0227% (n=15, SEM=0.0059) and 0.0929±0.0419% (n=20, SEM=0.0094) respectively (FIG. 3). The amnion-chorion plate contained the third highest percentage of cells expressing the phenotype of interest, 0.0632±0.0333% (n=9, SEM=0.0111) (FIG. 3). The chorion and umbilical cord contained the lowest percentages of cells expressing the phenotype of interest, 0.0623±0.0249% (n=15, SEM=0.0064) and 0.0457±0.0055% (n=9, SEM=0.0018) respectively (FIG. 3).

After HLA ABC$^-$/CD45$^-$/CD34$^-$/CD133$^+$ cells were identified and quantified from each cell source, its cells were further analyzed and characterized for their expression of cell surface markers HLA-G, CD10, CD13, CD33, CD38, CD44, CD90, CD105, CD117, CD200, and CD105.

6.3.2.3 Placental Perfusate-Derived Cells

Perfusate-derived cells appeared generally positive for HLA-G, CD33, CD117, CD10, CD44, CD200, CD90, CD38, CD105, and CD13 (FIG. 4). The average expression of each marker for perfusate-derived cells was the following: 37.15%±38.55% (n=4, SEM=19.28) of the cells expressed HLA-G; 36.37%±21.98% (n=7, SEM=8.31) of the cells expressed CD33; 39.39%±39.91% (n=4, SEM=19.96) of the cells expressed CD117; 54.97%±33.08% (n=4, SEM=16.54) of the cells expressed CD10; 36.79%±11.42% (n=4, SEM=5.71) of the cells expressed CD44; 41.83%±19.42% (n=3, SEM=11.21) of the cells expressed CD200; 74.25%±26.74% (n=3, SEM=15.44) of the cells expressed CD90; 35.10%±23.10% (n=3, SEM=13.34) of the cells expressed CD38; 22.87%±6.87% (n=3, SEM=3.97) of the cells expressed CD105; and 25.49%±9.84% (n=3, SEM=5.68) of the cells expressed CD13.

6.3.2.4 Amnion-Derived Cells

Amnion-derived cells were consistently positive for HLA-G, CD33, CD117, CD10, CD44, CD200, CD90, CD38, CD105, and CD13 (FIG. 5). The average expression of each marker for amnion-derived was the following: 57.27%±41.11% (n=3, SEM=23.73) of the cells expressed HLA-G; 16.23%±15.81% (n=6, SEM=6.46) of the cells expressed CD33; 62.32%±37.89% (n=3, SEM=21.87) of the cells expressed CD117; 9.71%±13.73% (n=3, SEM=7.92) of the cells expressed CD10; 27.03%±22.65% (n=3, SEM=13.08) of the cells expressed CD44; 6.42%±0.88% (n=2, SEM=0.62) of the cells expressed CD200; 57.61% 122.10% (n=2, SEM=15.63) of the cells expressed CD90; 63.76%±4.40% (n=2, SEM=3.11) of the cells expressed CD38; 20.27%±5.88% (n=2, SEM=4.16) of the cells expressed CD105; and 54.37%±13.29% (n=2, SEM=9.40) of the cells expressed CD13.

6.3.2.5 Chorion-Derived Cells

Chorion-derived cells were consistently positive for HLA-G, CD117, CD10, CD44, CD200, CD90, CD38, and CD13, while the expression of CD33, and CD105 varied (FIG. 6). The average expression of each marker for chorion cells was the following: 53.25%±32.87% (n=3, SEM=18.98) of the cells expressed HLA-G; 15.44%±11.17% (n=6, SEM=4.56) of the cells expressed CD33; 70.76%±11.87% (n=3, SEM=6.86) of the cells expressed CD117; 35.84%±25.96% (n=3, SEM=14.99) of the cells expressed CD10; 28.76%±6.09% (n=3, SEM=3.52) of the cells expressed CD44; 29.20%±9.47% (n=2, SEM=6.70) of the cells expressed CD200; 54.88%±0.17% (n=2, SEM=0.12) of the cells expressed CD90;

68.63%±44.37% (n=2, SEM=31.37) of the cells expressed CD38; 23.81%±33.67% (n=2, SEM=23.81) of the cells expressed CD105; and 53.16%±62.70% (n=2, SEM=44.34) of the cells expressed CD13.

6.3.2.6 Amnion-Chorion Plate-Derived Cells

Cells from amnion-chorion plate were consistently positive for HLA-G, CD33, CD117, CD10, CD44, CD200, CD90, CD38, CD105, and CD13 (FIG. 7). The average expression of each marker for amnion-chorion plate-derived cells was the following: 78.52%±13.13% (n=2, SEM=9.29) of the cells expressed HLA-G; 38.33%±15.74% (n=5, SEM=7.04) of the cells expressed CD33; 69.56%±26.41% (n=2, SEM=18.67) of the cells expressed CD117; 42.44%±53.12% (n=2, SEM=37.56) of the cells expressed CD10; 32.47%±31.78% (n=2, SEM=22.47) of the cells expressed CD44; 5.56% (n=1) of the cells expressed CD200; 83.33% (n=1) of the cells expressed CD90; 83.52% (n=1) of the cells expressed CD38; 7.25% (n=1) of the cells expressed CD105; and 81.16% (n=1) of the cells expressed CD13.

6.3.2.7 Umbilical Cord-Derived Cells

Umbilical cord-derived cells were consistently positive for HLA-G, CD33, CD90, CD38, CD105, and CD13, while the expression of CD117, CD10, CD44, and CD200 varied (FIG. 8). The average expression of each marker for umbilical cord-derived cells was the following: 62.50%±53.03% (n=2, SEM=37.50) of the cells expressed HLA-G; 25.67%±11.28% (n=5, SEM=5.04) of the cells expressed CD33; 44.45%±62.85% (n=2, SEM=44.45) of the cells expressed CD117; 8.33%±11.79% (n=2, SEM=8.33) of the cells expressed CD10; 21.43%±30.30% (n=2, SEM=21.43) of the cells expressed CD44; 0.0% (n=1) of the cells expressed CD200; 81.25% (n=1) of the cells expressed CD90; 64.29% (n=1) of the cells expressed CD38; 6.25% (n=1) of the cells expressed CD105; and 50.0% (n=1) of the cells expressed CD13.

A summary of all marker expression averages is shown in FIG. 9.

6.3.2.8 BD FACS Aria Sort Report

The three distinct populations of placental cells that expressed the greatest percentages of HLA ABC, CD45, CD34, and CD133 (cells derived from perfusate, amnion and chorion) were stained with 7AAD and the antibodies for these markers. The three populations were positively sorted for live cells expressing the phenotype of interest. The results of the BD FACS Aria sort are listed in Table 3.

TABLE 3

BD FACS Aria Sort Report

| Cell Source | Events Processed | Events Sorted (Phenotype of Interest) | % Of Total |
|---|---|---|---|
| Perfusate | 135540110 | 51215 | 0.037786 |
| Amnion | 7385933 | 4019 | 0.054414 |
| Chorion | 108498122 | 4016 | 0.003701 |

The three distinct populations of positively sorted cells ("sorted") and their corresponding non-sorted cells were plated and the results of the culture were assessed on day 12 (Table 3). Sorted perfusate-derived cells, plated at a cell density of 40,600/cm², resulted in small, round, non-adherent cells. Two out of the three sets of non-sorted perfusate-derived cells, each plated at a cell density of 40,600/cm², resulted in mostly small, round, non-adherent cells with several adherent cells located around the periphery of well. Non-sorted perfusate-derived cells, plated at a cell density of 93,800/cm², resulted in mostly small, round, non-adherent cells with several adherent cells located around the well peripheries.

Sorted amnion-derived cells, plated at a cell density of 6,300/cm², resulted in small, round, non-adherent cells. Non-sorted amnion-derived cells, plated at a cell density of 6,300/cm², resulted in small, round, non-adherent cells. Non-sorted amnion-derived cells plated at a cell density of 62,500/cm resulted in small, round, non-adherent cells.

Sorted chorion-derived cells, plated at a cell density of 6,300/cm², resulted in small, round, non-adherent cells. Non-sorted chorion-derived cells, plated at a cell density of 6,300/cm², resulted in small, round, non-adherent cells. Non-sorted chorion-derived cells plated at a cell density of 62,500/cm², resulted in small, round, non-adherent cells.

A majority of the above non-adherent cells, when cultured, adhered to the tissue culture surface and assumed a fibroblastoid shape.

Subsequent to the performance of the experiments related above, and further culture of the placental stem cells, it was determined that the labeling of the antibodies for CD117 and CD133, in which a streptavidin-conjugated antibody was labeled with biotin-conjugated phycoerythrin (PE), produced background significant enough to resemble a positive reading. This background had initially resulted in the placental stem cells being deemed to be positive for both markers. When a different label, APC or PerCP was used, the background was reduced, and the placental stem cells were correctly determined to be negative for both CD117 and CD133.

6.4 Example 4: Characterization of Placental Stem Cell Marker Expression

This example describes experiments designed to further characterize expression of a variety of protein expression markers by placental stem cells as follows: $CD200^+$, $CD105^+$, $CD90^+$, $CD10^+$, cytokeratin $18^+$, $CD34^-$, and $CD45^-$. In addition, the baseline expression of hepatocyte markers on uninduced placental stem cells is assessed, including, for example, expression of cytokeratin 18, secretion of hepatocyte growth factor (HGF) and expression of asialoglycoprotein receptor.

Placental stem cell marker expression is assessed according to the following exemplary flow cytometry protocol. Placental stem cells are first trypsinized, then incubated with fluorochrome-conjugated antibodies on ice for 30 minutes in the dark, rinsed twice with cold PBS-2% BSA and then analyzed with a FACSCalibur (BD Biosciences). Exemplary antibodies suitable for these assays are PerCP-conjugated anti-CD34, FITC conjugated anti-CD105, APC-conjugated anti-CD10, and PE conjugated CD200. Other suitable antibody reagents include, the appropriate fluorophore combinations: APC-conjugated anti-HLA-ABC, PE-conjugated anti-CD31, PerCP-conjugated anti-CD45, FITC-conjugated anti-CD38, PE-conjugated anti-CD44, FITC-conjugated anti-cytokeratin K (or cytokeratin 18), APC-conjugated anti-CD90, APC-conjugated anti-CD86, FITC-conjugated anti-CD80, FITC-conjugated anti-HLA DR, DQ, DP, PE-conjugated anti-β-2-microglobulin, APC-conjugated anti-CD133 and PerCP-conjugated anti-CD117. Except where otherwise noted, these antibodies are available from BD-Pharmingen. Analysis and statistics of flow cytometry data is accomplished with Flowjo (Tree Star, Inc. Ashland, Oreg.).

Cytokines produced by placental stem cells are analyzed by collecting supernatants of cultured cells using a LincoPlex Adipogenic analysis kit and a Luminex instrument according to the manufacturer's instructions.

6.5 Example 5: Induction of Placental Cell Differentiation Into Hepatocytes Using Sodium Butyrate This example describes exemplary methods for induction of hepatocyte differentiation of placental stem cells using sodium butyrate. The methods are designed to characterize Na-butyrate induced placental stem cells using a variety of protein expression markers, expression of hepatocyte specific genes and hepatocyte specific markers such as cytokeratin 18 (a molecule already expressed in undifferentiated placental stem cells) and asialoglycoprotein receptor. The ability of induced placental stem cells to produce intracellular albumin and secretion of urea is assessed.

To induce differentiation, placental stem cells are plated at a density of about $10^5$ cells/well in 0.1% gelatin coated six well plates in Iscove's Modified Dulbecco's medium (IMDM) (Gibco, Cat #31980-030) containing 20% fetal bovine serum (Gibco), 4 mM L-glutamine (Gibco), 100 U/ml penicillin, 100 U/ml streptomycin (Gibco) and 10 µg/ml gentamicin (Gibco). Gelatin solution (0.1%) is prepared by dissolving 0.5 gm of porcine gelatin (Sigma-Aldrich, Cat # G-2500) in 500 ml of Phosphate Buffered Saline (PBS) (Gibco, Cat #20012-027) with gentle heating. To coat plates with gelatin, 2 ml of 0.1% gelatin solution is added to each well of a polystyrene tissue culture treated plate. The plates are incubated for 2 hrs following which the gelatin solution is aspirated. The plates are washed once with PBS and then 2.5 ml of IMDM is added followed by about $10^5$ cells/well. Optionally, cells are exposed to 1% DMSO (Sigma-Aldrich) for the next 4 days followed by exposure to Na-butyrate (Sigma Aldrich, Cat # B5887) at different concentrations (1, 2.5, 5, 10 mM) for 6 days. Media is replaced daily.

In order to measure function of the differentiated cell, a secondary culture is initiated where cells are removed from the primary culture dish and replated on collagen type I coated (BD Biosciences) and polystyrene 12 well plates at a density of about $10^5$ cells/well. Media is changed 24 hrs after replating and cells are tested for functional assays 48 hrs after replating.

6.6 Example 6: Aggregation of Placental Stem Cells by Alginate-Poly-L-Lysine Microencapsulation in Preparation for Differentiation into Hepatocytes This example describes exemplary methods for aggregating placental stem cells using alginate microencapsulation technology in preparation for differentiating the cells into hepatocytes.

Alginate Poly-L-Lysine Encapsulation

An alginate solution is generated by dissolving 2.2 g of alginate (Sigma-Aldrich, MW: 100,000-200,000 g/mol, G-Content: 65%-70%) in 100 mL of $Ca^{2+}$ free DMEM (Gibco), using a heated magnetic stir plate at a temperature of 45° C. The solution is then filtered using a 25-micron syringe filter (Fisher Brand, Pittsburg, Pa.). A confluent monolayer of adherent cells is removed following trypsin incubation, centrifuged for 10 minutes at 1200 rpm, and resuspended in PBS. The cells are washed twice more with PBS (Gibco), resuspended in 2 mL of their respective media and both cell number and viability assessed using the method of trypan blue (Gibco) exclusion. To create the cell-alginate mixture a 1 mL aliquot of cell suspension with a seeding density of about $5 \times 10^7$ cells/ml is added to 9 mL of a 2.2% (w/v) alginate solution to yield a final cell seeding density of about $5 \times 10^6$ cells/ml and a final alginate concentration of 2.0% (w/v). This solution is transferred to a 10 ml syringe (BD Biosciences), which, in turn, is connected to a syringe pump (KD Scientific, Holliston, Mass.). Alginate beads are generated using an electrostatic bead generator (Nisco, Zürich, Switzerland) at a flow rate of 40 ml/hour, and an applied voltage of 6.5 kV, resulting in beads with a diameter of 500 µm. The beads are extruded into a 200 mL bath of $CaCl_2$ (100 mM) (Sigma-Aldrich), containing 145 mM NaCl (Sigma-Aldrich), and 10 mM MOPS (Sigma-Aldrich) and are left to polymerize for 10 minutes at room temperature. Beads are transferred to a tissue culture treated T-25 flask (Falcon, BD Biosciences), following the polymerization step. The $CaCl_2$ solution is removed using a 5 mL pipette, and the beads are washed with 5 mL HEPES (Gibco). The buffer is removed and the beads are resuspended in 5 ml of poly-L-lysine (PLL) (Sigma-Aldrich, MW: 68,600 g/mol) (0.05% w/v) for 2 minutes. The PLL is then gently removed, replaced with HEPES to wash the beads and the beads are ultimately resuspended into 5 ml of cell culture media. Media is changed at, e.g., 4, 8, 11, 14 and 17 days post-encapsulation.

Assessment of Intracapsular Viability

Viability within beads is assessed with a calcein (Molecular Probes, Eugene, Oreg.), ethidium homodimer (Molecular Probes) stain immediately following encapsulation. Calcein is only cleaved to form fluorescent products in live cells while ethidium homodimer is only incorporated into the nucleus of dead cells. Calcein and ethidium homodimer images are acquired using a Zeiss Axiovert LSM laser scanning confocal microscope (Germany) fitted with a 495 nm excitation filter and emission filters of 515 nm and 635 nm, respectively. Specifically, z-sections of 500 um diameter beads are taken at 10 um intervals, for a total depth of 250 um. Three experiments incorporated an analysis of 15 beads per experiment. Digitized images are quantified using Olympus MICROSUITE™. Viability is assessed for each cross-section of every bead.

Cell Recovery and Assessment Following Depolymerization

Functional analysis and aggregate size calculations are performed on each of the analysis days following the release of cells from the beads. A minimum of 1500 beads is analyzed per replicate per condition. Beads are washed with PBS, and 100 mM sodium citrate (Fisher Scientific), containing 10 mM MOPS (Sigma-Aldrich) and 27 mM NaCl (Sigma-Aldrich) are added for 30 minutes at 37° C. to induce depolymerization. To determine recovery yield following depolymerization, a known concentration of cells is encapsulated and immediately depolymerized. Following centrifugation, both the cell pellet as well as the supernatant (which contains bead particles but no intact beads) are counted using trypan blue exclusion (which does not stain the capsule), and after a mass balance, verify that approximately the same number of cells are present as in the starting population. This method demonstrates a 98% recovery of the encapsulated cell population. The released cells are centrifuged at 1200 rpm for 10 minutes, the sodium citrate solution aspirated, the cell pellet washed with PBS (3x), and resuspended in cell specific media. The cells are then counted using the trypan blue method described above.

Intracapsular Aggregate Size Determination

Beads are sampled from tissue culture treated T-25 flasks and transferred to 35 mm Mattek dishes (Mattek, Ashland, Mass.) immediately following encapsulation (day 0), and on the analysis days 8, 11, 14, 17 20. Bright field images are acquired using a Zeiss Axiovert LSM laser scanning confocal microscope (Germany). Specifically, z-sections of 500 um diameter beads are taken at 50 um intervals, to avoid multiple quantification of the same aggregate, for a total depth of 250 um. Images are quantified using Olympus Microsuite. In short, a color threshold is first applied in order to distinguish cellular aggregates from the image background. The diameter of the aggregate is then determined using the mean diameter particle measurement.

6.7 Example 7: In Situ Indirect Immunofluorescent Cytokeratin-18 and Intracellular Albumin Analysis This example describes exemplary methods for assessing cytokeratin-18 and albumin expression by hepatocytes obtained from differentiated placental stem cells. Differentiated cells (recovered following depolymerization if appropriate) are transferred to a tissue culture treated 24 well plate (Falcon, BD Biosciences). Specifically, the isolated cell population is diluted to about $6 \times 10^4$ cells in 0.75 ml of media and incubated for one hour at 37° C. to allow for cell attachment. The cells are then washed for 10 min in cold PBS and fixed in 4% paraformaldehyde (Sigma-Aldrich) in PBS for 15 minutes at room temperature. The cells are washed twice for 10 min in cold PBS and then twice for 10 min in cold saponine/PBS (SAP) membrane permeabilization buffer containing 1% bovine serum albumin (BSA) (Sigma-Aldrich), 0.5% saponine (Sigma-Aldrich) and 0.1% sodium azide (Sigma-Aldrich). To detect intracellular albumin, the cells are subsequently incubated for 30 minutes at 4° C. in a SAP solution containing rabbit anti-mouse albumin antibody (150 µg/ml) (MP Biomedicals, Irvine, Calif.), or normal rabbit serum (150 µg/ml) (MP Biomedicals) as an isotype control, washed twice for 10 min in cold SAP buffer, and then treated for 30 minutes at 4° C. with the secondary antibody, FITC-conjugated donkey anti-rabbit, diluted 1:500 (Jackson Immuno Labs, Westgrove, Pa.). To detect cytokeratin 18, cells are incubated for 30 minutes at 4° C. in a SAP solution containing rabbit anti-mouse cytokeratin 18 antibody (IgG1) (1:50 dilution) (Santa Cruz Biotechnology) or the IgG1 fraction of normal rabbit serum (1:100 dilution) (Santa Cruz Biotechnology) as an isotype control, and then treated for 30 minutes at 4° C. with the secondary antibody, FITC-conjugated goat anti-rabbit, diluted 1:200 (Jackson Immuno Labs Westgrove, Pa.). For both stains, cells are then washed once with cold SAP buffer and once with cold PBS. Fluorescent images are acquired using a computer-interfaced inverted Olympus IX70 microscope. Specimens are excited using a 515 nm filter. Fluorescent intensity values are determined for each cell using Olympus MICROSUITE™. Experimental intensity values for each cell are calculated after subtracting the average intensity of the isotype control.

6.8 Example 8: Glycogen Staining

This example describes exemplary methods for assessing glycogen production by hepatocytes obtained from differentiated placental stem cells. Following depolymerization, cells are transferred to tissue culture treated 24 well plates (Falcon, BD Biosciences) and fixed with 10% formalin-ethanol fixative solution for 15 minutes at room temperature, with subsequent washes with PBS. Fixed cells are exposed to 0.25 ml of Periodic Acid Solution (Sigma Aldrich) per well for 5 minutes at room temperature. Glycols are oxidized to aldehydes in this process. After washing cells with PBS to remove the PAS, 1 ml of Schiff's reagent is added per well and cells exposed for 15 minutes at room temperature. Schiff's reagent, a mixture of pararosaniline and sodium metabisulfite, reacts to release a pararosaniline product that stains the glycol-containing cellular elements. A third PBS wash to remove the reagent is followed by image acquisition with an Olympus IX70 microscope and Olympus digital camera.

6.9 Example 9: Glucose and Lactate Measurements

This example describes exemplary methods for assessing glucose and lactate consumption and/or production by hepatocytes obtained from differentiated placental stem cells. Supernatants (1 ml) were collected in triplicate for each cell type in secondary culture and then tested using a Bioprofile Bioanalyzer 400 (Nova Biomedical, Waltham, Mass.) for metabolite measurements of glucose and lactate. On each day of analysis, base media glucose and lactate measurements were measured and the mean values were subtracted from the test values to obtain uptake or production. Cells were counted for each condition to get the final consumption or production rate.

6.10 Example 10: Urea Analysis

This example describes exemplary methods for assessing urea production by hepatocytes obtained from differentiated placental stem cells. Media samples are collected directly from cell cultures and stored at −20° C. for subsequent urea content analysis. Urea synthesis is assayed using a commercially available kit (StanBio, Boerne, Tex.). A standard curve is generated by creating serial dilutions of a urea standard from 300 µg/ml to 0 µg/ml. Absorbance readings are obtained using a Biorad (Hercules, Calif.) Model 680 plate reader with a 585 nm emission filter. Urea values are normalized to the cell number recorded on the day of media sample collection.

6.11 Example 11: Sandwich ELISA for Detection of Albumin Secretion

This example describes exemplary methods for assessing albumin secretion by hepatocytes obtained from differentiated placental stem cells. In order to detect secreted albumin within the media supernatants obtained on each of the analysis days, a commercially available mouse albumin ELISA kit (Bethyl Laboratories, #E90-134) is used. A standard curve is generated by creating serial dilutions of an albumin standard from 7.8 to 10,000 ng/mL. Absorbance readings are obtained using a Biorad (Hercules, Calif.) Model 680 plate reader with a 450 nm emission filter. Albumin values are normalized to the cell number recorded on the day of media sample collection.

6.12 Example 12: Mouse Model of Hepatitis B Infection

This Example describes a mouse model of hepatitis B virus (HBV) infection that uses hepatocytes differentiated from the placental stem cells described elsewhere herein. The mouse is produced by (1) irradiating a mouse, which is then protected by administration of SCID mouse bone marrow; and (2) administration of HBV-infected hepatocytes that have been differentiated from placental stem cells. The mouse is then administered a compound that is to be tested for its ability to reduce viral replication or viral load.

Placental Stem Cells.

Adherent placental stem cells are obtained by one or more of the methods described in Example 1, above.

Preparation of Hepatocytes.

Placental Stem Cells are Differentiated According to the method described in Examples 4, above.

HBV Infection of Placental Stem Cell-Derived Hepatocytes.

Placental stem cell-derived hepatocytes in alginate are collected by centrifugation and resuspended in 1 mL of high-titer HBV DNA human serum supplemented with 3 μg hexidementhrine bromide (Sigma-Aldrich, H-9268, St. Louis, Mo.) and 0.5 μg human interleukin 6 (IL-6; Preprotech, London, England).

Preparation of Mice.

CB 16F or BNX (beige/nude/xid) mice, and NOD/SCID mice at age 6-10 weeks, are used. Mice are fed sterile food and acid water containing ciprofloxacin (20 μg/mL). CB 16F mice (Harlan Laboratories, Weitzmann Institute Animal Breeding Center, Rehovot, Israel) are exposed to total body irradiation at a dose of about 4 Gy followed three days later by a does of about 11 Gy from a gamma beam 150-A $^{60}$Co source (Atomic Energy of Canada, Kanata, Ontario, Canada) at an irradiation rate of about 0.7 Gy/min. From about $4 \times 10^6$ to about $6 \times 10^6$ bone marrow cells from NOD/SCID mice, in 0.2 mL phosphate-buffered saline, are immediately transplanted into the irradiated mice. Bone marrow cells are prepared by disruption of femoral and tibial bones in an Omni-Mixer in phosphate buffered saline to obtain marrow cells, followed by depletion of T cells from the resulting cell suspension. See Levite et al., *Transplantation* 8:1-3 (1991). The mice are injected daily with 1 mg Fortum (Glaxo) intraperitoneally for 5 days following bone marrow transplantation. Directly after bone marrow cell transplantation, HBV-infected placental stem cell-derived hepatocytes (about $5 \times 10^7$) are then transplanted into the irradiated mice under the kidney capsule or into the ear pinna. Engraftment of hepatocytes can be assessed by biopsy and hematoxylin-eosin staining, and by detection of expression of human serum albumin-encoding mRNA in the transplanted tissue.

BNX mice are prepared as CB16F mice, except that BNX mice are irradiated once at a dose of 11 Gy, and transplantation of the HBV-infected hepatocytes takes place at least 10 days after bone marrow cell transplantation.

Extraction of DNA from HBV-Infected Sera.

DNA is extracted from 100 μL of serum by proteinase K digestion in 400 μL reaction mixture containing 0.25% sodium dodecyl sulfate, 5 mmol/L EDTA, 10 mmol/L Tris HCl (pH 8.0), and 250 μg/mL proteinase K (Sigma, St. Louis, Mo.). After 2.5 hours at 65° C., 1 μg of a DNA carrier and 0.5 mg BSA is added. DNA is then extracted by phenol-chloroform and precipitated in ethanol overnight at −20° C. Following centrifugation for 15 minutes at 20,000 g, the DNA pellets is washed with 70% ethanol, dried, and resuspended in 50 μL of water.

Determination of HBV DNA Level in Mouse Sera.

The HBV DNA copy number is determined by semiquantitative PCR using HBV-specific primers. PCR products are separated on a standard 2% agarose gel. 50 μL of the products are dot blotted and hybridized overnight at 42° C. with an appropriate [$^{32}$P]-labeled DNA fragment (Rediprime DNA labeling system, Amersham, Buckinghamshire, UK). The blot is then washed in 0.1×0.15 mol/L NaCl and 0.015 mol/L sodium citrate, pH 7.0 and 1% SDS at 55° C., and exposed to X ray film. The intensity of dots is read on an ELISA reader, e.g., Dynatech at 630 nm, or on a Molecular Dynamics computing densitometer Model 300A. Viral load is determined using a standard curve composed of DNA samples obtained from calibrated human serum diluted in normal mouse serum comprising copy numbers from 102 to $10^7$ per 100 μL samples. A mouse having a viral load of less than about $5 \times 10^3$/mL serum is considered to be uninfected. Primers used in this procedure recognize both covalently closed circular and relaxed forms of HBV.

HBV viral load can, alternately or additionally, be determined by ELISA using one or more antibodies that recognize a surface antigen of HBV.

Determination of HBV Covalently Closed Circular DNA in Engrafted Hepatocytes.

This step can be performed if confirmation of viral replication is needed. DNA is extracted from hepatocytes collected by centrifugation (about $1 \times 10^5$) and resuspended in 100 μL of H$_2$O. Fifty μL is subjected to PCR using HBV-specific primers in 100 μL reaction mixture containing 13 Taq Pol buffer, 2.5 mmol/L MgCl$_2$, 0.2 mmol/L of each dNTP, 50 μmol of each primer, 1 mg/mL BSA, and 2.5 U of Taq Pol. (Promega). The PCR reaction is programmed for 2 minutes at 94° C., and then 30 cycles, 1 minute at 94° C., and 3 minutes at 72° C., with a final elongation reaction of 5 minutes at 72° C. PCR products are analyzed on a 2% agarose gel and by dot-blot hybridization using a DNA fragment corresponding to a portion of the core sequence. This procedure uses primers that recognize only the covalently closed circular form of HBV.

Determination of Antiviral Activity of Compounds.

Once viremia is established, the mice are administered a compound that is to be tested for anti-HBV activity. The route of administration is determined on a compound-by-compound basis, but is generally either intraperitoneal or intravenous. Administration of the compound is performed at 6-17 days post-transplantation with infected hepatocytes. On days 2 and 9 post-administration, serum is drawn from the mice and assessed for viral load using antibody to HBsAg (HBV surface antigen) and PCR to detect HBV covalently closed circular DNA (cccHBV). The compound is determined to be an antiviral compound if the viral load is detectably reduced (e.g., statistically significantly reduced) compared to the viral load in mice not administered the compound. Viral load can be compared to the amount of cccHBV present to determine whether a compound that reduces viral load is an inhibitor of HBV replication.

6.13 Example 13: Induction of Differentiation of Placental Stem Cells into Chondrocytes 6.13.1 General Method Chondrogenic differentiation of placental stem cells is generally accomplished as follows:

1. Placental stem cells are maintained in MSCGM (Cambrex) or DMEM supplemented with 15% cord blood serum.

2. Placental stem cells are aliquoted into a sterile polypropylene tube. The cells are centrifuged (150×g for 5 minutes), and washed twice in Incomplete Chondrogenesis Medium (Cambrex).

3. After the last wash, the cells are resuspended in Complete Chondrogenesis Medium (Cambrex) containing 0.01 μg/ml TGF-beta-3 at a concentration of 5×10(5) cells/ml.

4. 0.5 ml of cells is aliquoted into a 15 ml polypropylene culture tube. The cells are pelleted at 150×g for 5 minutes. The pellet is left intact in the medium.

5. Loosely capped tubes are incubated at 37° C., 5% CO2 for 24 hours.

6. The cell pellets are fed every 2-3 days with freshly prepared complete chondrogenesis medium.

7. Pellets are maintained suspended in medium by daily agitation using a low speed vortex.

8. Chondrogenic cell pellets are harvested after 14-28 days in culture.

9. Chondrogenesis is characterized by e.g., observation of production of esoinophilic ground substance, assessing cell morphology, an/or RT/PCR confirmation of collagen 2 and/or collagen 9 gene expression and/or the production of cartilage matrix acid mucopolysaccharides, as confirmed by Alcian blue cytochemical staining.

Chondrogenesis can also be assessed by gene expression for early stage chondrogenesis markers fibromodulin and cartilage oligomeric matrix protein; gene expression for mid-stage chondrogenesis markers aggrecan, versican, decorin and biglycan; and gene expression for types II and X collagens and chondroadherein, markers of mature chondrocytes.

Placental stem cells can also be induced to chondrogenesis by the method above, wherein the placental stem cells are cultured on nanofibrous scaffolds such as poly(L-lactic acid) (PLLA), type I collagen, or a copolymer of vinylidene fluoride and trifluoroethylene (PVDF-TrFE), beginning at step 3, without centrifugation step 4.

6.13.2 Differentiation of Placental and Umbilical Cord Stem Cells Into Chondrogenic Cells This Example demonstrates the differentiation of placental stem cells into chondrogenic cells and the development of cartilage-like tissue from such cells.

Cartilage is an avascular, alymphatic tissue that lacks a nerve supply. Cartilage has a low chondrocyte density (<5%), however these cells are surprisingly efficient at maintaining the extracellular matrix around them. Three main types of cartilage exist in the body: (1) articular cartilage, which facilitates joint lubrication in joints; (2) fibrocartilage, which provides shock absorption in, e.g., meniscus and intervertebral disc; and (3) elastic cartilage, which provides anatomical structure in, e.g., nose and ears. All three types of cartilage are similar in biochemical structure.

Joint pain is a major cause of disability and provides an unmet need of relief in the area of orthopedics. Primary osteoarthritis (which can cause joint degeneration), and trauma are two common causes of pain. Approximately 9% of the U.S. population has osteoarthritis of hip or knee, and more than 2 million knee surgeries are performed yearly. Unfortunately, current treatments are more geared towards treatment of symptoms rather than repairing the cartilage. Natural repair occurs when fibroblast-like cells invade the area and fill it with fibrous tissue which is neither as resilient or elastic as the normal tissue, hence causing more damage. Treatment options historically included tissue grafts, subchondral drilling, or total joint replacement. More recent treatments however include CARTICEL®, an autologous chondrocyte injection; SYNVISC® and ORTHOVISC®, which are hyaluronic acid injections for temporary pain relief; and CHONDROGEN™, an injection of adult mesenchymal stem cells for meniscus repair. In general, the trend seems to be lying more towards cellular therapies and/or tissue engineered products involving chondrocytes or stem cells.

Materials and Methods.

Two placental stem cell lines from amnion/chorion, designated AC61665, P3 (passage 3) and AC63919, P5, and two from umbilical cord, designated UC67249, P2 and UC67477, P3 were used in the studies outlined below. Human mesenchymal stem cells (MSC) were used as positive controls, and an osteosarcoma cell line, MC3T3, and human dermal fibroblasts (HDF) were used as negative controls.

Placental and umbilical cord stem cells were isolated and purified from full term human placenta by enzymatic digestion. Human MSC cells and HDF cells were purchased from Cambrex, and MC3T3 cells were purchased from American Type Culture Collection. All cell lines used were centrifuged into pellets in polypropylene centrifuge tubes at 800 RPM for 5 minutes and grown in both chondrogenic induction media (Cambrex) and non-inducing basal MSC media (Cambrex). Pellets were harvested and histologically analyzed at 7, 14, 21 and 28 days by staining for glycosaminoglycans (GAGs) with Alcian Blue, and/or for collagens with Sirius Red. Collagen type was further assessed with immunostaining. RNA analysis for cartilage-specific genes was performed at 7 and 14 days.

Results

Experiment 1:

Chondrogenesis studies were designed to achieve three main objectives: (1) to demonstrate that placental and umbilical cord stem cells can differentiate and form cartilage tissue; (2) to demonstrate that placental and umbilical cord stem cells can differentiate functionally into chondrocytes; and (3) to validate results obtained with the stem cells by evaluating control cell lines.

For objective 1, in a preliminary study, one placental stem cell line was cultured in chondrogenic induction medium in the form of cell pellets, either with or without bone morphogenic protein (BMP) at a final concentration of 500 ng/mL. Pellets were assessed for evidence of chondrogenic induction every week for 4 weeks. Results indicated that the pellets do increase in size over time. However, no visual differences were noted between the BMP+ and BMP− samples. Pellets were also histologically analyzed for GAGs, an indicator of cartilage tissue, by staining with Alcian Blue. BMP+ cells generally appeared more metabolically active with pale vacuoles whereas BMP− cells were smaller with dense-stained nuclei and less cytoplasm (reflects low metabolic activity). At 7 days, BMP+ cells had stained heavily blue, while BMP− had stained only faintly. By 28 days of induction, both BMP+ and BMP− cells were roughly equivalently stained with Alcian Blue. Overall, cell density decreased over time, and matrix overtook the pellet. In contrast, the MC3T3 negative cell line did not demonstrate any presence of GAG when stained with Alcian Blue.

Experiment 2:

Based on the results of Experiment 1, a more detailed study was designed to assess the chondrogenic differentiation potential of two placental stem cell and two umbilical cord stem cell lines. In addition to the Alcian Blue histology, cells were also stained with Sirius Red, which is specific for type II collagen. Multiple pellets were made for each cell line, with and without induction media.

The pelleted, cultured cell lines were first assessed by gross observation for macroscopic generation of cartilage. Overall, the stem cell lines were observed to make pellets as early as day 1. These pellets grew over time and formed a tough matrix, appearing white, shining and cartilage-like, and became mechanically tough. By visual inspection, pellets from placental stem cells or umbilical cord stem cells were much larger than the MSC controls. Control pellets in non-induction media started to fall apart by Day 11, and were much smaller at 28 days than pellets developed by cells cultured in chondrogenic induction medium. Visually, there were no differences between pellets formed by placental stem cells or umbilical cord. However, the UC67249 stem cell line, which was initiated in dexamethasone-free media, formed larger pellets. Negative control MC3T3 cells did not form pellets; however, HDFs did form pellets.

Representative pellets from all test groups were then subjected to histological analysis for GAG's and collagen. Generally, pellets formed by the stem cells under inducing conditions were much larger and stayed intact better than pellets formed under non-inducing conditions. Pellets formed under inducing conditions showed production of GAGs and increasing collagen content over time, and as early as seven days, while pellets formed under non-inducing conditions showed little to no collagen production, as evidenced by weak Alcian Blue staining. In general, the placental stem cells and umbilical cord stem cells appeared, by visual inspection, to produce tougher, larger pellets, and appeared to be producing more collagen over time, than the mesenchymal stem cells. Moreover, over the course of the study, the collagen appeared to thicken, and the collagen type appeared to change, as evidenced by changes in the fiber colors under polarized light (colors correlate to fiber thickness which may be indicative of collagen type). Non-induced placental stem cells produced much less type II collagen, if any, compared to the induced stem cells. Over the 28-day period, cell density decreased as matrix production increased, a characteristic of cartilage tissue.

These studies confirm that placental and umbilical cord stem cells can be differentiated along a chondrogenic pathway, and can easily be induced to form cartilage tissue. Initial observations indicate that such stem cells are preferable to MSCs for the formation of cartilage tissue.

6.14 Example 14: Induction of Differentiation into Chondrocytes by Nanofibrous Scaffolds This example describes methods for inducing the differentiation of stem cells, including placental stem cells or mesenchymal stem cells from bone marrow (BM-MSC), into chondrocytes with nanofibrous scaffolds. The objectives of this example are threefold: 1) to characterize chondrogenic differentiation of placental stem cells in vitro; 2) determine the optimum scaffold for stimulating chondrogenic differentiation of placental stem cells in vitro; and 3) evaluate in vivo repair of osteochondral defects in a rabbit model using placental stem cells-scaffold constructs.

To accomplish Objective 1, dynamic pellet placental stem cells cultures are used to lengthen culture duration beyond 28 days. Temporal gene expression as well as biochemical and histological analyses of early and late stage markers of chondrogenesis for placental stem cells in static as well as dynamic pellet cultures are assessed. Placental stem cells are cultured with or without TGF-$\beta_3$ in pellet cultures under static or dynamic conditions for up to 56 days. By real-time PCR, quantitative gene expression is performed for early stage markers of fibromodulin and cartilage oligomeric matrix protein. Mid-stage markers of aggrecan, versican, decorin and biglycan are also assessed. Genes for types II and X collagens and chondroadherin, which are characteristic of mature chondrocytes, are also assessed. Biochemical assays are performed for type II collagen, glycosaminoglycan, and proteoglycan synthesis. Tissue morphology of the chondrogenic pellets are also characterized by histological staining during the time course.

To accomplish Objective 2, the ability of electrospun nanofibrous scaffolds to promote placental stem cell differentiation into chondrocytes is assessed. Scaffolds composed of poly(L-lactic acid) (PLLA), type I collagen and a copolymer of vinylidene fluoride and trifluoroethylene (PVDF-TrFE) are assessed. Placental stem cells are loaded onto scaffolds generated from these materials and cultured in both static and dynamic conditions. Quantitative gene expression, biochemical and histological analyses, and mechanical testing are performed during the study time course.

To accomplish Objective 3, chondral repair by placental stem cells is assessed by in vivo functional evaluation in an animal model that will not spontaneously heal a cartilage defect such as, for example, a rabbit osteochondral defect model. Scaffolds that support chondrogenic differentiation are evaluated in this model in combination with placental stem cells. Repair is evaluated by histochemical staining, specifically accessing the extent of cartilage union between uninjured cartilage and repaired cartilage. Osteo-chondral repair is also measured by mechanical evaluation of samples excised from the site of the original defect.

6.14.1 Fibrous Scaffold Fabrication

This example describes fabrication and characterization of exemplary nanofiber non-woven meshes. The technique of electrospinning was employed to produce nanoscale fiber meshes. The resulting meshes have high surface area, controllable porosity, architecture and mechanical properties. Fibers produced with this technique are on the same scale as the fibers of the ECM. poly(L-lactic acid) (PLLA) and poly lactic glycolic acid (PLGA) were used as the polymer compositions since they are one of the most widely used biomaterials in the tissue engineering field. The potential use of these scaffolds as tissue engineering scaffolds was then assessed by cell proliferation and differentiation of human MSCs.

The electrospinning process is affected by varying the electric potential, flow rate, solution concentration, capillary-collector distance, diameter of the needle, and ambient parameters, e.g., temperature. To fabricate PLLA and PLGA scaffolds of four distinct fiber diameters, namely 290 nm, 1 µm, 5 µm and 9 µm, the voltage [20 KV] and collector to needle distance [30 cm] were kept constant. The needle gauge size [12G; 22G], the flow rate [0.05-0.1 mL/min] and the solution concentration [10-25 w/w %] were varied.

The average diameter distribution of PLLA and PLGA electrospun mats generated thereby is listed in Table 4. Microfiber and the nanofiber scaffolds of both PLLA and PLGA had a porosity of 39% and 47%, respectively. The morphology of the electrospun fibers was observed by scanning electron microscopy. By inspection, the fibers were free of beads, appeared round and were aligned randomly in a non-woven fashion.

TABLE 4

| Polymer | Average Diameter | Polymer | Average Diameter |
|---------|------------------|---------|------------------|
| PLLA-1 | 290 ± 84 nm | PLGA-1 | 380 ± 0.80 nm |
| PLLA-2 | 1 ± 0.4 µm | PLGA-2 | 1 ± 0.3 µm |
| PLLA-3 | 5 ± 1.5 µm | PLGA-3 | 6 ± 1.5 µm |
| PLLA-4 | 9 ± 2.0 µm | PLGA-4 | 9 ± 1.6 µm |

6.14.2 Seeding of Human MSCs on Nanofibrous Scaffolds

Human BM-MSCs isolated from whole bone marrow and subcultured were seeded onto microfiber and nanofiber scaffolds. Cell culture plastic was used as a control surface. BM-MSCs grown on both nano and microfiber scaffolds had similar growth kinetics. Cell morphology and uniformity of the cell layer was observed by SEM. Cells seeded on nanofibers were uniformly distributed across the scaffold surface whereas cells on microfiber scaffolds were spread out along the fibrils and less uniformly distributed, regardless of composition. This finding was also confirmed using actin cytoskeleton staining and viewed by confocal microscopy.

Chondrogenic differentiation of BM-MSCs in static tissue culture conditions also demonstrated an expression of Type II collagen for cells seeded on nanofiber scaffolds without the presence of inductive factors in the media. Thus, these findings suggest that nanofiber architectures promote chondrogenic differentiation, even without the presence of inductive factors in the culture media.

6.14.3 In Vitro Chondrogenic Differentiation of Placental Stem Cells

To examine the chondrogenic potential of placental stem cells isolated and expanded under typical conditions, placental stem cells were grown in pellet culture in the presence of chondrogenic induction media. The duration of static cell culture experiments was limited to 28 days due to decreased cell content of pellets. Histological sections were taken to examine the pellets for functional differentiation and the presence of glycosaminoglycans (GAGs) and collagen. Quantitative protein and gene expression analyses were used to further characterize the pellets. Immune markers on differentiated placental stem cells were compared to undifferentiated placental stem cells, which are known to be immunosuppressive.

From the histological sections, it was determined that placental stem cells formed tighter pellets than BM-MSCs. Both placental stem cells and BM-MSCs stained for GAGs and collagen, while a control cell line (human dermal fibroblasts, HDF) formed loosely organized pellets with no GAGs and little collagen expression.

Protein and gene expression were used to quantify chondrogenesis by ELISA and RT-PCR, respectively. ELISA data confirmed the presence of GAGs and Type I collagen in pellets produced from placental stem cells. No Type II collagen could be found in the pellets by ELISA, but low levels of Type II collagen gene expression were found. Further, gene expression data confirmed the up-regulation of a number of chondrogenic markers in induced Placental stem cell pellets compared to uninduced pellets (Table 5)

TABLE 5

| Gene | Up-regulation |
| --- | --- |
| Aggrecan 1 | + |
| Bone morphogeneic protein 2 | ++ |
| Cartilage oligo matrix protein | ++++ |
| Cartilage-derived ret. acid sens | + |
| Collagen, type II | + |
| Collagen, type IX | + |
| Link protein | − |
| Matrilin 3 | + |
| Parathyroid hormone receptor 1 | + |
| Transcription factor SOX9 | + |

(Level of up-regulation: − = no up-regulation, + = 1-10 fold; ++ = 10-100 fold, +++ = 100-1,000 fold; and ++++ = 1,000-10,000 fold)

The potential immunogenicity of undifferentiated and chondrogenic differentiated placental stem cells was compared using flow cytometry to stain for the presence of the following immune system molecules: MHC A,B,C; MHC DR, DP, DQ; β-2-microglubulin, and CD86. The lack of expression of MHC II and CD86 and the positive expression of small amounts of MHC A,B,C and β-2-microglobulin were similar (Table 6) between undifferentiated placental stem cells and placental stem cells cultured in under chondrogenic conditions.

TABLE 6

| Marker | Undifferentiated Placental Stem Cell Expression | Chondorgenic Differentiated Placental Stem Cell Expression |
| --- | --- | --- |
| MHC Class II | None | None |
| CD 86 | None | None |
| MHC A, B, C | Low | Low |
| β-2 Microglobulin | Low | Low |

6.14.4 Characterization of Chondrogenic Differentiation of Placental Stem Cells In Vitro.

This example provides exemplary methods for achieving Objective I as set forth in Section 6.11, above. In this example, dynamic pellet cultures are used to permit lengthened culture duration. This extension permits assessment of temporal gene expression as well as biochemical and histological analyses of early and late stage markers of chondrogenesis for placental stem cells in static as well as dynamic pellet cultures for up to 56 days.

Placental stem cells are isolated from the postpartum placenta, for example, according to Example 1, above. Placental stem cells are established from disrupted tissue in, for example, a complete medium containing low concentrations of fetal calf serum and limited growth factors, according to Example 1, above. After reaching 80-85% confluence, placental stem cells are subcultured and/or cryopreserved as described elsewhere herein. Flow cytometry analysis is performed to ensure that at least 70% or more of isolated cells, for example, CD200$^+$CD105$^+$CD73$^+$CD34$^-$CD45$^-$, e.g., according to the method disclosed in Example 3, above. Functional characterization of placental stem cells further includes a chondrogenic differentiation assay.

6.14.5 Pellet Culture in Static and Dynamic Systems

Chondrogenic differentiation of placental stem cells can be carried out as follows. Placental stem cells are cultured to near confluence, trypsinized, washed 2× in incomplete chondrogenesis media (Cambrex) and resuspended at about 500,000 cells/mL in complete chondrogenic media as described above. Aliquots of 500 µL are pipetted into 15 mL polypropylene centrifuge tubes and centrifuged (800 rpm, 5 min) to induce pellet formation. Serum-free chondrogenic complete medium (CCM) consisting of 1 mM sodium pyruvate (Sigma), 0.1 mM ascorbic acid-2-phosphate (Wako), 1×10$^{-7}$ M dexamethasone (Sigma), 1% ITS (insulin-transferrin-selenium) (Collaborative Biomedical Products), and 10 ng/mL recombinant human TGF-β3 (Oncogene Sciences) dissolved in DMEM-low glucose is added to centrifuge tubes. Some pellets are transferred to bioreactors (Synthecon, model #RCCS-4H) containing serum-free CCM for dynamic culturing. Pellets under static or dynamic culture conditions are incubated at 37° C., 5% CO$_2$ and medium is exchanged every 2-3 days. At days 7, 14, 28, and 56, pellets are removed from culture and processed for gene expression, biochemical, or histological analysis. Comparisons are made with MSCs grown under static or dynamic culture condition.

To characterize the differentiated chondrocytes, pellets are washed with HEPES buffered saline without calcium and magnesium and digested with 3 mg/ml collagenase type 2, 1 mg/ml hyaluronidase, and 0.25% trypsin citrate at 37° C. After digestion the cells are spun down, resuspended in 1 ml DPBS buffer, and washed. The amount of cells recovered is determined by trypan blue dye cell count. RNA is recovered by lysing the cells with a lysis buffer. RNA is isolated using Qiagen RNEASY® kits and quantified using a Nanodrop spectrophotometer. RT-PCR for chondrogenic gene expression is performed using TAQMAN® gene expression probes. Quantitative gene expression is performed for early stage markers of fibromodulin and cartilage oligomeric matrix protein. Mid-stage markers of aggrecan, versican, decorin and biglycan are also examined. Genes for types II and X collagens and chondroadherin, which are characteristic of mature chondrocytes, are also examined.

To further characterize the differentiated chondrocytes, Enzyme-Linked Immunosorbent Assay (ELISA) assays are used to examine protein expression of chondro-differentiated placental stem cells. First, the pellets are solubilized. After obtaining a dry weight, rehydrated pellets are digested using pepsin and pancreatic elastase. The collected supernatants are used for Collagen Type II and proteoglycan ELISA. Glycosaminoglycan (GAGs) is measured by a methylene blue dye binding assay.

The differentiated chondrocytes are also subjected to histological analysis as follows. The pellets are fixed in formalin 10%, dehydrated through graded alcohols, and embedded in paraffin. Sections are cut at a thickness of 5 µm and stained with a stain for glycosaminoglycans (e.g., Alcian blue and/or Safranin-O, and a stain for collagen, e.g., Sirius Red. Alcian Blue is a copper phthalocyanine basic dye that is water-soluble and colored blue because of its copper content. When used in a 3% acetic acid solution (pH 2.5), Alcian Blue stains both sulfated and carboxylated acid mucopolysaccharides and sulfated and carboxylated sialomucins. Safranin O in the orthochromatic form stains articular cartilage, mucin and mast cell granules on formalin-fixed, paraffin embedded tissue sections. Proteoglycans stain red, cytoplasm stains gray green and nuclei stain black. Sirius Red dye can be used to differentiate different collagen types in tissue sections. Under polarized light, the fibers seemingly glow with bright colors against a black background. The color of the fibers depends on their thickness; as thickness increases, the color changes from green to yellow to orange to red. Type I collagen, which tends to form thick collagen fibers composed of closely packed thick fibrils, appears as an intense yellow to red color. Type III collagen forms thin fibers, composed of loosely disposed thin fibrils and have weak green birefringence. Thus, the color displayed is a result of the thickness of the fiber, as well as the arrangement of the collagen molecules.

Four experimental groups are used in this study; cells are grown in either standard growth media or in CCM and in static or dynamic culture systems. The quantitative assays are performed on days 7, 14, and 28, and 56. A sample size, n, of 4 is used for all quantitative biochemical assays (glycosaminoglycan, Type II collagen, and proteoglycan), gene expression, and histological analyses. One way and two way ANOVAs are performed to test for statistical differences between groups at each time point and over time, respectively for $p<0.05$. The Tukey-Kramer Method, $p<0.05$, is used to perform multiple comparisons between groups.

6.14.6 Optimization of Scaffolds for Stimulating Placental Stem Cell Chondrogenic Differentiation In Vitro.

This example describes experiments designed to achieve Objective 2, set forth above. In brief, the ability of nanofibrous scaffolds to promote placental stem cell differentiation into chondrocytes is tested. Electrospun nanofibrous scaffolds, irrespective of composition, promote mesenchymal stem cell differentiation into chondrocytes in vitro as shown above. The materials to be tested as scaffold substrates include poly(L-lactic acid) (PLLA), type I collagen and a copolymer of vinylidene fluoride and trifluoroethylene (PVDF-TrFE). Placental stem cells are loaded onto scaffolds generated from these materials and cultured in both static and dynamic conditions. Quantitative gene expression, biochemical and histological analyses as well as mechanical testing is performed during the study time course.

6.14.6.1 Scaffold Fabrication and Characterization

As described above, the electrospinning apparatus comprises a syringe fitted with a needle (16-22 gauge), mounted on a Harvard Syringe Pump Model 901. The syringe is filled with the polymer solution. The positive output lead of a high voltage power supply (Gamma High Voltage Power Supply ES30P) is attached to the needle. The collector is a stainless steel plate of dimensions 25×30 cm, which is electrically grounded. The electrospinning process is affected by varying the flow rate, solution concentration, and the diameter of the needle. The voltage applied to the solution is 20 kV, and the collector to needle distance is 20 cm. Scaffolds are collected as nonwoven mats at the collector. These scaffolds/mats are made of fibers having diameters of approximately 200-400 nm.

6.14.6.2 Polymer Solutions for Scaffold Preparation

Initial scaffolds are electrospun from solutions of a Poly L-lactic acid (Alkermes Inc., Medisorb Polymer 75/25 DL High IV) in methylene chloride. Similar scaffolds of Type I collagen (derived from bovine tendon) are produced by dissolving collagen in trifluoroacetic acid (TFA). The piezoelectric polymer, p(VDF-TrFE) is spun from a 10% solution of the polymer in methyl ethyl ketone, as previously demonstrated. See Sachlos and Czernuszka, 2003, *Eur. Cells Mater.* 5:29-40.

6.14.6.3 Scaffold Characterization

All scaffolds are examined by the following protocol. Scaffolds are imaged by polarized light optical microscopy and scanning electron microscopy. Image analysis techniques are utilized to determine average fiber diameter and coefficient of variation, as well as the area distribution between fibers. The fiber parameters of average array pore volume and pore size are by mercury porosimetry. Internal scaffold structure is monitored by a variety of thermal analysis techniques including DSC, TGA, DMA, TMA and TSC as appropriate.

For the p(VDF-TrFE) scaffold, a scan of current vs. an applied E field with a Sawyer-Tower circuit is used to identify the properties indicative of the polarizability of the p(VDF-TrFE) material. These properties include remnant and saturation polarizability, and the coercive field (the E field at which polarity switching occurs). These properties have well known values for p(VDF-TrFE) materials. The small currents injected or released by a vibrating electroded electrospun p(VDF-TrFE) mat can also be measured with an electrometer. Thermal discharge current (TSC) instrumentation is for these studies. Electroded p(VDF-TrFE) films undergo 1-10% strains in length, width and thickness when subjected to high magnitude (10-100 MV/m), periodic E fields. The strains result as the dimensions of the ferroelectric crystallite content responds to applied field. It can be expected that electroded electrospun p(VDF-TrFE) mats will undergo similar strains.

6.14.6.4 Scaffold Seeding and Differentiation Protocol

Chondrogenic differentiation of placental stem cells is carried out using media as described above, and elsewhere herein (see, e.g., Section 5.4.5, above). All scaffolds are vacuum loaded with about 200,000 cells using conventional techniques. See, e.g., Dennis et al, 1998, Biomaterials 19:1323-8. Cell-loaded scaffolds are placed in bioreactors (Synthecon, model #RCCS-4H) containing CCM. The cells are maintained in culture for up to 56 days. Medium is changed every 2-3 days. Comparisons are made with positive controls, placental stem cells grown without scaffolds using standard pellet culture conditions with CCM as described above, and with negative controls, and placental stem cells grown with or without scaffolds in the absence of CCM (using standard growth media).

6.14.6.5 Quantitative Measurements of Cartilage-Specific Extracellular Matrix Components and Cell Number Chondrogenic pellets and cell-laden scaffolds are harvested at 7, 14, 28, and 56 days and analyzed for glycosaminoglycan, Type II collagen, and proteoglycan synthesis. These assays allow for rapid, high throughput screening for cartilage markers using 96-well plate formats. To do so, the samples are washed with phosphate buffered saline and digested with 200 µL papain solution (1 µg/mL in 50 mM sodium phosphate pH 6.5, containing 2 mM N-acetyl cysteine and 2 mM EDTA) for 16 hours at 65° C. Glycosaminoglycan and proteoglycan synthesis are measured quantitatively using an ELISA kit (BLYSCAN™ Kit, Accurate Chemical and Scientific Corporation, Westbury, N.Y.). Type II collagen synthesis is measured by an ELISA kit (Arthrogen-CIA, Chondrex, Inc.). Cell number is quantified by DNA measurement, using pico-green fluorescence assay (Molecular Probes, Inc.).

6.14.6.6 Tissue Morphology by Histological Analysis

Histological staining and viewing at days 21 and 35 is used to characterize cell and tissue morphology of the chondrogenic scaffolds. Cell pellets and cell-laden scaffolds are harvested and fixed in 10% buffered formalin for 2 hours at room temperature. Pellet and scaffolds are dehydrated by treatment with a series of graded alcohols, cleared by treatment with xylene and xylene substitute, and infiltrated with paraffin. Thin sections are slide-mounted and stained with toluidine blue and safranin O.

6.14.6.7 Analysis of mRNA Changes from Differentiation

As described previously for pellet cultures, samples are washed with HEPES buffered saline without calcium and magnesium and digested with 3 mgs/ml collagenase type 2, 1 mg/ml hyaluronidase, and 0.25% trypsin citrate at 37° C. After digestion the cells are spun down, resuspended in 1 mL DPBS (Dulbecco's Phosphate-Buffered Saline) buffer, and washed. The amount of cells recovered is determined by trypan blue dye cell count. RNA is recovered by lysing the cells with a lysis buffer. RNA is isolated using Qiagen RNEASY® kits and quantified using Nanodrop. RT-PCR for chondrogenic gene expression is accomplished using TAQMAN® gene expression probes from ABI. Quantitative gene expression is performed for early stage markers of fibromodulin and cartilage oligomeric matrix protein. Midstage markers of aggrecan, versican, decorin and biglycan are also examined. Genes for types II and X collagens and chondroadherin, which are characteristic of mature chondrocytes, are also examined.

6.14.6.8 Number of Groups and Statistical Analyses

Six experimental groups are used in this study: three material compositions (PLLA, Type I Collagen, and pVDF-TrFE), and cells are grown in either standard growth media or in CCM. The quantitative assays are performed on days 7, 14, 21, and 28 days. A sample size, n, of 4 is used for all quantitative assays (glycosaminoglycan, Type II collagen, and proteoglycan). One way and two way ANOVAs are performed to test for statistical differences between groups at each time point and over time, respectively for p<0.05. The Tukey-Kramer Method, p<0.05, is used to perform multiple comparisons between groups.

6.14.7 Evaluation of In Vivo Repair of Osteochondral Defects in a Rabbit Model Using Placental Stem Cell-Scaffold Constructs.

This Example describes experiments designed to achieve Objective 3, set forth above. Briefly, scaffolds identified as supporting chondrogenic differentiation are evaluated in combination with placental stem cells in the repair of osteochondral defects in rabbits.

6.14.7.1 Animal Model

A rabbit, partial-weight bearing articular cartilage repair model is employed to study the chondrogenic effects of cell/scaffold constructs. Depending upon the number of scaffolds that support placental stem cell chondrogenesis, the number of rabbits is determined. Rabbits, New Zealand strain, are randomly assigned to the groups. An n of 4 per group is implanted. Average animal weight is between 3-5 kg and animals are specific pathogen free(SPF).

A 3.5 mm cylindrical defect is created in the intercondylar groove of the distal femur of each animal, and a cylindrical, cell/scaffold construct is implanted into the defect in a press-fit fashion. The contralateral knee of each rabbit serves as an internal control. The same defect is created and a scaffold of the same composition and architecture without cells is inserted. The knee to act as internal control is randomized by picking an opaque envelope, prior to the procedure, that states left or right as the control knee.

To implant the scaffolds, intravenous pentobarbital (45 mg/kg) is administered to initiate anesthesia. Anesthesia is maintained through inhalation of 0.5-2% isoflurane delivered in oxygen. The rabbit is placed in the supine position and each knee is shaved and prepped in a sterile fashion with a 70% alcohol scrub over the incision site. The surgical site is isolated with sterile drapes.

A lateral parapatellar incision and arthrotomy is performed. The femoral condyles are exposed by medial dislocation of the patella. A 3.5 mm drill bit is used to create the defect in the intercondylar groove of the distal femur. Defect depth is 3-5 mm in depth. The scaffold with or without cells is sutured into the defect utilizing a small absorbable suture material (6-0/7-0 vicryl). The wound is then closed in layers with absorbable sutures. The same procedure is performed on the contralateral knee as outlined above to serve as an internal control.

Post-operation, all animals are allowed weight-bearing as tolerated in their cages. Buprenorphine 0.03 mg/kg is administered every 12 hours subcutaneously for post-operative pain control for the first 5-7 days post-operatively. Regular diet is provided.

Rabbits are euthanized utilizing a lethal dose of pentobarbital at 12 weeks post-operatively. The distal femora of each rabbit are harvested. Gross evaluation of the repair site is documented for color and appearance compared to the normal surrounding tissue; evidence of joint arthrosis is documented as well. Specimens (n=4 per group) are decalcified and paraffin embedded for histological evaluation and staining. Histological evaluation is graded utilizing a modified O'Driscoll score. N=8 specimens per group are used for mechanical testing. Compression testing is performed based on previously reported protocols for nanofibrous scaffolds.

6.15 Example 15: Identification of a $CD34^+CD45^-$ Cell Population in Placental Perfusate The purpose of this study was to phenotypically characterize and compare cells from matched placenta perfusate (HPP) and cord blood (HUCB) units (n=10) and to identify additional useful cell surface markers for placenta perfusate using multi-parameter flow cytometry. To assess the quality of the cells, total nucleated cells (TNCs) and cell viability were also measured. Since post-thaw samples are close to the condition of cells prior to their use in preclinical or clinical studies, characterization of the placenta perfusate focused on these samples. For comparison purposes, a donor matched cord blood for each placenta unit was tested. Including matched HUCB units in this project allowed evaluation of the differences between cell populations in the placenta perfusate and umbilical cord blood collected from the same donor.

Materials and Methods:

Placental perfusates were obtained from perfusion of placentas from normal births using 0.9% NaCl. Matched units of umbilical cord blood were collected and cryopreserved by standard methods, and thawed immediately prior to use. Frozen HPP and HUCB samples were drawn from a liquid nitrogen tank and thawed in a 37° C. water bath immediately. Cells were assessed by flow cytometry, by washing the cells in PBS with 2% fetal calf serum, staining with conjugated antibodies, and analyzing using either a BD FacsCalibur or a BD ARIA (Becton Dickinson, San Jose, Calif.). Antibodies used included PE-CD34 (BD Cat#348057) and PerCP-CD45 (BD Cat#340665). Cell sorting experiments were performed after staining with the appropriate antibodies and cells were placed in a standard CFU assay system using MethoCult.

Results:

Flow cytometry determined that a cell having a $CD34^+CD45^-$ phenotype was 4-fold enriched in HPP as compared to HUCB (FIG. 10). Data in Table 7 was derived from HPP and HUCB cells that were sorted using the FACS ARIA cell sorted for Becton Dickinson. Placental perfusate stem cells were sorted based on the following phenotypes: $CD34^-CD45^-$, $CD34^+CD45^-$ and $CD34^+CD45^+$. The double negative cell type was not expected to produce any CFU and served as a sort purity control. The $CD34^+CD45^+$ cell type is the classical CB stem cell and served as the positive control for the sort and the CFU assay. The test phenotype of $CD34^+CD45^-$ was not present in sufficient quantities in the HUCB to allow for sorting and CFU, but from HPP cells were obtained. As seen in Table 1, cells from HPP gave rise to larger numbers of CFU-E and BFU-E, as well as providing the same CFU pattern as found in HUCB. In addition, the HPP $CD34^+CD45^+$ cells provided CFU-GEMM, a population not detected in HUCB nor produced by $CD34^+CD45^+$ cells in HUCB.

TABLE 7

| Unit # | CFU DATA Chart CD34−; CD45− Cells CFU-E/BFU-E 1000 cells/well | 3000 cells/well | 9000 cells/well | CFU-GM 1000 cells/well | 3000 cells/well | 9000 cells/well | CFU-GEMM 1000 cells/well | 3000 cells/well | 9000 cells/well |
|---|---|---|---|---|---|---|---|---|---|
| 327950HPP | 0 | 0 | 0 | 0 | 0 | 0 | 0 | 0 | 0 |
| 327940CB | 0 | 0 | 0 | 2 | 2 | 0 | 0 | 0 | 0 |

| Unit # | CD34+; CD45− Cells CFU-E/BFU-E 50 cells/well | 150 cells/well | 450 cells/well | 1000 cells/well | CFU-GM 50 cells/well | 150 cells/well | 450 cells/well | 1000 cells/well | CFU-GEMM 50 cells/well | 150 cells/well | 450 cells/well | 1000 cells/well |
|---|---|---|---|---|---|---|---|---|---|---|---|---|
| 327950HPP | 0 | 2 | 0 | 1 | 0 | 0 | 0 | 1 | 0 | 0 | 0 | 0 |
| 327940CB | N/A | N/A | N/A | N/A | N/A | N/A | N/A | N/A | N/A | N/A | N/A | N/A |

| Unit # | CD34+; CD45+ Cells CFU-E/BFU-E 50 cells/well | 150 cells/well | 450 cells/well | CFU-GM 50 cells/well | 150 cells/well | 450 cells/well | CFU-GEMM 50 cells/well | 150 cells/well | 450 cells/well |
|---|---|---|---|---|---|---|---|---|---|
| 327950HPP | 1 | 4 | 7 | 4 | 4 | 5 | 0 | 0 | 0 |
| 327940CB | 0 | 0 | 1 | 5 | 12 | 0 | 0 | 0 | 0 |

| | Duplicate wells CD34−; CD45− Cells | | | | | | | | |
|---|---|---|---|---|---|---|---|---|---|
| | CFU-E/BFU-E | | | CFU-GM | | | CFU-GEMM | | |
| Unit # | 1000 cells/well | 3000 cells/well | 9000 cells/well | 1000 cells/well | 3000 cells/well | 9000 cells/well | 1000 cells/well | 3000 cells/well | 9000 cells/well |
| 327950HPP | 0 | 0 | 0 | 0 | 0 | 0 | 0 | 0 | 0 |
| 327940CB | 0 | 0 | 0 | 0 | 1 | 0 | 0 | 0 | 0 |

| | CD34+; CD45− Cells | | | | | | | | | | | |
|---|---|---|---|---|---|---|---|---|---|---|---|---|
| | CFU-E/BFU-E | | | | CFU-GM | | | | CFU-GEMM | | | |
| Unit # | 50 cells/well | 150 cells/well | 450 cells/well | 1000 cells/well | 50 cells/well | 150 cells/well | 450 cells/well | 1000 cells/well | 50 cells/well | 150 cells/well | 450 cells/well | 1000 cells/well |
| 327950HPP | 0 | 1 | 2 | 1 | 0 | 0 | 1 | 0 | 0 | 0 | 0 | 0 |
| 327940CB | N/A | N/A | N/A | N/A | N/A | N/A | N/A | N/A | N/A | N/A | N/A | N/A |

TABLE 7-continued

| | CD34+; CD45+ Cells | | | | | | | | |
|---|---|---|---|---|---|---|---|---|---|
| | CFU-E/BFU-E | | | CFU-GM | | | CFU-GEMM | | |
| | 50 cells/well | 150 cells/well | 450 cells/well | 50 cells/well | 150 cells/well | 450 cells/well | 50 cells/well | 150 cells/well | 450 cells/well |
| 327950HPP | 3 | 2 | 8 | 2 | 2 | 14 | 0 | 0 | 0 |
| 327940CB | 0 | 0 | 0 | 16 | 14 | 0 | 0 | 0 | 0 |

HPP: human placental perfusate
CB: Cord blood
CFU-E/BFU-E: colony forming unit, erythrocyte/blast forming unit erythrocyte
CFU-GM: colony forming unit, granulocyte macrophage
CFU-GEMM: colony forming unit, granulocyte, erythrocyte, monocyte, megakaryocyte In another study, CD34, CD45, CD31 and CDH5 gene expression levels were compared in CD34$^+$CD45$^-$ and CD34$^+$CD45$^+$ cell populations isolated from the same placental perfusate (HPP).

Materials and Methods:

CD34$^+$CD45$^-$ and CD34$^+$CD45$^+$ cell populations were obtained as described above with cell purity greater than 90%, and subjected to RNA preparation using RNAQUEOUS®-4PCR Kit (Ambion, Cat #AM1914). In brief, the isolated cells (5×10$^5$ cells) were lysed in the guanidinium lysis solution. The sample lysate was then mixed with an ethanol solution, and applied to a silica-based filter which selectively and quantitatively binds mRNA and the larger ribosomal RNAs. Very small RNAs such as tRNA and 5S ribosomal RNA were not quantitatively bound. The filter was then washed to remove residual DNA, protein, and other contaminants, and the RNA was eluted in nuclease-free water containing a trace amount of EDTA to chelate heavy metals. The silica filter was housed in a small cartridge which fits into the RNase-free microfuge tubes supplied with the kit. The sample lysate, wash solutions, and elution solution were moved through the filter by centrifugation or vacuum pressure. After elution from the filter the RNA was treated with the ultra-pure DNase 1 provided with the kit to remove trace amounts of DNA. Finally, the DNase and divalent cations were removed by a reagent also provided with the kit. The concentration and purity of the recovered RNA was determined by measuring its absorbance at 260 and 280 nm. The RNA can then be used for cDNA synthesis using TAQMAN® Reverse Transcription Reagents (Applied Biosystems, Cat #N8080234) followed by real-time PCR analysis by 7900HT Fast Real-Time PCR System using Taqman Gene Expression Assays of CD34 (Applied Biosystems, Cat #Hs0099073_m1), CD45 (Applied Biosystems, Cat #Hs00236304_m1), CD31 (Applied Biosystems, Cat #Hs01065289_m1), and CDH5 (Applied Biosystems, Cat #Hs00174344_m1).

Results:

Real-time PCR analysis determined that CD34 expression in CD34$^+$CD45$^-$ and CD34$^+$CD45$^+$ cells was comparable. As expected, CD45 expression was not detectable in CD34$^+$CD45$^-$ cells, but was, however, detectable in CD34$^+$CD45$^+$ cells. CD31 expression in CD34$^+$CD45$^+$ cells was 0.05% of that in CD34$^+$CD45$^-$ cells. CDH5 expression in CD34$^+$CD45$^+$ cells was 13.66% of that in CD34$^+$CD45$^-$ cells.

6.16 Example 16: Enrichment of CD34$^+$ Cells from Human Placenta Perfusate

This example describes the enrichment of CD34$^+$ cells from human placenta using magnetic antibody-coated-bead separation (MACS).

A cell suspension from human placental perfusate is obtained and resuspended in MACS buffer (PBS pH 7.2, +0.5% BSA+2 mmol EDTA) containing ACD (anticoagulant citrate dextrose). An aliquot is collected for a first flow sample. 6 mL of Ficoll is added to a separate 15 mL tube, and the cell suspension is layered over Ficoll very slowly. The cell suspension in Ficoll is centrifuged at 300×g (avg.) for 35 minutes, 20° C., no brake in a Beckman coulter Allegra X12R Centrifuge with a SC4750 rotor. Upon completion of centrifugation, the supernatant is aspirated carefully, and the mononuclear cells settled at the interface are collected into a separate tube. This material is resuspended to a total volume of 10 mL with MACS buffer containing ACD. An aliquot is collected for a second flow sample. Cells are counted and checked for viability. The cells are then centrifuged at 400×g (avg.) in an SC4750 rotor for 15 minutes at 4° C. When centrifugation is completed, the supernatant is aspirated, and the cells are resuspended to 100 µL in MACS buffer containing ACD. STEMSEP™ selection cocktail (StemCell Technologies, Inc., Vancouver, BC Canada) is added at a concentration of 100 µL/1 mL of cells (at concentration of 1 µL/2×10$^6$ cells). The cells and cocktail are mixed well and incubated for 10 minutes at 4-8° C. Magnetic colloid is added at 60 µL/1 mL of cells (at concentration of 1 µL/3.33×10$^6$ cells). The cells and colloid are mixed well and incubated for 10 minutes at 4-8° C. A 10× volume of refrigerated MACS buffer containing ACD is then added to the cells, and the resulting solution is centrifuged at 400×g (avg.) in an SC4750 rotor for 8 minutes at room temperature. The supernatant is aspirated, and the cells are resuspended in 2 mL of MACS buffer containing ACD. The suspension is optionally filtered at this point. A third aliquot is collected for a flow sample. Cells are then analyzed on an AUTOMACS™ automated magnetic cell sorter (Miltenyi Biotec) using program POSSELD2, placing collection tubes at positions "POS 2" and "NEG1". About 2 mL of positively selected cells are collected. The cell suspension is then washed and centrifuged at 400×g (SC4750 rotor) for 10 minutes at room temperature and resuspended to 1 mL in PBS containing 1% FBS.

6.17 Example 17: In Vitro Colony Forming Unit Assay

Total nucleated cells are isolated from a unit of cord blood by Hetastarch separation. Total nucleated placental cells are obtained from 750 milliliters of placental perfusate by Ficoll separation. The total nucleated cells from placenta and cord blood are combined in triplicate in 35 mm culture dishes in Methocult GF$^+$ H4435 medium (Stem Cell Technologies, Vancouver, Canada), or RPMI 1640 medium supplemented with 2% fetal calf serum and 1% Stemspan CC100 cytokine cocktail (Stem Cell Technologies, Vancouver, Canada). Cells are combined in at least two ratios (e.g., $2\times10^5:2\times10^5$; $1\times10^5:3\times10^5$; $3\times10^5:1\times10^5$), and are cultured for 14 days. The morphology of the cells is then examined under phase contrast microscope, and the total number of colony-forming units (e.g., CFU-GM, CFU-L, CFU-M, CFU-G, CFU-DC, CFU-GEMM, CFU-E) are recorded. A determination is then made as to which ratio produces the highest number of colony-forming units.

EQUIVALENTS

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. A method of producing an isolated $CD34^+$, $CD45^-$ hematopoietic placental stem cell population, comprising selecting $CD34^+$ cells from a population of placental cells using antibodies to form a population of $CD34^+$ placental cells, removing from said population of $CD34^+$ placental cells $CD45^+$ cells using antibodies, and combining the resulting cells with a physiologically-acceptable aqueous saline solution, wherein a $CD34^+$, $CD45^-$ hematopoietic placental stem cell population is produced.

2. The method of claim 1, wherein said population produces CFU-E or BFU-E when cultured in vitro.

3. The method of claim 1, wherein at least 50% of cells in said population are $CD34^+$, $CD45^-$.

4. The method of claim 1, wherein at least 70% of cells in said population are $CD34^+$, $CD45^-$.

5. The method of claim 1, wherein at least 90% of cells in said population are $CD34^+$, $CD45^-$.

* * * * *